US011234445B2

(12) United States Patent
Bihain et al.

(10) Patent No.: US 11,234,445 B2
(45) Date of Patent: Feb. 1, 2022

(54) MOLECULAR ORIGIN OF ALLERGY

(71) Applicant: GENCLIS, Vandoeuvre les Nancy (FR)

(72) Inventors: Bernard Bihain, Nancy (FR); Virginie Ogier, Laxou (FR); Marie Brulliard, Nancy (FR); Sandrine Jacquenet, Villers-les-Nancy (FR); Benoit Thouvenot, Chaligny (FR); Olivier Roitel, Saint Nicolas de Port (FR)

(73) Assignee: GENCLIS, Vandoeuvre les Nancy (FR)

( * ) Notice: Subject to any disclaimer, the term of this patent is extended or adjusted under 35 U.S.C. 154(b) by 451 days.

(21) Appl. No.: 16/085,043

(22) PCT Filed: Mar. 20, 2017

(86) PCT No.: PCT/EP2017/056576
§ 371 (c)(1),
(2) Date: Sep. 14, 2018

(87) PCT Pub. No.: WO2017/158202
PCT Pub. Date: Sep. 21, 2017

(65) Prior Publication Data
US 2019/0116822 A1 Apr. 25, 2019

(30) Foreign Application Priority Data

Mar. 18, 2016 (EP) .................................... 16305297

(51) Int. Cl.
*A23J 3/00* (2006.01)
*A23J 3/08* (2006.01)
*A23J 3/14* (2006.01)
*A23L 5/20* (2016.01)
*C07K 1/18* (2006.01)
*A23C 9/146* (2006.01)
*C07K 1/22* (2006.01)
*G01N 33/68* (2006.01)
*A23C 9/20* (2006.01)
*C07K 14/415* (2006.01)
*A23K 10/20* (2016.01)
*B01D 15/36* (2006.01)
*B01D 15/38* (2006.01)

(52) U.S. Cl.
CPC .............. *A23C 9/1465* (2013.01); *A23C 9/20* (2013.01); *A23J 3/00* (2013.01); *A23J 3/08* (2013.01); *A23J 3/14* (2013.01); *A23K 10/20* (2016.05); *A23L 5/27* (2016.08); *A23L 5/273* (2016.08); *B01D 15/362* (2013.01); *B01D 15/3809* (2013.01); *C07K 1/18* (2013.01); *C07K 1/22* (2013.01); *C07K 14/415* (2013.01); *G01N 33/6854* (2013.01); *A23V 2002/00* (2013.01); *A23V 2200/03* (2013.01); *A23V 2300/30* (2013.01); *G01N 2800/24* (2013.01); *G01N 2800/50* (2013.01)

(58) Field of Classification Search
CPC .............. B01D 15/362; B01D 15/3809; A23C 9/1465; A23L 5/273; A23L 15/00; A23L 25/00; A23V 2200/03; A23V 2300/30; A23J 1/08; A23J 1/14; A23J 3/00; A23J 3/04; A23J 3/08; A23J 3/14; A61K 39/00; C07K 1/18
See application file for complete search history.

(56) References Cited

U.S. PATENT DOCUMENTS

| 5,849,885 | A | * | 12/1998 | Nuyens | ................ | A23C 9/1465 |
| | | | | | | 530/416 |
| 6,544,498 | B1 | * | 4/2003 | Takada | .................... | A61P 1/02 |
| | | | | | | 424/49 |
| 8,288,091 | B2 | | 10/2012 | Bihain | | |
| 9,068,988 | B2 | | 6/2015 | Bihain et al. | | |
| 2011/0008361 | A1 | * | 1/2011 | Bragger | ................ | A61K 38/40 |
| | | | | | | 424/157.1 |
| 2011/0053787 | A1 | | 3/2011 | Brulliard et al. | | |

FOREIGN PATENT DOCUMENTS

| EP | 1 130 028 | 9/2001 |
| EP | 1 887 088 | 2/2008 |
| WO | WO 01/80665 | 11/2001 |
| WO | WO 2006/097120 | 9/2006 |

OTHER PUBLICATIONS

Crevel et al. Allergenicity of Refined Vegetable Oils. Food and Chemical Toxicology. 2000, vol. 38, pp. 385-393. (Year: 2000).*
Osterlund, P. et al. "Eosinophil Cationic Protein in Human Milk Is Associated with Development of Cow's Milk Allergy and Atopic Eczema in Breast-fed Infants" Pediatric Research, 2004, pp. 296-301, vol. 55, No. 2.
Watanabe, M. "Hypoallergenic rice as a physiologically functional food" Trends in Food Science & Technology, May 1993, pp. 125-128, vol. 4.
Jeon, C. et al. "Fidelity of RNA polymerase II transcription controlled by elongation factor TFIIS" Proc. Natl. Acad. Sci. USA, Nov. 1996, pp. 13677-13682, vol. 93.
Saiz, J. et al. "Peanut Allergens: An Overview" Critical Reviews in Food Science and Nutrition, 2013, pp. 722-737, vol. 53.

(Continued)

Primary Examiner — Jeffrey E. Russel
(74) Attorney, Agent, or Firm — Saliwanchik, Lloyd & Eisenschenk

(57) ABSTRACT

The present invention relates to compositions and methods for modulating or detecting allergy in a subject. The invention may be used to reduce allergenicity of compositions, such as food products, or to stimulate immunogenicity of products, such as vaccines by removal of cationic proteins resulting from transcription infidelity. The invention may be used in any mammal such as human.

Figure 1:
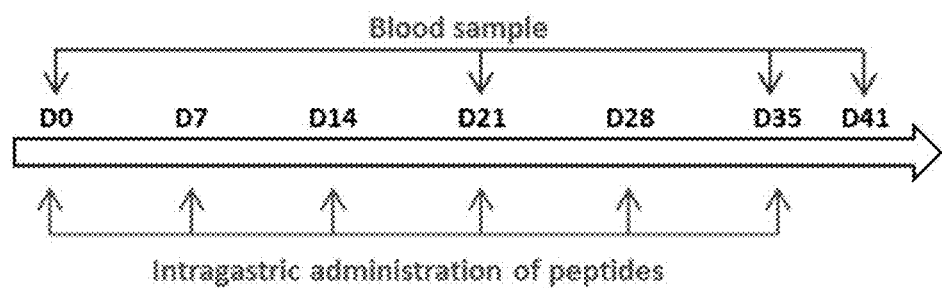
Figure 1:
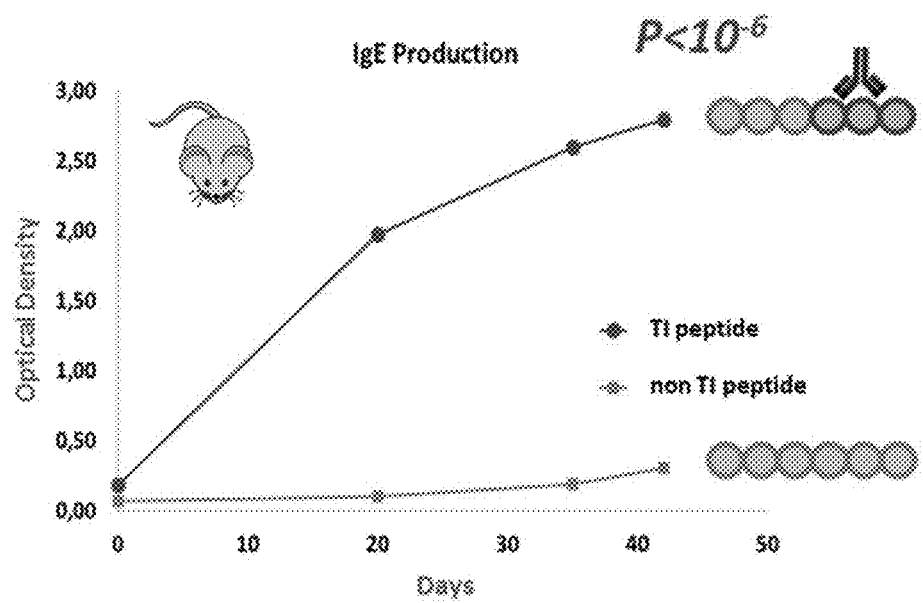

18 Claims, 11 Drawing Sheets
(4 of 11 Drawing Sheet(s) Filed in Color)
Specification includes a Sequence Listing.

(56) References Cited

OTHER PUBLICATIONS

Written Opinion in International Application No. PCT/EP2017/056576, dated Jun. 12, 2017, pp. 1-7.
Database IBIS [Online] Accession No. BAJ49777, Feb. 14, 2013, pp. 1-2, XP-002757951.

* cited by examiner

MOLECULAR ORIGIN OF ALLERGY

CROSS-REFERENCE TO RELATED APPLICATION

This application is the U.S. national stage application of International Patent Application No. PCT/EP2017/056576, filed Mar. 20, 2017.

The Sequence Listing for this application is labeled "Seq-List.txt" which was created on Sep. 13, 2018 and is 199 KB. The entire content of the sequence listing is incorporated herein by reference in its entirety.

The present invention relates to compositions and methods for modulating or detecting allergy in a subject. The invention stems from the discovery, by the inventors, of a molecular origin of allergy in mammals and has wide uses in medical, nutritional, cosmetic or agricultural industries, for instance. The invention may be used to reduce allergenicity of compositions, such as food products, or to stimulate immunogenicity of products, such as vaccines. The invention may be used in any mammal such as human.

BACKGROUND

Clinical manifestations of allergic reactions are highly diversified affecting virtually all organs that can be in contact with external environment i.e. respiratory, skin, digestive and gyneco urinary and can culminate in systemic anaphylactic shock with more or less serious haemodynamic consequences. IgE antibody are the cornerstone of Type I hypersensitivity causing diseases such as Asthma, Hay Fever, Eczema, Urticaria, food allergies and anaphylaxis. IgE are both circulating and anchored to FcεRI expressed at the surface of mast cells, basophils, eosinophils, monocytes, macrophages and Langerhans cells. Allergen induced cross-linking of IgE anchored to FcεRI on tissue mast cells elicit a cascade of events liberating histamine and multiple cytokines that contribute to both amplification of the reaction by recruiting circulating basophils also armed with IgE anchored to FcεRI. While these events have been characterized in great details, the simple question as to why any given protein that for most individuals is harmless becomes a potentially lethal allergen for others remains unanswered. The work presented here explains that the initial trigger of IgE production stems not from known allergens but from minute amount of variants translated from mRNA with frame shift caused by transcriptional errors.

SUMMARY

The invention stems from the discovery, by the inventors, of a molecular origin of allergy in mammals. The invention thus provides novel compositions and methods for detecting, controlling or modulating an immune response or allergy in mammals. The invention particularly stems from the discovery, by the inventors, that allergy is triggered by proteins (or epitopes thereof) generated by transcription infidelity ("TI") in mammals. In particular, as previously demonstrated by the inventors, TI generates aberrant proteins with modified C-terminal ends. Continuing their investigations, the inventors have now surprisingly found that TI gaps create proteins which acquire immunogenicity in mammals and trigger allergy in vivo. The inventors have also found that such proteins resulting from TI gaps are essentially cationic and that removing such proteins from food or other compositions generates hypoallergenic compositions.

The present invention thus provides novel compositions and methods for detecting, monitoring and modulating immunogenicity and allergy in mammals.

An object of the invention more particularly resides in a method for reducing allergenicity or immunogenicity of a composition, the method comprising treating the composition to remove cationic proteins.

An object of the invention resides in a method for reducing allergenicity or immunogenicity of a composition, the method comprising treating the composition to remove proteins resulting from transcription infidelity, more particularly proteins having a sequence resulting from a transcription infidelity gap.

The composition may be any composition such as a food, feed, pharmaceutical product, veterinary product, cosmetic product, etc.

In a particular embodiment, the invention provides a method for preparing a food product comprising (i) providing a food product preparation, (ii) treating the food product preparation to remove cationic proteins therefrom and (iii) optionally formulating the treated food product with one or more suitable excipients.

Another particular embodiment of the invention relates to a method for preparing a pharmaceutical product comprising (i) providing a pharmaceutical product preparation, (ii) treating the pharmaceutical product preparation to remove cationic proteins therefrom and (iii) optionally formulating the treated pharmaceutical product with one or more suitable excipients.

The invention also provides food compositions comprising a food product and a suitable excipient, wherein the food product contains less than 1% by weight of cationic proteins, more preferably less than 0.5%, less than 0.3%, less than 0.2%, or less than 0.1%.

The invention also provides pharmaceutical compositions comprising a pharmaceutical/veterinary product and a suitable excipient, wherein the pharmaceutical/veterinary product has been treated to contains less than 1% by weight of cationic proteins, more preferably less than 0.5%, less than 0.3%, less than 0.2%, or less than 0.1%.

The invention also relates to a method of treating a subject, comprising administering to the subject an effective amount of a pharmaceutical or veterinary product as defined above.

The invention also provides a method for detecting a subject having predisposition to allergy, comprising measuring in a sample from said subject the level of IgE directed against proteins having a sequence resulting from a transcription infidelity, wherein a difference in said level as compared to a control value indicates a subject having predisposition to allergy.

A further object of the invention is a cationic protein or peptide having a sequence resulting from transcription infidelity, for use as an adjuvant (e.g., to stimulate antibody production in a mammal).

The invention also provides a method of inducing or stimulating antibody production in a mammal, comprising administering to the mammal a cationic protein or peptide having a sequence resulting from transcription infidelity.

The invention further provides a method for producing IgE comprising (i) administering to a non-human mammal a cationic protein or peptide resulting from transcription infidelity under conditions allowing induction of IgE production, and (ii) collecting IgE produced.

The invention further provides a method for producing IgE comprising (i) administering to a non-human mammal a cationic protein or peptide resulting from transcription infidelity under conditions allowing induction of IgE production, (ii) collecting IgE-producing cells and (iii) deriving monoclonal and/or humanized IgE from said collected cells. Step (iii) typically comprises producing hybridoma, clonal selection of hybridomas and production of monoclonal antibodies.

The invention also concerns a method of making anti-IgE antibodies, comprising (i) administering to a non-human mammal a cationic protein or peptide resulting from transcription infidelity under conditions allowing induction of antibodies, (ii) collecting antibodies produced and (iii) selecting antibodies that bind Fc receptor.

A further object of the invention is a pharmaceutical composition comprising an antibody that binds Fc receptor.

The invention also provides a vaccine composition comprising an immunogen and a protein or peptide having a sequence resulting from transcription infidelity.

LEGEND TO THE FIGURES

The patent or application file contains at least one drawing executed in color. Copies of this patent or patent application publication, with color drawing(s), will be provided by the Office upon request and payment of the necessary fee.

FIG. 1. IgE production after intragastric administration of TI and non-TI peptides. The days of administration of the peptides and the collection of blood from the mice are indicated in the upper part. The assay of IgEs in the blood is carried out by the ELISA technique and the results are expressed as optical density. The difference between the two peptides is significant ($p<10^{-6}$).

Figure 2:
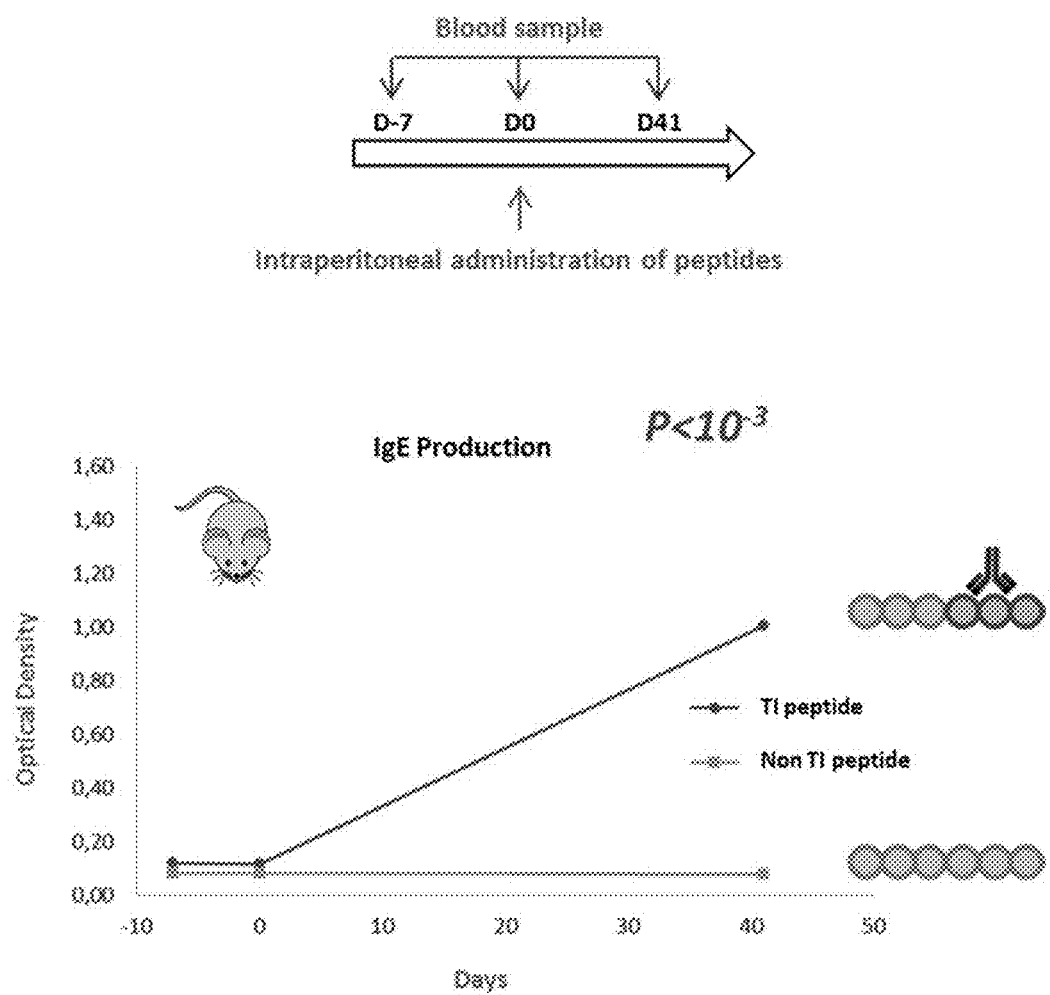

FIG. 2. IgE production after intraperitoneal administration of TI and non-TI peptides. The days of administration of the peptides and the collection of blood from the mice are indicated in the upper part. The assay of IgEs in the blood is carried out by the ELISA technique and the results are expressed as optical density. The difference between the two peptides is significant ($p<10^{-3}$).

Figure 3:
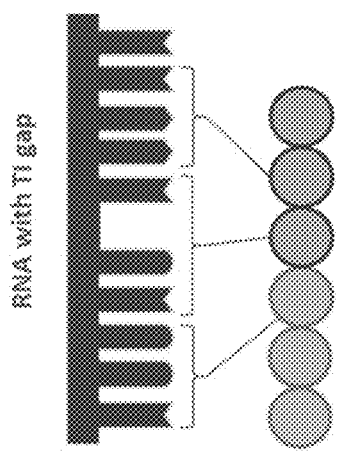
Figure 3:
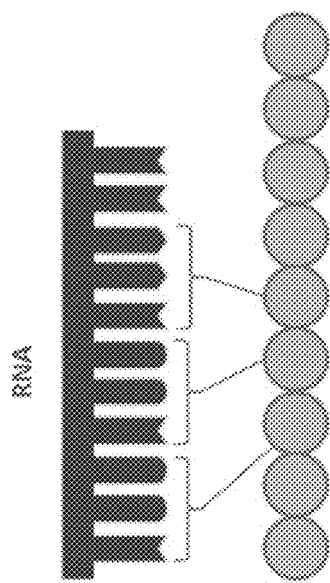

FIG. 3. A TI gap (in red) on the RNA causes a shift in the reading frame of the protein. The sequence of the protein resulting from the gap is very different from the normal protein.

Figure 4:
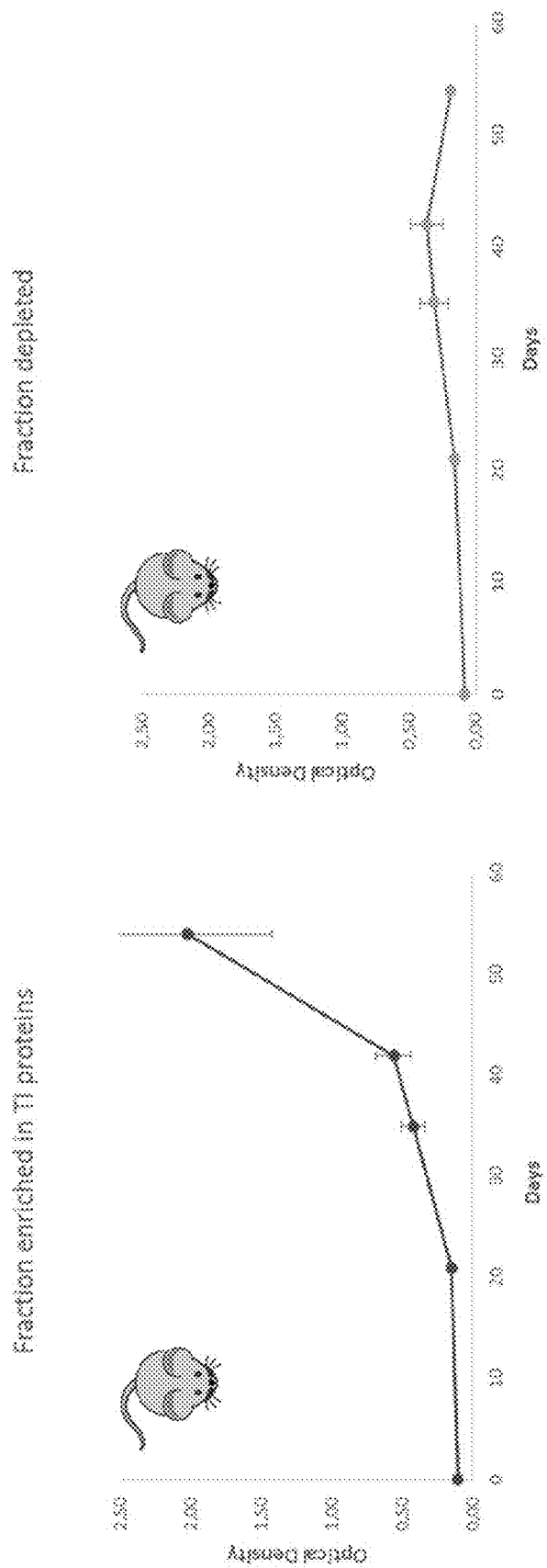

FIG. 4. Administration to mice of fractions enriched in and depleted of cationic proteins (6 mice per group). From blood samples, the assay of IgEs is carried out by the ELISA technique and the results are expressed as optical density. The error bars indicate the variability of the measurement for the whole group.

Figure 5:
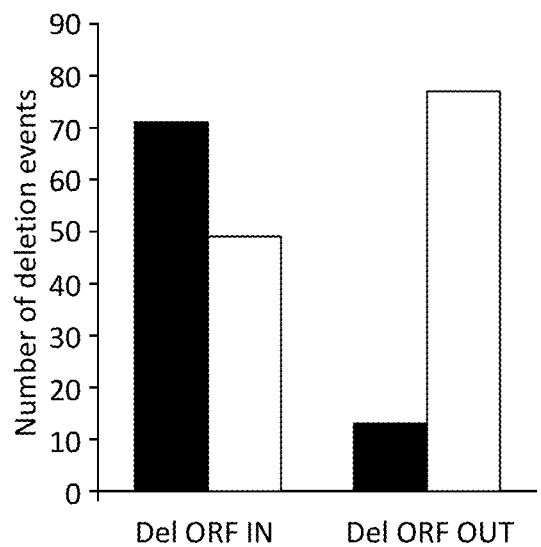

FIG. 5: Deletions are mainly located within ORF of allergens. Number of deletions has been determined for allergens (black) and non-allergens (white). The position of the deletion is then defined as ORF IN (located within the coding sequence) or ORF OUT (located within untranslated regions).

Figure 6:
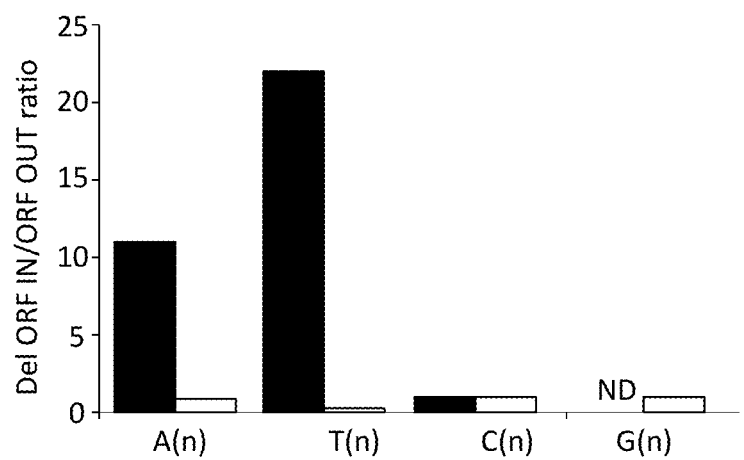

FIG. 6: Ratio between the number of deletions located within ORF and within UTR, for allergens (black) and non-allergens (white), for deletions affecting repetitions of A, T, C and G. ND: non determined (there is no deletion affecting repetitions of G in the allergens).

Figure 7A:
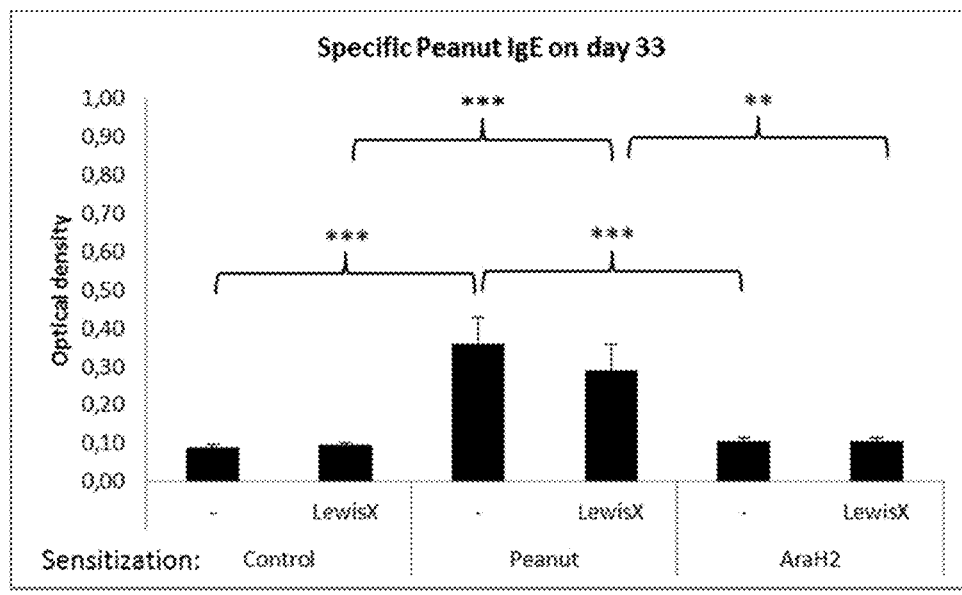
Figure 7B:
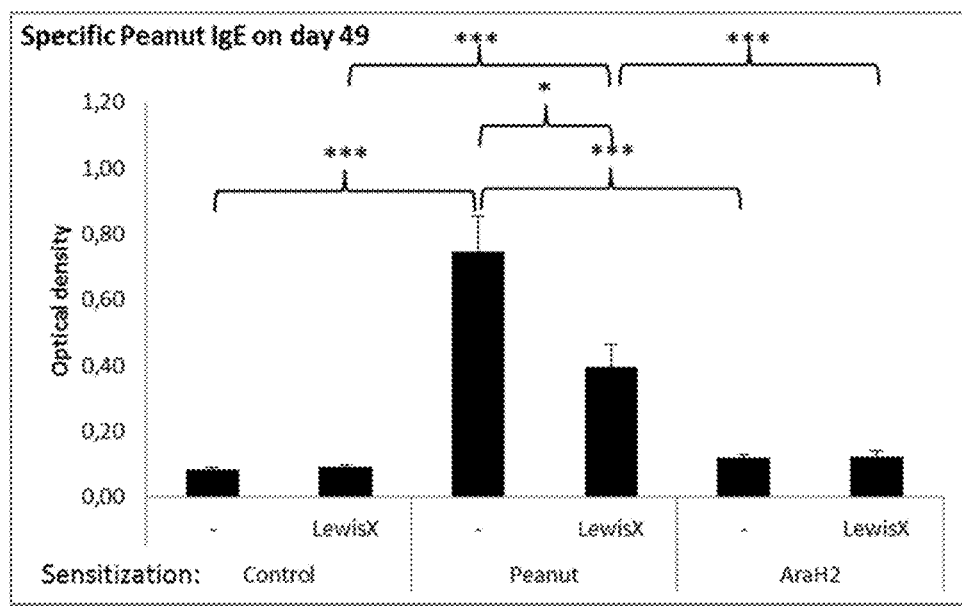

FIGS. 7A and 7B: IgE antibody responses to peanut on day 33 (A) and on day 49 (B). Mice (n=10 per treatment group, per experiment) received peanut extract (400 μg protein) or recombinant AraH2 (400 μg) by intra peritoneal injection on days 0, 7, 14 and 36, with or without LewisX adjuvant. Serum samples (days 33 and 49) were analyzed for specific IgE antibody by ELISA. Data are shown as mean (±SEM). Non parametric Wilcoxon test are performed (* $p<0.05$,  $p<0.01$, * $p<0.001$).

Figure 8:
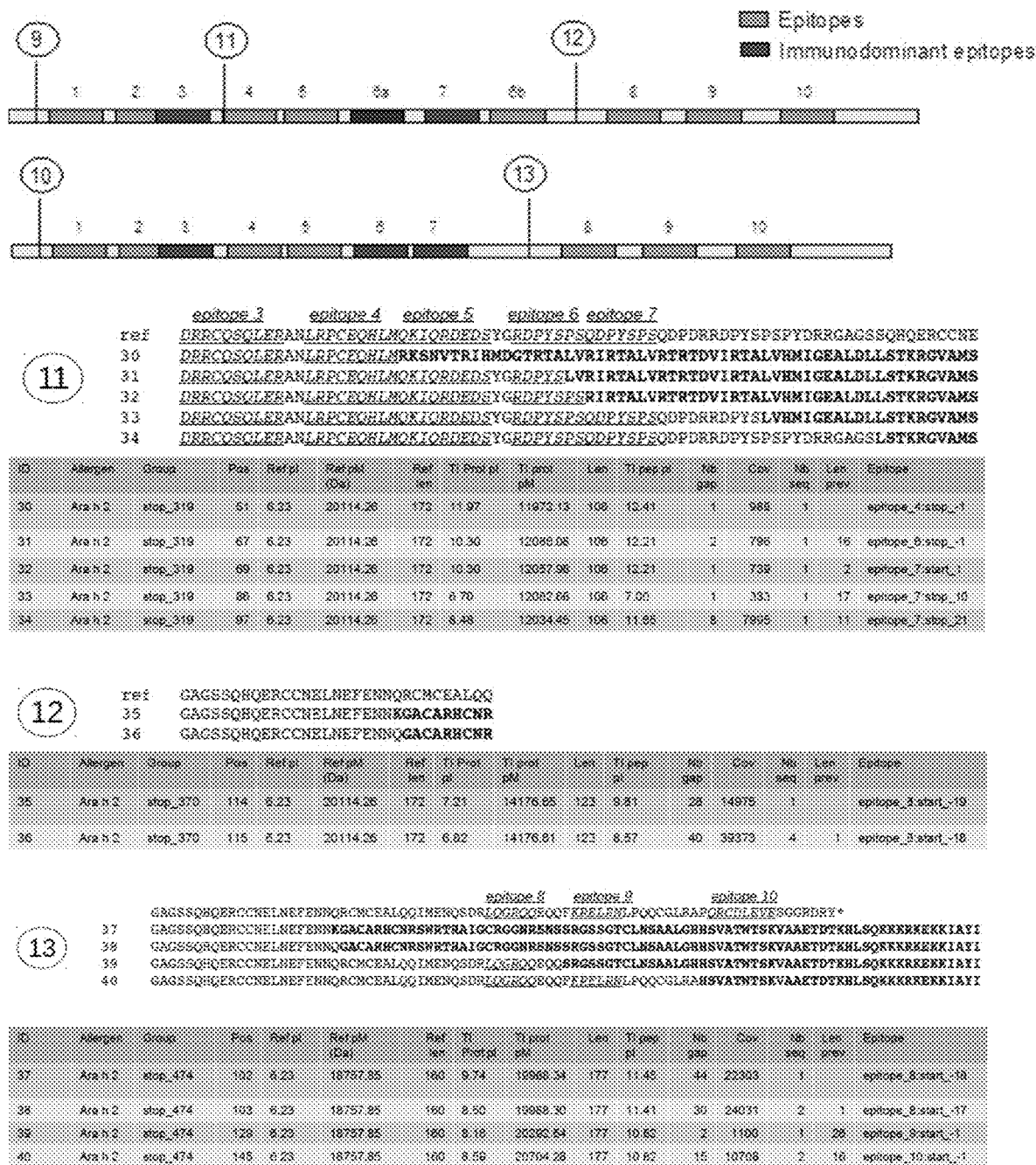

FIG. 8: Positions of deletions affecting Ara h 2 and prediction of TI proteins and peptides. Two isoforms are shown. Epitopes from each isoform are represented in grey and immunodominant epitopes are represented in black. Vertical bars indicate the positions of group of deletions implying the same stop codon. For some groups, sequences are shown. Transcription infidelity (TI) sequences are bold; epitopes are underlined. Diagrams 11 (ref, residues 11-87 of SEQ ID NO: 126; 30, residues 11-87 of SEQ ID NO: 121; 31, residues 11-87 of SEQ ID NO: 122; 32, residues 11-87 of 123; 33, residues 11-87 of SEQ ID NO: 124; 34, residues 11-87 of SEQ ID NO: 125), 12 (ref, residues 62-92 of SEQ ID NO: 130; 35, residues 74-104 of SEQ ID NO: 126; 36, residues 74-104 of SEQ ID NO: 127) and 13 (top row, residues 74-153 of SEQ ID NO: 132; 37, residues 62-158 of SEQ ID NO: 128; 38, residues 62-158 of SEQ ID NO: 129; 39, residues 62-158 of SEQ ID NO: 130; 40, residues 62-158 of SEQ ID NO: 131) also contain biochemical and bioinformatical characteristics of these TI variants. Stop codon of reference sequence is labelled with an asterisk.

Figure 9:
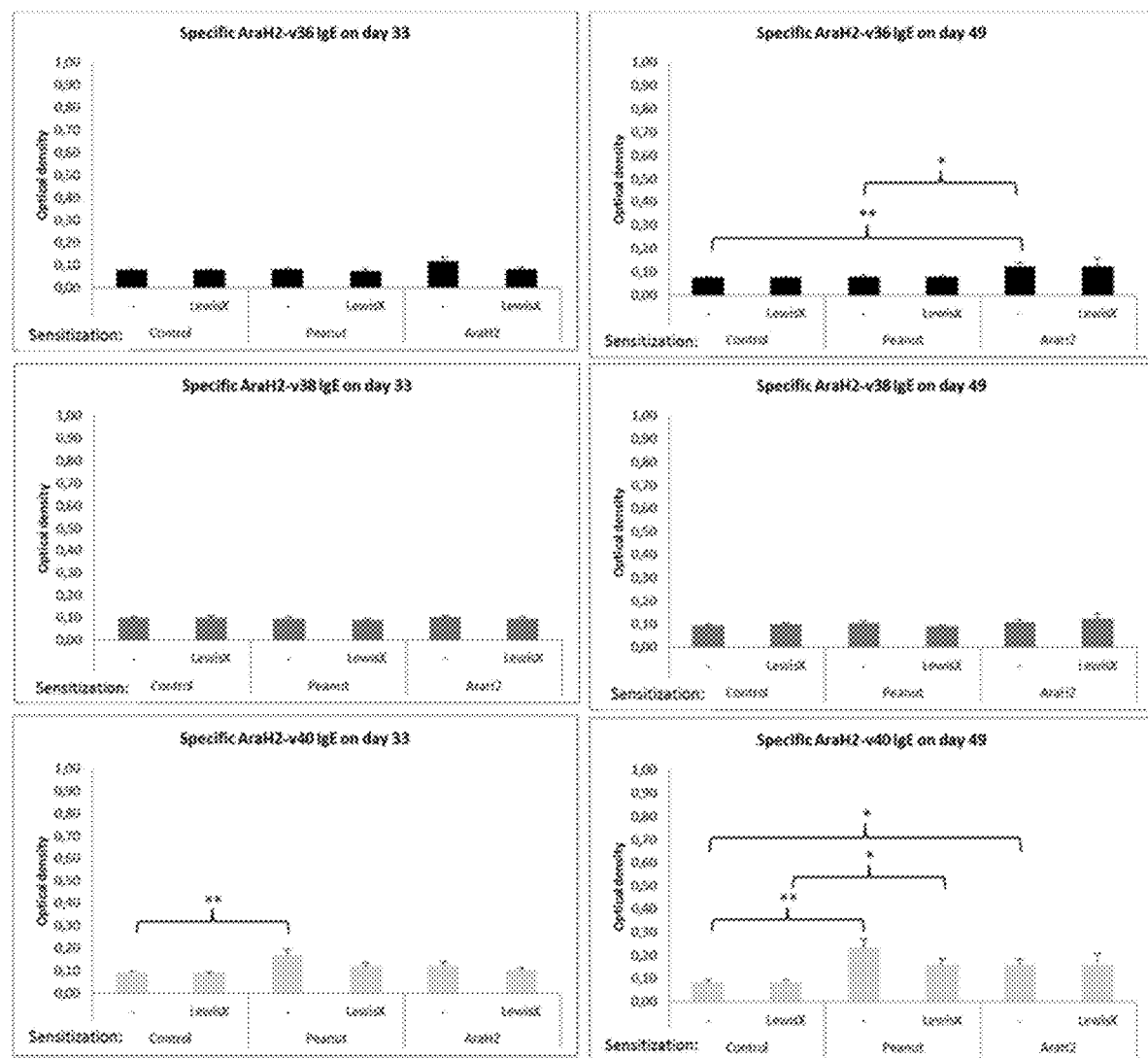

FIG. 9: IgE antibody responses to AraH2-v36 on day 33, on day 49; IgE antibody responses to AraH2-v38 on day 33, on day 49; IgE antibody responses to AraH2-v40 on day 33, on day 49. Mice (n=10 per treatment group, per experiment) received Peanut extract (400 μg protein) or recombinant AraH2 (400 μs) by intra peritoneal injection on days 0, 7, 14 and 36, with or without LewisX adjuvant. Serum samples (days 33 and 49) were analyzed for specific IgE antibody by ELISA. Data are shown as mean (±SEM). Non parametric Wilcoxon test are performed (* $p<0.05$,  $p<0.01$, * $p<0.001$).

Figure 10:
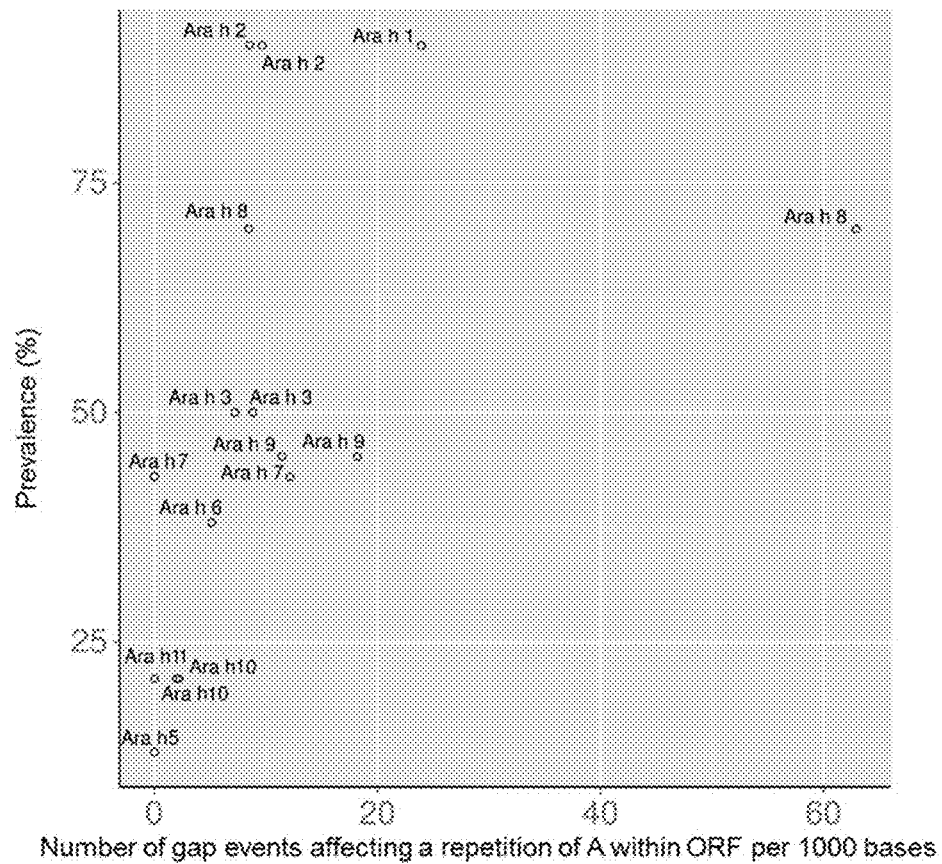

FIG. 10: Correlation between the number of gap events in peanut Ara h 1-3 and Ara h 5-11 transcripts (said gap events affecting a repetition of A within ORF per 1000 bases) and prevalence of the peanut allergens.

Figure 11:
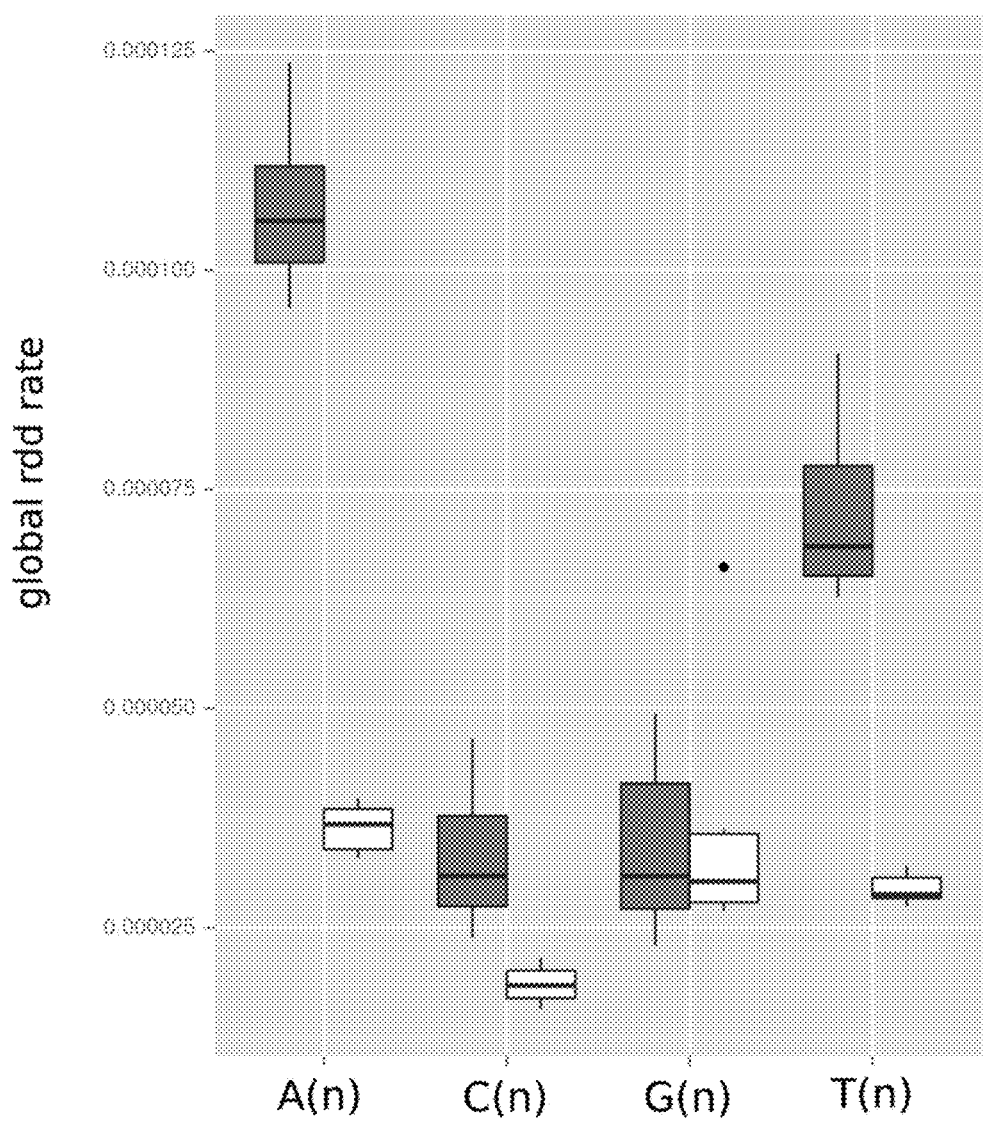

FIG. 11: Comparison of global RDD rate computed on all transcript positions, for peanuts (dark grey) and green beans (white), for deletions affecting repetitions of A, C, G and T bases within the coding regions ORF.

Figure 12:
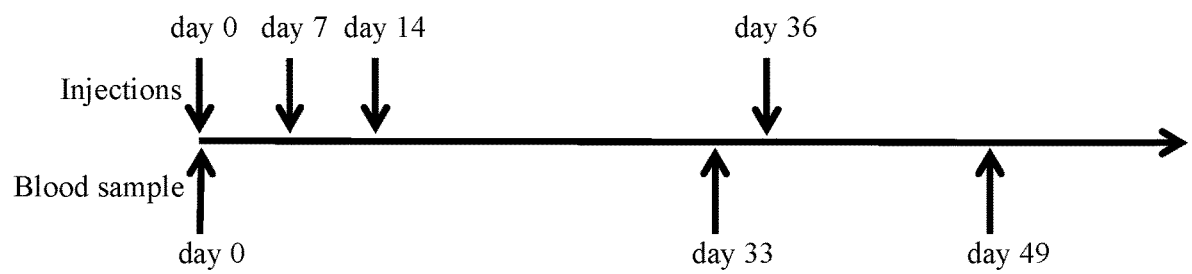

FIG. 12: Diagram of immunization protocol

DETAILED DESCRIPTION OF THE INVENTION

The present invention provides an unified model that explains how any given protein variant, produced by translation of mRNA carrying specific transcription infidelity (TI) event, causes deregulation of natural immunoglobulin specific properties and is at the origin of allergy. More particularly, the present invention defines that known allergens translated from RNA transcribed by a canonical base pairing are unable to elicit modification of natural immunoglobulin properties. On the contrary, their transcription infidelity (TI) variants are clearly able to cause these modifications and trigger allergy.

The invention also provides methods for reducing allergenicity of various food or pharmaceutical compositions or products (such as milk or dairy products, peanut products, peanuts, pharmaceutical preparations, etc.). More particularly, the invention provides methods to remove and/or chemically modify allergy triggers in order to reduce their capacity to elicit change in natural immunoglobulin properties. The invention is exemplified for various forms of allergy (e.g., milk, peanut, mite allergy) and in various mammalian species including human.

Using a murine model of allergy, we surprisingly observed that a protein incapable of inducing IgE production acquired this capacity when it underwent a gap modification resulting from transcription infidelity. This suggests a molecular origin of allergy resulting not from classic allergens but from their protein variants resulting from transcription infidelity. To confirm this hypothesis, we sequenced the RNA of cow's milk and observed the presence of a gap near the main B epitopes of milk proteins such as $\alpha_{S1}$-casein and β-lactoglobulin. We also demonstrated that gap-modified proteins resulting from transcription infidelity had a cationic nature. We thus proceeded to a fractionation of the whey so as to enrich it in TI-produced cationic proteins and then to a comparison of the ability of the enriched and depleted fractions to induce IgE. Remarkably, and unexpectedly, the enriched fraction administered at a dose of 57 μg induces IgE production equivalent to that observed with 1.9 mg of whey protein. In contrast, 57 μg of the depleted fraction does not induce significant IgE production. These results thus show that low abundant variants of proteins can trigger production of IgE which, by extension toward the N-ter portion, also bind the normal protein. The invention thus discloses a molecular mechanism at the origin of allergy and provides new approaches for early diagnosis, treatment and prevention of allergies, and for modulating the immune response.

An object of the invention more particularly resides in a method for reducing allergenicity or immunogenicity of a composition, the method comprising treating the composition to remove proteins resulting from transcription infidelity.

Another object of the invention resides in a method for reducing allergenicity or immunogenicity of a composition, the method comprising treating the composition to remove cationic proteins.

The invention also relates to compositions obtainable by the above methods, as well as the uses thereof.

Within the context of the present invention, the term "immunogenicity" designates for instance the ability of a composition or protein or molecule to induce an immune response in a mammal. This includes for instance the ability to trigger antibody production or a T cell response, or to stimulate or amplify an existing immune response. The term immunogenicity includes, for instance, allergenicity.

Within the context of the present invention, the term "allergenicity" designates the ability of a composition or protein or molecule to induce allergy in a mammal. This includes for instance the ability to trigger allergy, or to stimulate or amplify allergy. In a particular instance, allergenicity designates the ability to induce or stimulate production of IgE in vivo.

"Reducing" allergenicity or immunogenicity indicates a diminution in the allergenicity or immunogenicity, preferably by at least 20%, 30%, 40%, 50% or more. In preferred embodiment, "reducing" allergenicity or immunogenicity designates a reduction by at least 70%, 80%, 90% or more of the allergenicity or immunogenicity of a composition. The term "reducing" also encompasses the suppression of the allergenicity or immunogenicity.

"Removing" a component means at least reducing the amount of said component, preferably by at least 20% as compared to a reference material. In a particular embodiment of the invention, "removing" a component designates a removing of at least 50%, 60%, 70% or more of said component, even more preferably removing of at least 80%, at least 90%, at least 95%, 96%, 97%, 98%, 99%, or more. In a particular embodiment, removing encompasses complete removal of a component, wherein the resulting material is substantially free of said component.

A "protein" designates a molecule comprising amino acids. The term thus designates polypeptides, proteins, or peptides, which may be of natural origin, purified, modified, recombinant, synthetic, etc. Peptides according to this invention typically contain between 3 to 70 amino acids in length, particularly from 5 to 50, from 5 to 40, or from 5 to 30.

A "cationic" protein means, within the context of the present invention, a protein having an isoelectric point of 7.4 or above, preferably of 7.6 or above, 7.8 or above, 8 or above, 8.5 or above, more preferably of 9 or above. A "cationic fraction" of a composition designates a fraction of that composition which contains cationic protein(s).

The term "allergen" designates any molecule that can cause allergy in a mammal. A proteinaceous allergen designates an allergen comprising amino acids in its structure.

The allergen according to the invention may be selected from food, respiratory, contact, or environmental allergens, for example, peanut, egg, milk or mite allergens. Examples of peanut allergens are selected among Ara h 1, Ara h 2, Ara h 3, Ara h 5, Ara h 6, Ara h 7, Ara h 8, Ara h 9, Ara h 10 and Ara h 11 peanut proteins.

The term "transcription infidelity" (TI) refers to a controlled mechanism by which DNA transcription generates RNA molecules with incorrect sequence(s), that subsequently leads to aberrant proteins. Transcription infidelity has been discovered and described by applicant in e.g., WO2008/009751. TI can generate RNAs with one or more differences. Such differences may be e.g., nucleotide substitutions, insertions and/or gaps (deletions), which eventually generate TI proteins with aberrant sequences. TI proteins of particular interest in the context of the present invention are TI gap proteins, which comprise a sequence resulting from suppression of a nucleotide during transcription, leading to proteins with a modified C-terminal end.

As described in example 1 of the present application, the applicant surprisingly observed that a protein normally incapable of inducing an immune response (IgE production) acquired this capability when it underwent a gap modification resulting from transcription infidelity. Thus, the presence of a C-terminal sequence resulting from the gap introduces into this protein a motif giving it an immunogenic (allergenic) nature absent from the normal protein.

To confirm the importance of this mechanism, the applicant carried out a bioinformatics annotation of all transcription infidelity events on the major milk proteins. In order to define precisely the appearance of a TI event, we thus carried out a next-generation sequencing (RNA-Seq) of the RNAs that encode milk proteins. Remarkably, the sequences obtained made it possible to identify exactly the positions of TI in milk proteins, and to know precisely the sequence of TI gap proteins (see example 2). In particular, we identified the following peptides, resulting from TI gaps, and conferring on the corresponding proteins an allergenic nature (Table 1):

| Protein | Peptide Sequence | SEQ ID NO: |
|---|---|---|
| CSN1S1 | LWHLFQKCLERRRSMN | 1 |
| CSN1S2 | LPAFWLLPLQRIRWNMSPPVRNLSSPRKHISR KRIWPLIPARRTFAPHSARKL | 2 |

| Protein | Peptide Sequence | SEQ ID NO: |
|---|---|---|
| CSN2 | EAFQAVRNLLHASIRKLRSFRVRNSSKQRMNS RIKSTPLPRHSL | 3 |
| CSN3 | FWVPRSKTKNNQYAVRKMKDSSVTK | 4 |
| PAEP | KSTCSSAWRTVLSPSKAWPASAWSGPRRWTTR PWRNSTKPSRPCPCTSGCPSTQPSWRSSATSR | 5 |

Continuing our research, we also surprisingly observed that TI proteins resulting from a shift in the reading frame by omission of a base in the RNA sequence (gap) have a higher content in positively-charged basic amino acids and a much lower content in acidic amino acids. This results in proteins having a cationic nature. As an illustration, the isoelectric point of the TI gap proteins identified in milk is given in the table 2 below:

|  | Protein | | | |
|---|---|---|---|---|
|  | Canonical protein MW (Da) | Canonical protein pI | TI protein MW (Da) | TI protein pI |
| CSN1S1 | 22791 | 4.5 | 6418 | 11.2 |
| CSN1S2 | 26019 | 8.6 | 7032 | 13.4 |
| CSN2 | 29221 | 6.6 | 12196 | 11.6 |
| CSN3 | 21269 | 6.7 | 4906 | 11.4 |
| PAEP | 19883 | 4.7 | 19684 | 9.3 |

From this table 2 it can be seen that TI gap proteins having an allergenic nature also have an isoelectric point much higher than that of the canonical proteins. This cationic nature of these proteins is advantageous because it makes it possible in particular to remove them by separation techniques based on isoelectric point. Accordingly, by cation-exchange technique, it is possible to remove proteins having an isoelectric point above a predefined value. Hence, it is possible to produce hypoallergenic (or low immunogenic) compositions by removing the cationic fraction therefrom. In this respect, as confirmed in example 3, milk depleted of the cationic fraction does not induce IgE in vivo, whereas the cationic fraction leads to massive IgE production.

The invention thus makes it possible to design new tools and processes for i) the early and precise molecular diagnosis of all forms of clinically significant allergies, ii) producing compositions having a less immunogenic/allergenic nature by removal of cationic proteins or TI-produced proteins, iii) removing TI-produced cationic proteins from certain food preparations in order to prevent or reduce the onset of allergies, iv) removing the main sources of allergens of certain food preparations intended for subjects identified as at risk, v) producing new adjuvants used to induce antibodies, or vi) defining new desensitization strategies capable of addressing all forms of allergies independently of their specificity.

An aspect of the invention thus relates to methods for reducing allergenicity or immunogenicity of a product by removing TI proteins therefrom, or by removing a cationic fraction therefrom. This method may be applied to various products such as food products (e.g., milk, peanut), cosmetic products, feed, pharmaceutical products, etc.

In this regard, an object of the invention relates to a method for preparing a food product comprising (i) providing a food product preparation, (ii) treating the food product preparation to remove TI proteins therefrom, preferably TI gap proteins, and (iii) optionally formulating the treated food product with one or more suitable excipients.

Another object of the invention relates to a method for preparing a food product comprising (i) providing a food product preparation, (ii) treating the food product preparation to remove cationic proteins therefrom and (iii) optionally formulating the treated food product with one or more suitable excipients.

Another object of the invention relates to a method for preparing a cosmetic product comprising (i) providing a cosmetic agent, (ii) treating the cosmetic agent to remove TI proteins (preferably TI gap proteins) or cationic proteins therefrom and (iii) optionally formulating the treated cosmetic agent with one or more suitable excipients.

Another object of the invention relates to a method for preparing a pharmaceutical agent comprising (i) providing a pharmaceutical agent, (ii) treating the pharmaceutical agent to remove TI proteins (preferably TI gap proteins) or cationic proteins therefrom and (iii) optionally formulating the treated pharmaceutical agent with one or more suitable excipients.

In a preferred embodiment, the above methods comprise removing, from the products or compositions, cationic proteins that result from transcription infidelity, even more particularly from a transcription infidelity gap. More preferably, the method comprises removing at least 50% of cationic proteins having an isoelectric point of 7.4 or more.

In a preferred embodiment, the treated composition contains less than 2% by weight of cationic proteins having an isoelectric point above 8, more preferably less than 1%, even more preferably less than 0.5%, less than 0.2%, or less than 0.1%.

For instance, our analyses show that untreated milk contains approximately 3% by weight of cationic proteins having an isoelectric point above 7.4. The method of the invention preferably removes at least 50% of said proteins, thus leading to a milk preparation containing less than 1.5% by weight of cationic proteins. In a preferred embodiment, the treated milk preparation of the invention contains less than 1%, more preferably less than 0.5%, less than 0.4%, less than 0.3%, less than 0.2%, or even less than 0.1% by weight of cationic proteins having an isoelectric point above 8. The milk may be from any non-human mammal, such as cow, goat or sheep. The milk may also be artificial milk.

In this regard, the invention also relates to a food composition comprising a food product and a suitable excipient, wherein the food product contains less than 1% by weight of cationic proteins having an isoelectric point above 7.4, more preferably less than 0.5%, less than 0.3%, less than 0.2%, or less than 0.1%. In a most particular embodiment, the food product is milk, a cereal or peanut.

The invention also relates to a food composition comprising a food product and a suitable excipient, wherein the food product contains less than 1% by weight of proteins having a sequence resulting from TI gap, more preferably less than 0.5%, less than 0.3%, less than 0.2%, or less than 0.1%. In a most particular embodiment, the food product is milk, a cereal or peanut.

In a particular embodiment, the invention relates to a method for preparing a milk or a dairy product, comprising removing at least one protein comprising a TI gap peptide sequence selected from SEQ ID NO: 1 to 5.

In another particular embodiment, the invention relates to a method for preparing a peanut product, comprising removing at least one protein comprising a TI gap peptide sequence selected from SEQ ID NO: 110 to 120.

In a particular embodiment, the invention relates to a method for preparing a milk or a dairy product, comprising removing at least one protein comprising a sequence selected from SEQ ID NO: 6 to 10.

In another particular embodiment, the invention relates to a method for preparing a peanut product, comprising removing at least one protein comprising a sequence selected from SEQ ID NO: 121 to 131.

The invention also relates to a milk or a dairy product, or a peanut product, comprising less than 0.5% by weight of a protein comprising a TI gap peptide sequence selected from SEQ ID NO: 1 to 5 or SEQ ID NO: 110 to 120, respectively, preferably less than 0.3%, less than 0.2%, or less than 0.1%.

The invention also relates to a milk or a dairy product, or a peanut product, comprising less than 0.5% by weight of a protein comprising a sequence selected from SEQ ID NO: 6 to 10 or SEQ ID NO: 121 to 131, respectively, preferably less than 0.3%, less than 0.2%, or less than 0.1%.

The invention also relates to a cosmetic composition comprising a cosmetic agent and a suitable excipient, wherein the cosmetic agent contains less than 1% by weight of cationic proteins having an isoelectric point above 7.5, more preferably less than 0.5%, less than 0.3%, less than 0.2%, or less than 0.1%.

The invention also relates to a pharmaceutical composition comprising a pharmaceutical agent and a suitable excipient, wherein the pharmaceutical agent contains less than 1% by weight of cationic proteins having an isoelectric point above 7.5, more preferably less than 0.5%, less than 0.3%, less than 0.2%, or less than 0.1%.

The invention may also be used to produce immunogenic preparations having reduced allergenicity, suitable for desensitization of allergic subjects. In this regard, an object of the invention also relates to a method for preparing an allergen composition comprising (i) providing a proteinaceous allergen preparation, (ii) treating the preparation to remove cationic proteins therefrom and (iii) optionally formulating the preparation with one or more suitable excipients. Such treated preparations retain immunogenicity and may be used to induce tolerance in allergic subjects. However, such treated preparations have by themselves a reduced allergenicity and are less likely to induce undesirable side effects. Such method may be used with any allergen preparation, such as respiratory, contact, food, or environmental allergens (i.e., peanut, egg, milk, mite allergens, etc.). The allergen may be a recombinant proteinaceous allergen or a partially purified natural allergen.

The invention thus also relates to a composition comprising a proteinaceous allergen and a suitable excipient, wherein the proteinaceous allergen contains less than 2% by weight of cationic proteins, more preferably less than 1%, less than 0.5%, less than 0.2%, or less than 0.1%.

The invention also concerns a method of treating a subject allergic to an allergen to desensitize said subject to said allergen, comprising administering to the subject an effective amount of a composition as defined above.

The invention may also be used to produce pharmaceutical preparations having reduced allergenicity or immunogenicity. In this regard, an object of the invention also relates to a method for preparing a pharmaceutical composition comprising (i) providing a proteinaceous drug preparation, (ii) treating the preparation to remove cationic proteins therefrom and (iii) optionally formulating the preparation with one or more suitable excipients. Such treated preparations retain pharmaceutical activity and may be used to treat subjects. However, such treated preparations have by themselves a reduced allergenicity/immunogenicity and are less likely to induce undesirable side effects. Such method may be used with any proteinaceous drug preparation, such as a drug, hormone, cytokine, enzyme, growth factor, etc.

As previously mentioned, removal of a cationic fraction or protein may be accomplished by techniques known per se in the art. In particular, cationic proteins may be removed by separation using cation exchange techniques. Examples of suitable material for cationic exchange include, for instance, HiTrap SP or CM, HiLoad SP or CM, or Bulk SP or CM. In a particular method, the process comprises (i) adjusting pH to a desired value (typically between 7.4 and 9) and (ii) subjecting the preparation to cationic exchange wherein essentially all material having an isoelectric point above the adjusted pH value is removed. In a particular embodiment, the method thus comprises (i) adjusting a solution of the composition to have a pH comprised between 7.4 and 9, preferably between 7.4 and 8.5, (ii) subjecting the solution to cation exchange chromatography, and (iii) recovering the eluate.

Alternatively, or in addition to the cationic exchange, the method may comprise a step of affinity chromatography using e.g., antibodies directed against transcription infidelity proteins. Such antibodies may be produced by procedures generally known in the art. For example, polyclonal antibodies may be produced by injecting TI proteins or a TI peptide thereof, or a cationic fraction of a biological sample, alone or coupled to a suitable carrier or adjuvant into a non-human animal. After an appropriate period, the animal is bled, sera recovered and purified by techniques known in the art (Paul, W. E. "Fundamental Immunology" Second Ed. Raven Press, NY, p. 176, 1989; Harlow et al. "Antibodies: A laboratory Manual", CSH Press, 1988; Ward et al (Nature 341 (1989) 544).

The present invention also relates to a method for reducing immunogenicity or allergenicity of a peanut, the method comprising reducing the transcription infidelity rate in one or more peanut proteins selected from Ara h 1, Ara h 2, Ara h 3, Ara h 5, Ara 17 h 6, Ara h 7, Ara h 8, Ara h 9, Ara h 10 and Ara h 11. Such a method may comprise a step of integrating a synthetic DNA nucleotide sequence in a peanut grain, seed, or plant, wherein said synthetic sequence limits the transcription infidelity (TI) rate which results in TI gaps. Such a method may alternatively comprise a step of correcting and/or genetically modifying a DNA sequence in order to limit transcription infidelity rate and to avoid generation of TI peanut protein variants, by using various known gene engineering techniques such as Clustered Regularly Interspaced Short Palindromic Repeats (CRISPR) technology. In a particular embodiment, the invention relates to a transgenic peanut plant or a seed or grain thereof, comprising a modified Ara h protein gene with reduced transcription infidelity rate. The modified gene preferably comprises a modified T or A repeat domain.

The invention also allows the development of methods for detecting allergy in a subject. In this respect, the invention thus also concerns a method for detecting a subject having predisposition to allergy, comprising measuring in a sample from said subject the level of IgE directed against proteins having a sequence resulting from a transcription infidelity, wherein a difference in said level as compared to a control value indicates a subject having predisposition to allergy.

The invention also allows the stimulation of an immune response. Indeed, the identified TI proteins or peptides show increased immunogenicity and may be used to induce or stimulate an immune response, for instance as adjuvants.

The invention thus also relates to a cationic protein or peptide comprising a sequence resulting from transcription infidelity, for use as an adjuvant to stimulate an immune response in a mammal, particularly to stimulate antibody production. The invention is particularly suited to stimulate or induce IgE production in a mammal. The mammal may be a non-human or a human mammal.

The invention also concerns a method of inducing or stimulating antibody production in a mammal, such as a human, comprising administering to the mammal a cationic protein or peptide having a sequence resulting from transcription infidelity.

The invention also concerns a vaccine composition comprising an immunogen and a protein or peptide having a sequence resulting from transcription infidelity.

A further object of the invention relates to a method for producing antibodies comprising (i) administering to a non-human mammal a cationic protein or peptide resulting from transcription infidelity, (ii) collecting antibodies produced and (iii) optionally deriving monoclonal and/or humanized antibodies from said collected antibodies.

It is also an object of the invention to provide methods of making anti-IgE antibodies, comprising (i) administering to a non-human mammal a cationic protein or peptide resulting from transcription infidelity under conditions allowing induction of antibody production, (ii) collecting antibodies produced and (iii) selecting antibodies that bind Fc receptor.

The invention also relates to a protein or peptide comprising a sequence selected from SEQ ID NO: 1-5 or SEQ ID NO: 74 to 109 or SEQ ID NO: 110 to 120, a fragment thereof, and to a composition comprising such a protein or peptide. The peptides, or fragments thereof, of the invention preferably have a length below 70 amino acid residues, even more preferably below 60, below 50, 40, below 35, or below 30. Particular peptides of the invention consist of anyone of SEQ ID NO: 1-5 or a fragment thereof containing at least 10 consecutive residues thereof. The fragments preferably shall retain an immunogenicity or allergenicity. The invention also relates to a protein comprising any one of SEQ ID NOs: 6-10 or SEQ ID NO: 16 to 51 or SEQ ID NO: 121 to 131.

Further aspects and advantages of the invention will be disclosed in the following experimental section, which is illustrative of the claims.

EXAMPLES

Example 1: Proof of Concept of the Molecular Origin of Allergy

The applicant has an approved animal facility for experimentation on mice and developed and published two preclinical murine models of allergy, one with peanut (Proust et al., 2008, Int Arch Allergy Immunol 146, 212-218), the other with cow's milk (Proust et al., 2009, European Annals of Allergy and Clinical Immunology 41(3): 85-94).

The hypothesis of the molecular origin of allergy was tested in the milk allergy model in which 6 successive intragastric administrations of proteins (at a rate of one per week) induce IgE production if the proteins are allergenic. Two different peptides were selected to test the hypothesis: a normal peptide not having undergone a TI event (non-TI peptide), and a TI peptide (resulting from a transcription infidelity event). These two peptides were administered to mice for 6 weeks and IgE production was followed over time (FIG. 1).

As shown in FIG. 1, IgE synthesis is massive when the mice are exposed to the TI peptide, whereas it is negligible with non-TI peptide. Using a single intraperitoneal administration of TI and non-TI peptides, the same results were obtained (FIG. 2).

These two experiments show that TI peptides, by their specific physicochemical properties, are at the origin of IgE production, in both intragastric and intraperitoneal administration. This example illustrates that the large protein heterogeneity generated by transcription infidelity is a source of allergy triggers.

Example 2: Analysis of Milk Proteins

In order to obtain RNAs that encode milk proteins, we used the epithelial cells present in milk. Indeed, these cells are a good alternative for studying expression of RNAs expressed in bovine mammary gland (Canovas et al., 2014, Scientific Reports 4:5297). We obtained from a farm the milk of an untreated Prim'Holstein cow. Epithelial cells were purified from this milk.

From these cells, total RNA was extracted. The integrity of these RNAs was confirmed (RNA Integrity Number (RIN)=7.6) before preparing the libraries for Illumina next-generation sequencing. This RIN value is compatible with the preparation of Illumina libraries.

We have been able to confirm that the mean quality index for the two libraries is above 30 (library 1: 35.6 and library 2: 35.6) and that for the two libraries 94% of the reads have a quality index over 30. The quality of the sequences is compatible with the standards required for our analyses.

In order to define the positions where TI occurs, the reads obtained were aligned against the *Bos taurus* reference genome version UMD_3.1.1 (see Worldwide Website: ncbi.nlm.nih.gov/genome/82) and against the transcriptome constructed from the genome.

First, we studied the type of TI difference that leads to the most important modifications of the sequence of the protein encoded by the RNA. This is a deletion, also termed "TI gap" (FIG. 3).

When a TI gap appears in an RNA sequence, the protein sequence is highly modified. Indeed, the deletion of a base causes a shift of the reading frame, itself having dramatic consequences on the protein sequence located downstream of the event. Remarkably, we discovered that the carboxy-terminal part of the protein resulting from transcription infidelity (deletion) is enriched in basic amino acids and impoverished in acidic amino acids. Hence, the proteins resulting from TI have a cationic nature.

As proof of concept, we analyzed the sequences of the major milk allergens identified in the Allergome database (see Worldwide Website: allergome.org/). The allergens are presented in Table 3 below.

TABLE 3

List of major allergens in cow's milk.

| Gene | description | chromosome |
|---|---|---|
| ALB | albumin | 6 |
| CSN1S1 | casein alpha s1 | 6 |
| CSN1S2 | casein alpha-S2 | 6 |
| CSN2 | casein beta | 6 |
| CSN3 | casein kappa | 6 |
| LALBA | lactalbumin, alpha- | 5 |
| LPO | lactoperoxidase | 19 |
| LTF | lactotransferrin | 22 |
| PAEP | beta lactoglobuline | 11 |

With the sequence data, we can estimate the expression of these genes in cells isolated from milk. To that end, we calculated the number of reads aligned to each gene (RPKM: Reads Per Kilobase per Million mapped reads) (Mortazavi et al., 2008, Nature Methods, 5(7): 621-28).

The results are shown in Table 4 below:

TABLE 4

Expression of genes encoding major allergens in cells isolated from cow's milk. Expression is measured in the 2 libraries in RPKM.

| Gene | RPKM moyen | |
| --- | --- | --- |
|  | Librairie 1 | Librairie 2 |
| ALB | 0.02 | 0.01 |
| CSN1S1 | 131.91 | 128.72 |
| CSN1S2 | 71.49 | 70.44 |
| CSN2 | 153.00 | 154.07 |
| CSN3 | 155.89 | 159.23 |
| LALBA | 39.12 | 43.29 |
| LPO | 0.13 | 0.11 |
| LTF | 10.63 | 10.91 |
| PAEP | 116.38 | 122.29 |

We selected the TI gap events that occur with high frequencies at the same positions in the two libraries. Similarly, the TI gaps that encode proteins having sequences the most enriched in basic amino acids were selected. We were thus able to identify the following TI proteins in milk (SEQ ID NOs: 6-10): the underlined part corresponds to the sequence of the TI gap peptide. For comparison, the sequences of the canonical proteins are provided (SEQ ID NOs: 11-15):

CSN1S1
(SEQ ID NO: 11)
MKLLILTCLVAVALARPKHPIKHQGLPQEVLNENLLRFFVAPFPEVFGKE

KVNELSKDIGSESTEDQAMEDIKQMEAESISSSEEIVPNSVEQKHIQKED

VPSERYLGYLEIVPNSAEERLHSMKEGIHAQQKEPMIGVNQELAYFYPEL

FRQFYQLDAYPSGAWYYVPLGTQYTDAPSFSDIPNPIGSENSEKTTMPLW

CSN1S1_TI
(SEQ ID NO: 6)
MKLLILTCLVAVALARPKHPIKHQGLPQEVLNENLLRF<u>LWHLFQKCLERR</u>

<u>RSMN</u>

CSN1S2
(SEQ ID NO: 12)
MKFFIFTCLLAVALAKNTMEHVSSSEESIISQETYKQEKNMAINPSKENL

CSTFCKEVVRNANEEEYSIGSSSEESAEVATEEVKITVDDKHYQKALNEI

NQFYQKFPQYLQYLYQGPIVLNPWDQVKRNAVPITPTLNREQLSTSEENS

KKTVDMESTEVFTKKTKLTEEEKNRLNFLKKISQRYQKFALPQYLKTVYQ

HQKAMKPWIQPKTKVIPYVRYL

CSN1S2_TI
(SEQ ID NO: 7)
MKFF<u>ILPAFWLLPLQRIRWNMSPPVRNLSSPRKHISRKRIWPLIPARRTF</u>

<u>APHSARKL</u>

CSN2
(SEQ ID NO: 13)
MPLNTIYKQPQNQIIIHSAPPSLLVLYFGKKELRAMKVLILACLVALALA

RELEELNVPGEIVESLSSSEESITRINKKIEKFQSEEQQQTEDELQDKIH

PFAQTQSLVYPFPGPIHNSLPQNIPPLTQTPVVVPPFLQPEVMGVSKVKE

AMAPKHKEMPFPKYPVEPFTERQSLTLTDVENLHLPLPLLQSWMHQPHQP

LPPTVMFPPQSVLSLSQSKVLPVPQKAVPYPQRDMPIQAFLLYQEPVLGP

VRGPFPIIV

CSN2_TI
(SEQ ID NO: 8)
MPLNTIYKQPQNQIIIHSAPPSLLVLYFGKKELRAMKVLILACLVALALA

RELEELNVPGEIV<u>EAFQAVRNLLHASIRKLRSFRVRNSSKQRMNSRIKST</u>

<u>PLPRHSL</u>

CSN3
(SEQ ID NO: 14)
MMKSFFLVVTILALTLPFLGAQEQNQEQPIRCEKDERFFSDKIAKYIPIQ

YVLSRYPSYGLNYYQQKPVALINNQFLPYPYYAKPAAVRSPAQILQWQVL

SNTVPAKSCQAQPTTMARHPHPHLSFMAIPPKKNQDKTEIPTINTIASGE

PTSTPTTEAVESTVATLEDSPEVIESPPEINTVQVTSTAV

CSN3_TI
(SEQ ID NO: 9)
MMKSFFLVVTILALTLP<u>FWVPRSKTKNNQYAVRKMKDSSVTK</u>

PAEP
(SEQ ID NO: 15)
MKCLLLALALTCGAQALIVTQTMKGLDIQKVAGTWYSLAMAASDISLLDA

QSAPLRVYVEELKPTPEGDLEILLQKWENGECAQKKIIAEKTKIPAVFKI

DALNENKVLVLDTDYKKYLLFCMENSAEPEQSLACQCLVRTPEVDDEALE

KFDKALKALPMHIRLSFNPTQLEEQCHI

PAEP_TI
(SEQ ID NO: 10)
MKCLLLALALTCGAQALIVTQTMKGLDIQKVAGTWYSLAMAASDISLLDA

QSAPLRVYVEELKPTPEGDLEILLQKWENGECAQKKIIAEKTKIPAVFKI

DALNENKVLVLDTDY<u>KSTCSSAWRTVLSPSKAWPASAWSGPRRWTTRPWR</u>

<u>NSTKPSRPCPCTSGCPSTQPSWRSSATSR</u>

We analyzed the whole genome and confirmed that the disclosed peptides cannot be produced from another sequence in the cow transcriptome or genome.

The peptides thus identified, and the full-length proteins that contain them, are milk allergens. Removing these proteins from milk makes it possible to obtain a hypoallergenic milk. Furthermore, these proteins and peptides can also be used as adjuvants to stimulate an immune response in mammals, in particular to stimulate antibody production.

Example 3: Production of a Hypoallergenic Milk

The physicochemical properties of TI peptides and their importance in IgE production led us to develop a hypoallergenic infant formula that lacks these proteins.

For this purpose, we carried out a chromatographic fractionation of milk so as to produce two fractions: one enriched in TI proteins and the other depleted of TI proteins.

The initial rough material is in solid phase (whey powder).

The material is composed of all soluble native milk proteins except caseins.

The material is dissolved in a buffered solution adjusted to the desired value (i.e. pH 7.4). The remaining insoluble parts are then removed by filtration or by centrifugation. The material is injected on a cationic exchange chromatography column (HiTrap SP FF) using the Akta Xpress chromatographic system (GE Healthcare Lifesciences). The separation is based on the isoelectric point of each protein. The proteins whose isoelectric points are higher than pH 7.4 (i.e. the cationic fraction) will bind to the resin, and the proteins whose isoelectric points are equal or lower than pH 7.4 (i.e. the non-charged and anionic fraction) will elute in the flow-through (FT). Once the FT is collected, the column is washed. The cationic fraction (which contains proteins with isoelectric points higher than pH 7.4) is then eluted from the column and collected by injecting a buffered solution of pH 7.4.

Therefore, the FT corresponds to the initial material depleted from its cationic fraction and is called Product no 1. Product no 1's main property is that 95% of cationic fraction which triggers allergy have been removed. Product no 1 is thus obtainable by a one-step physicochemical separation and is industrially compatible.

If suitable, a further treatment step may be performed to remove essentially all TI proteins. Such further treatment is an affinity binding step that uses Transcription Infidelity AntiBodies (TIAB). More particularly, the TIABs are obtained from bovine sera. Briefly, the bovine serum is thermo-activated and then total IgGs are purified by affinity chromatography (based on Protein G). Product no 1 is incubated with the bovine TIABs and then submitted to an affinity chromatography based on Protein G. The total IgGs, including the ones complexed with proteins originating from Transcription Infidelity, bind to the resin and the FT contains a material totally depleted of allergy triggers (called Product no 2).

The fractions produced were administered via intragastric route to mice according to the protocol shown in FIG. 1 and IgE production was followed over time (FIG. 4).

The results presented in FIG. 4 show that mice exposed to the fraction enriched in TI proteins produce IgE in a massive way, whereas mice exposed to the depleted fraction produce little or no IgE. We can thereby conclude that 1) TI proteins in milk are indeed at the origin of milk's allergenicity and 2) the depleted fraction is much less allergenic than the enriched fraction. The invention thus makes it possible to produce a hypoallergenic milk.

Example 4: Analysis of Mite Allergens

This analysis is based on the localization of TI gap events in mite allergens and non-allergens. We have surprisingly observed that TI deletion events are mainly present in the coding regions (ORF-IN) of the transcripts coding for mite allergens whereas TI deletion events are mainly outside the coding regions (ORF-OUT) in the case of transcripts which do not code for mite allergens.

In order to carry out this study, we have analyzed RNA sequences of *Dermatophagoides farina* by Illumina next-generation sequencing. We formed two groups of sequences: (1) Transcripts known as allergens and (2) Transcripts which are not allergens. The two groups have similar characteristics of sequence (such as frequency of four bases, mean coverage at each position, length of covered transcripts, exons number) as summarized in Table 5.

TABLE 5

Comparison of transcripts coding allergens versus transcripts coding non-allergens (i.e., proteins never described as allergens). Each group includes 35 transcripts. Evaluated parameters show that the two groups are similar.

|  | Allergen | Non allergen |
|---|---|---|
| Number of transcripts | 35 | 35 |
| A frequency | 33.2 (±3.1) | 34.1 (±2.6) |
| T frequency | 29.8 (±2.5) | 32.11 (±3.1) |
| C frequency | 18 (±2.9) | 17 (±2.1) |
| G frequency | 18.9 (±2.3) | 16.8 (±2.3) |
| Length of covered transcripts | 666.5 (±446.3) | 674 (±461.9) |
| Mean coverage at each position | 61.8 (±62.1) | 64 (±67.9) |
| Number of exons | 3 (±1.6) | 3 (±1.3) |

We have identified the events of transcription infidelity (TI) in these transcripts and we have compared the two groups, namely the allergens and non-allergens. Our results show that TI deletions affecting the sequences of allergens are mainly located within the coding regions, i.e. in the ORF, contrary to TI deletion events affecting the sequences of non-allergens, which are mainly found in non-coding regions (see FIG. 5).

We have also analyzed a ratio between the number of deletions in the coding sequences and the number of deletions in the non-coding sequences, and we have observed that the deletions in the coding sequences of allergens preferentially affect repetitions of A or T base (see FIG. 6).

The repetitions of affected A bases are mainly followed by T bases and the repetitions of affected T bases are followed G bases; these two types of events, when they are located in the ORF, are thus very specific to allergens. These events affect a considerable part of transcripts, from about 0.2% to 10%, more preferably from 0.2% to 5%.

We were able to identify the following TI allergenic proteins for all TI gaps events in *Dermatophagoides farinae*: SEQ ID NO: 16-51. The underlined parts of the sequences correspond to the sequences of the TI gap peptides also listed below as SEQ ID NO: 74 to 109. For comparison, the sequences of the canonical proteins are also provided (SEQ ID NO: 52-73).

Der f 1_iso1

(SEQ ID NO: 52)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QIYPPDVKQIREALTQTHTAIAVIIGIKDLRAFQHYDGRTIIQHDNGYQPNYHAV
NIVGYGSTQGVDYWIVRNSWDTTWGDSGYGYFQAGNNLMMIEQYPYVVIM

Der f 1_iso1_TI (SEQ ID NO: 16)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN

-continued

VPSELDLRSLRTVTPIRMQGGCGSCWAFSGVAATESA<u>FWPTVTRLWIFLNRNSS</u>
<u>IAHLNTDVTAIQYQEASNTSNKMVSLKKEAIHTLHENNNADDQIRNITVSQTTA</u>
<u>KFIHQM</u>

Der f 1_iso1_TI (SEQ ID NO: 17)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QIYPPDVKQIREALTQTHTAIAVIIGIKDLRA<u>SNIMMDEQSFNMTMVINQTIMPST</u>
<u>LSVTEVHKASIIGSYETVGIQPGVIADTDISKPETTS</u>

Der f 1_iso1_TI (SEQ ID NO: 18)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QIYPPDVKQIREALTQTHTAIAVIIGIKDLRAFQHYDGRTIIQHE<u>MVINQTIMPSTL</u>
<u>SVTEVHKASIIGSYETVGIQPGVIADTDISKPETTS</u>

Der f 1_iso1_TI (SEQ ID NO: 19)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QIYPPDVKQIREALTQTHTAIAVIIGIKDLRAFQHYDGRTIIQHDNGYQPNYHAV
NIVGYGSTQGVD<u>IGSYETVGIQPGVIADTDISKPETTS</u>

Der f 1_iso2 (SEQ ID NO: 53)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QIYPPDVKQIREALTQTHTAIAVIIGIKDLRAFQHYDGRTIIQHDNGYQPNYHAV
NIVGYGSTQGVDYWIVRNSWDTTWGDSGYGYFQAGNNLMMIEQYPYVVIM

Der f 1_iso2_TI (SEQ ID NO: 20)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESA<u>FWPTVTRLWIFLNRNSS</u>
<u>IAHLNTDVTAIQYQEASNTSNKMVSLKKEAIHTLHENNNADDQIRNITVSQTTA</u>
<u>KFIHQM</u>

Der f 1_iso2_TI (SEQ ID NO: 21)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QIYPPDVKQIREALTQTHTAIAVIIGIKDLRA<u>SNIMMDEQSFNMTMVINQTIMPST</u>
<u>LSVTEVHKASIIGSYETVGIQPGVIADTDISKPETTS</u>

Der f 1_iso2_TI (SEQ ID NO: 22)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QTYPPDVKQIREALTQTHTAIAVIIGIKDLRAFQHYDGRTIIQHE<u>MVINQTIMPSTL</u>
<u>SVTEVHKASIIGSYETVGIQPGVIADTDISKPETTS</u>

Der f 1_iso2_TI (SEQ ID NO: 23)

MKFVLAIASLLVLSTVYARPASIKTFEEFKKAFNKNYATVEEEEVARKNFLESL
KYVEANKGAINHLSDLSLDEFKNRYLMSAEAFEQLKTQFDLNAETSACRINSVN
VPSELDLRSLRTVTPIRMQGGCGSCWAFSGVAATESAYLAYRNTSLDLSEQELV
DCASQHGCHGDTIPRGIEYIQQNGVVEERSYPYVAREQQCRRPNSQHYGISNYC
QTYPPDVKQIREALTQTHTAIAVIIGIKDLRAFQHYDGRTIIQHDNGYQPNYHAV
NIVGYGSTQGVD<u>IGSYETVGIQPGVIADTDISKPETTS</u>

Der f 23_iso1 (SEQ ID NO: 54)

MKFNITIAFVSLAILIHSSYADIDHFDNDDQNSSTSRPDDDPTTMIDVQTTTVQPS
SMPTTSESQSTVKPTTTTVKPSPTTVKLTTTTVKPTTTTVKPTTTTVKPSPTTVKP
TTTTVKPSPTTTTTTTEQPEDEFECPTRFGYFADPKDPCKFYICSNWEAIHKSCP
GNTRWNEKELTCT

Der f 23_iso1_TI (SEQ ID NO: 24)

MKFNITIAFVSLAILIHSSYADIDHFDNDDQNSSTSRPDDDPTTMIDVQTTTVQPS
SMPTTTSESQSTVKPTTTTVKPSPTTVKLTTTTVKPTTTTVKPTTTTVKPSPTTVKP
TTTTVKPSPTTTTTTTTEQPEDEFECPTRFGYFADPKDPCKFIFVQIGKLYIKVVQ
VIQDGMKKN

Der f 11_iso1

(SEQ ID NO: 55)

MSARTAKYMYRSSGAGASGDISVEYGTDLGALTRLEDKIRLLSDDLESEREMR
QRIEREKAELQIQVMSLGERLEEAEGSSESVTEMNKKRDSELAKLRKLLEDVHI
ESEETAHHLRQKHQAAIQEMQDQLDQLQKAKNKSDKEKQKFQAEVFELLAQL
ETANKEKLTALKNVEKLEYTVHELNIKIEEINRTVIELTSHKQRLSQENTELIKEV
HEVKLQLDNANHLKTQIAQQLEDTRHRLEEEERKRASLENHAHTLEVELESLK
VQLDEESEARLELERQLTKANGDAASWKSKYEAELQAHADEVEELRRKMAQK
ISEYEEQLEALLNKCSSLEKQKSRLQSEVEVLIMDLEKATAHAQQLEKRVAQLE
KINLDLKNKLEEVTMLMEQAQKELRVKIAELQKLQHEYEKLRDQRDQLAREN
KKLTDDLAEAKSQLNDAHRRIHEQEIEIKRLENERDELSAAYKEAETLRKQEEA
KNQRLIAELAQVRHDYEKRLAQKDEEIEALRKQYQIEIEQLNMRLAEAEAKLKT
EIARLKKKYQAQITELELSLDAANKANIDLQKTIKKQALQITSELQAHYDEVHR
QLQQAVDQLGVTQRRCQALQAELEEMRIALEQANRAKRQAEQLHEEAVVRVN
ELTTINVNLASAKSKLESEFSALQADYDEVHKELRISDERVQKLTIELKSTKDLLI
EEQERLVKLETVKKSLEQEVRTLHVRIEEVEANALAGGKRVIAKLESRIRDVETE
VEEERRRHAETDKMLRKKDHRVKELLLQNEEDHKQIQLLQEMTDKLNEKVKV
YKRQMQEQEGMSQQNLTRVRRFQRELEAAEDRADQAESNLSFIRAKHRSWVT
TSQVPGGTRQVFTTQEETTNY

Der f 11_iso1_TI (SEQ ID NO: 25)

MSARTAKYMYRSSGAGASGDISVEYGTDLGALTRLEDKIRLLSDDLESEREMR
QRIEREKAELQIQVMSLGERLEEAEGSSESVTEMNKKRDSELAKLRKLLEDVHI
ESEETAHHLRQKHQAAIQEMQDQLDQLQKAKNKSDKEKQKFQAEVFELLAQL
ETANKEKLTALKNVEKLEYTVHELNIKIEEINRTVIELTSHKQRLSQENTELIKEV
HEVKLQLDNANHLKTQIAQQLEDTRHRLEEEERKRASLENHAHTLEVELESLK
VQLDEESEARLELERQLTKANGDAASWKSKYEAELQAHADEVEELRRKMAQK
ISEYEEQLEALLNKCSSLEKQKSRLQSEVEVLIMDLEKATAHAQQLEKRVAQLE
KINLDLKNKLEEVTMLMEQAQKELRVKIAELQKLQHEYENYVINVINWHVKTR
NLQTILPKLNHN

Der f 11_iso1_TI (SEQ ID NO: 26)

MSARTAKYMYRSSGAGASGDISVEYGTDLGALTRLEDKIRLLSDDLESEREMR
QRIEREKAELQIQVMSLGERLEEAEGSSESVTEMNKKRDSELAKLRKLLEDVHI
ESEETAHHLRQKHQAAIQEMQDQLDQLQKAKNKSDKEKQKFQAEVFELLAQL
ETANKEKLTALKNVEKLEYTVHELNIKIEEINRTVIELTSHKQRLSQENTELIKEV
HEVKLQLDNANHLKTQIAQQLEDTRHRLEEEERKRASLENHAHTLEVELESLK
VQLDEESEARLELERQLTKANGDAASWKSKYEAELQAHADEVEELRRKMAQK
ISEYEEQLEALLNKCSSLEKQKSRLQSEVEVLIMDLEKATAHAQQLEKRVAQLE
KINLDLKNKLEEVTMLMEQAQKELRVKIAELQKLQHEYEKLRDQRDQLAREN
KKLTDDLAEAKSQLNDAHRRIHEQEIEIKRLENERDELSAAYKEAETLRKQEEA
KNQRLIAELAQVRHDYEKRLAQKDEEIEALRKQYQIEIEQLNMRLAEAEAKLKT
EIARLKKKYQAQITELELSLDAANKANIDLQKTIKKQALQITSELQAHYDEVHR
QLQQAVDQLGVTQRRCQALQAELEEMRIALEQANRAKRQAEQLHEEAVVRVN
ELTTINVNLASAKSKLESEFSALQADTMKYIKNLEFLMNEYRNLQLNSNLLKIC

Der f 15_iso1

(SEQ ID NO: 56)

MKTIYAILSIMACIGLMNASIKRDHNDYSKNPMRIVCYVGTWSVYHKVDPYTIE
DIDPFKCTHLMYGFAKIDEYKYTIQVFDPYQDDNHNSWEKRGYERFNNLRLKN
PELTTMISLGGWYEGSEKYSDMAANPTYRQQFIQSVLDFLQEYKFDGLDLDWE
YPGSRLGNPKIDKQNYLALVRELKDAFEPHGYLLTAAVSPGKDKIDRAYDIKEL
NKLFDWMNVMTYDYHGGWENFYGHNAPLYKRPDETDELHTYFNVNYTMHY
YLNNGATRDKLVMGVPFYGRAWSIEDRSKLKLGDPAKGMSPPGFISGEEGVLS
YIELCQLFQKEEWHIQYDEYYNAPYGYNDKIWVGYDDLASISCKLAFLKELGV
SGVIVWSLENDDFKGHCGPKNPLLNKVHNMINGDEKNSFECILGPSTTTPTTT
PTTTPTSPTTPTPSPTTPTTTPSPTTPTPSPTTPTTTPSPTTPTPTTPTPTPTTSTPSP
TTTEHTSETPKYTTYVDGHLIKCYKEGDIPHPTNIHKYLVCEFVNGGWWVHIMP
CPPGTIWCQEKLTCIGE

Der f 15_iso1_TI (SEQ ID NO: 27)

MKTIYAILSIMACIGLMNASIKRDHNDYSKNPMRIVCYVGTWSVYHKVDPYTIE
DIDPFKCTHLMYGFAKIDEYKYTIQVFDPYQDDNHNSWEKRGYERFNNLRLKN
PELTTMISLGGWYEGSEKYSDMAANPTYRQQFIQSVLDFLQEYKFDGLDWIGSI
LDLDWVTRKSTNKTIWLWLENLKTLLNLMATC

Der f 32_iso1

(SEQ ID NO: 57)

MSTTNYSVDHRGSFNSLDYRIYFKDNSNGKIISPWHDIPLFVDKSAKHYNMVVE
IPRWTNEKMEIATAEPMSPIKQDIKKGALRYVKNVFPHKGYIWNYGAFPQTWE

-continued
```
NPNHIDQDTKTKGDNDPIDVIEIGSRVAKRGDVVPVKILGTIALIDEGETDWKIIA
IDTRDELASQMNNVDDVEKLLPGLLRATVEWFKIYKIPDGKPANKFAFNGEAK
DREFAEKIVEETHQYWQEMMENKSGEHKLDLKNVTLGNSFSINDEQAKQFLET
RPSSDAVEPTPIADQVAIDKWHEIVKLI
```

Der f 32_iso1_TI                                                (SEQ ID NO: 28)

```
MSTTNYSVDHRGSFNSLDYRIYFKDNSNGKIISPWHDIPLFVDKSAKHYNMVVE
IPRWTNEKMEIATAEPMSPIKQDIKKGALRYVKNVFPHKGYIWNYGAFPQTWE
NPNHIDQDTKTKGDNDPIDVIEIGSRVAKRGDVVPVKILGTIALIDEGETDWKIIA
IDTRDELASQMNNVDDVEKLLPGLLRATVEWFKIYKIPDGKPANKFAFNGEAK
DRELLKKSLKKHINIGKK
```

Der f 25_iso1                                                   (SEQ ID NO: 58)

```
MVRKFFVGGNWKMNGSRATNEDLIKTLSNGPLDPNTDVVVGVPSIYMAEVRQ
KLPKTIGVAAQNCYKVPKGAFTGEISPAMIKDVGAEWVILGHSERRNVFGESDQ
LIGEKVEHALQEGLHVIACIGELLEEREAGKTTEVVFRQTQVISKHVKDWSKVV
LAYEPVWAIGTGKTASPQQAQEVHQKLRQWFSENVSPQIAETIRIIYGGSVTAN
NAKELASQADVDGFLVGGASLKPEFVQIVNARQ
```

Der f 25_iso1_TI                                                (SEQ ID NO: 29)

```
MVRKFFVGGNWKMNGSRATNEDLIKTLSNGPLDPNTDVVVGVPSIYMAEVRQ
KLPKTIGVAAQNCYKVPKGAFTGEISPAMIKDVGAEWVILGHSERRNVFGESDQ
LIGEKVEHALQEGLHVIACIGELLEEREAGKTTEVVFRQTQVISKHVKDWSKVV
LAYEPVGPLVLVKQPVHNKHKKFIKNFDNGFLKMFHHKLPKQFESFMVVQ
```

Der f 25_iso1_TI                                                (SEQ ID NO: 30)

```
MVRKFFVGGNWKMNGSRATNEDLIKTLSNGPLDPNTDVVVGVPSIYMAEVRQ
KLPKTIGVAAQNCYKVPKGAFTGEISPAMIKDVGAEWVILGHSERRNVFGESDQ
LIGEKVEHALQEGLHVIACIGELLEEREAGKTTEVVFRQTQVISKHVKDWSKVV
LAYEPVWAIGTGKTASPQQAQEVHQKLRQWFSEMFHHKLPKQFESFMVVQ
```

Der f 16_iso1                                                   (SEQ ID NO: 59)

```
MAAHDKNFDVIPIGHTFFFIWRIKQFELVPVPKEDYGKFYKGDCYIVACCTENP
TGGHSKMESKPILNGHGYCHIHFWIGSESTKDEAGVAAIKSVELDDFLGGYPVQ
HREIEEFESRQFSSYFKNGIIYLKGGYESGFTKMIDELKPSLLHVKGKKRPIVYEC
AEISWKVMNNGDVFILLVPNFVFVWTGKHSNRMERTTAIRVANDLKSELNRFK
LSSVILEDGKEVEQTSGAEYDAFNKALSLDKKDIDLKQMPKGYDYAASDKSFE
SHERSFVTLYKCFEGTETIDISFVKNGPLSRADLDTNDTFIVENGSEGLWVWVG
KKATQKERQSAIKYAMELINKKKYPNNTPVTKVLEGDESVEFKSLFESWQMSE
QEKITSARLFRVSRNGIFKQVANYEPDDLEEDNIMILDVMDKIYVWIGNQFAERI
ADEAHVDKVAQRFIQEDKSGRKFRPNQIIKLKQGSEDGAFKSYFPKWN
```

Der f 16_iso1_TI                                                (SEQ ID NO: 31)

```
MAAHDKNFDVIPIGHTFFFIWRIKQFELVPVPKEDYGKFYKGDCYIVACCTENP
TGGHSKMESKPILNGHGYCHIHFWIGSESTKDEAGVAAIKSVELDDFLGGYPVQ
HREIEEFESRQFSSYFKNGIIYLKGGYESGFTKMIDELKPSLLHVKGKKRPIVYEC
AEISWKVMNNGDVFILLVPNFVFVWTGKHSNRMERTTAIRVANDLKSELNRFK
LSSVILEDGKEVEQTSGAEYDAFNKALSLDKKDIDLKQMPKGYDYAASDKSFE
SHERSFVTLYKCFEGTETIDISFVKNGPLSRADLDTNDTFIVENGSEGLWVWVG
KKATQKERQSAIKYAMELINKKKYPNNTPVTKVLEGDESVEFKSLFESWQMSE
QEKITSARLFRVSRNGIFKQVANYEPDDLEEDNIMILDVMDKIYVWIGNQFAERI
ADEAHVDKVAQRLYKRIKVAVNFDQIRL
```

Der f 26_iso1                                                   (SEQ ID NO: 60)

```
MALPRVFFDIAADNQPLGRIVIELRSDVVPKTAENFRALCTGEKGFGFKSSSFHR
IIPNFMIQGGDFTNHGTGGKSIYGNKFADENFTLQHTGPGIMSMANAGPNTNG
SQFFITTVKTTWLDGKHVVFGSVVEGMDIVKKVESYGSQSGKPSKKVTIANCG
QL
```

Der f 26_iso1_TI                                                (SEQ ID NO: 32)

```
MALPRVFFDIAADNQPLGRIVIELRSDVVPKTAEISVHFALVKKDLVLNHPHFIV
SYPIL
```

Der f 26_iso1_TI                                                (SEQ ID NO: 33)

```
MALPRVFFDIAADNQPLGRIVIELRSDVVPKTAENFRALCTGEKGFGFKSSSFHR
IIPNFMIQGGDFTNHGTGGKSIYGNKFADENFTLQHTGPGIMSMANAGPNTNG
SQFFITTVKTTWLDGKHVVFGSVVEGMDIVKRWKAMAHNRVNHPRK
```

Der f 23_iso2                                                   (SEQ ID NO: 61)

```
MKFNITIAFVSLAILIHSSYADIDHFDNDDQNSSTSRPDDDPTTMIDVQTTTVQPS
DEFECPTRFGYFADPKDPCKFYICSNWEAIHKSCPGNTRWNEKELTCT
```

Der f 23_iso2_TI (SEQ ID NO: 34)

MKFNITIAFVSLAILIHSSYADIDHFDNDDQNSSTSRPDDDPTTMIDVQTTTVQPS
DEFECPTRFGYFADPKDPCKFIFVQIGKLYIKVVQVIQDGMKKN

Der f 13_iso1

(SEQ ID NO: 62)

MASIEGKYKLEKSEKFDEFLDKLGVGFMVKTAAKTLKPTFEVAIENDQYIFRSL
STFKNTEAKFKLGEEFEEDRADGKRVKTVIQKEGDNKFVQTQFGDKEVKIIREF
NGDEVVVTASCDGVTSVRTYKRI

Der f 13_iso1_TI (SEQ ID NO: 35)

MASIEGKYKLEKSEKFDEFLDKLGVGFMVKTAAKTLKPTFEVAIENDQYIFRSL
STFKNTEAKFKLGEEFEEDRADGKRVKTVIQKKVTINLFKHNSVIKK

Der f 7_iso1

(SEQ ID NO: 63)

MMKFLLIAAVAFVAVSADPIHYDKITEEINKAIDDAIAAIEKSETIDPMKVPDHT
DKFERHVGILDFKGELAMRNIEARGLKQMKRQGDANVKGEEGIVKAHLLIGVH
DDIVSMEYDLAYKLGDLHPNTHVISDIQDFVVALSLEISDEGNITMTSFEVRQFA
NVVNHIGGLSILDPIFGVLSDVLTAIFQDTVRKEMTKVLAPAFKRELEKN

Der f 7_iso1_TI (SEQ ID NO: 36)

MMKFLLIAAVAFVAVSADPIHYDKITEEINKAIDDAIAAIEKSETIDPMKVPDLPI
NSNVMLVFWISKVN

Der f 27_iso1

(SEQ ID NO: 64)

MKFFLLSFVLMIVAATATYAAHVGSGSRDNNNNKPVPAEGFAKASNEFGFHLL
KEVIQHRSSSGSRGSSENVLFSPYSVAVALSMVHQGTQGSTAEQFKRVLYYDR
VQQLNGGEYQTVANSVKQIQNQIKQSDQSNQFPDWGNMLMVDQQIPVKDQYK
KIIEQYYDGQVMSVDFRKESKNVMERINQFVSNKTHGLIDRMLEQPPSADTGLA
LINAVYFKGEWLKPFDSMRTEQSVFYGHHGQEYKNVQYINGQGPYGYVEVPQ
WNSDLIQLPYKGEDIAFYGVLPRERNYDLDKIRQSINSTFVDEIVGQITGSQSSTV
YFPKIELSTSYQLPEILKSMGLQDVFTESADLSGITDKKPMKIDDAIHKAKLILNE
QGTEAGAGTYIQMAVLSALETSHTFRFDHPFMYFIRHLPTGQILFLGEIHDF

Der f 27_iso1_TI (SEQ ID NO: 37)

MKFFLLSFVLMIVAATATYAAHVGSGSRDNNNNKPVPAEGFAKASNEFGFHLL
KEVIQHRSSSGSRGSSENVLFSPYSVAVALSMVHQGTQGSTAEQFKRVLYYDR
VQQLNGGEYQTVANSVKQIQNQIKQSDQSNQFPDWGNMLMVDQQIPVKDQYK
KIIEQYYDGQVMSVDFRKESKNVMERINQFVSNKTHGLIDRMLEQPPSADTGLA
LINAVYFKGEWLKPFDSMRTEQSVFYGHHGQEYKNVQYINGQGPYGYVEVPQ
WNSDLIQLPYKGEDIAFYGVLPRERNMILTKFVNQSIQLLLMKLLDKLLVVSHQ
LFISRKLNSVHHINCRKF

Der f 7_iso2

(SEQ ID NO: 65)

MMKFLLIAAVAFVAVSADPIHYDKITEEINKAIDDAIAAIEKSETIDPMKVPDHT
DKFERHVGILDFKGELAMRNIEARGLKQMKRQGDANVKGEEGIVKAHLLIGVH
DDIVSMEYDLAYKLGDLHPNTHVISDIQDFVVALSLEISDEGNITMTSFEVRQFA
NVVNHIGGLSILDPIFGVLSDVLTAIFQDTVRKEMTKVLAPAFKRELEKN

Der f 7_iso2_TI (SEQ ID NO: 38)

MMKFLLIAAVAFVAVSADPIHYDKITEEINKAIDDAIAAIEKSETIDPMKVPDLPI
NSNVMLVFWISKVN

Der f 29_iso1

(SEQ ID NO: 66)

MALPRVFFDIAADNQPLGRIVIELRSDVVPKTAENFRALCTGEKGFGFKSSSFHR
IIPNFMIQGGDFTNHNGTGGKSIYGNKFADENFTLQHTGPGIMSMANAGPNTNG
SQFFITTVKTTWLDGKHVVFGSVVEGMDIVKKVESYGSQSGKPSKKVTIANCG
QL

Der f 29_iso1_TI (SEQ ID NO: 39)

MALPRVFFDIAADNQPLGRIVIELRSDVVPKTAENFRALCTGEKGFGFKSSSFHR
IIPNFMIQGGDFTNHNGTGGKSIYGNKFADENFTLQHTGPGIMSMANAGPNTNG
SQFFITTVKTTWLDGKHVVFGSVVEGMDIVKRWKAMAHNRVNHPRK

Der f 18_iso1

(SEQ ID NO: 67)

MTRFSLTVLAVLAACFGSNIRPNVATLEPKTVCYYESWVHWRQGEGKMDPEDI
DTSLCTHIVYSYFGIDAATHEIKLLDEYLMKDLHDMEHFTQHKGNAKAMIAVG
GSTMSDQFSKTAAVEHYRETFVVSTVDLMTRYGFDGVMIDWSGMQAKDSDNF
IKLLDKFDEKFAHTSFVMGVTLPATIASYDNYNIPAISNYVDFMNVLSLDYTGS

```
WAHTVGHASPFPEQLKTLEAYHKRGAPRHKMVMAVPFYARTWILEKMNKQDI
GDKASGPGPRGQFTQTDGFLSYNELCVQIQAETNAFTITRDHDNTAIYAVYVHS
NHAEWISFEDRHTLGEKAKNITQQGYAGMSVYTLSNEDVHGVCGDKNPLLHAI
QSNYYHGVVTEPTVVTLPPVTHTTEHVTDIPGVFHCHEEGFFRDKTYCATYYEC
KKGDFGLEKTVHHCANHLQAFDEVSRTCIDHTKIPGC

Der f 18_iso1_TI                                                (SEQ ID NO: 40)

MTRFSLTVLAVLAACFGSNIRPNVATLEPKTVCYYESWVHWRQGEGKMDPEDI
DTSLCTHIVYSYFGIDAATHEIKLLDEYLMKDLHDMEHFTQHKGNAKAMIAVG
GSTMSDQFSKTAAVEHYRETFVVSTVDLMTRYGFDGVMIDWSGMQAKDSDNF
IKLLDKFDEKFAHTSFVMGVTLPATIASYDNYNIPAISNYVDFMNVLSLDYTGS
WAHTVGHASPFPEQLKTLEAYHKRGAPRHKMVMAVPFYARTWILEKMNKQDI
GDKASGPGPRGQFTQTDGFLSYNELCVQIQAETNAFTITRDHDNTAIYAVYVHS
NHAEWISFEDRHTLGEKAKNITQQGYAGMSVYTLSNEDVHGVCGDKNPLLHAI
QSNYYHGVVTEPTVVTLPPVTHTTEHVTDIPGVFHCHEEGFFRDKTYCATYYEC
KKGDFGLEKPCIIVPITYRHLTK

Der f 16_iso2                                                   (SEQ ID NO: 68)

MAAHDKNFDVIPIGHTFFFIWRIKQFELVPVPKEDYGKFYKGDCYIVACCTENP
TGGHSKMESKPILNGHGYCHIHFWIGSESTKDEAGVAAIKSVELDDFLGGYPVQ
HREIEEFESRQFSSYFKNGIIYLKGGYESGFTKMIDELKPSLLHVKGKKRPIVYEC
AEISWKVMNNGDVFILLVPNFVFVWTGKHSNRMERTTAIRVANDLKSELNRFK
LSSVILEDGKEVEQTSGAEYDAFNKALSLDKKDIDLKQMPKGYDYAASDKSFE
SHERSFVTLYKCFEGTETIDISFVKNGPLSRADLDTNDTFIVENGSEGLWVWVG
KKATQKERQSAIKYAMELINKKKYPNNTPVTKVLEGDESVEFKSLFESWQMSE
QEKITSARLFRVSRNGIFKQVANYEPDDLEEDNIMILDVMDKIYVWIGNQFAERI
ADEAHVDKVAQRFIQEDKSGRKFRPNQIIKLKQGSEDGAFKSYFPKWN

Der f 16_iso2_TI                                                (SEQ ID NO: 41)

MAAHDKNFDVIPIGHTFFFIWRIKQFELVPVPKEDYGKFYKGDCYIVACCTENP
TGGHSKMESKPILNGHGYCHIHFWIGSESTKDEAGVAAIKSVELDDFLGGYPVQ
HREIEEFESRQFSSYFKNGIIYLKGGYESGFTKMIDELKPSLLHVKGKKRPIVYEC
AEISWKVMNNGDVFILLVPNFVFVWTGKHSNRMERTTAIRVANDLKSELNRFK
LSSVILEDGKEVEQTSGAEYDAFNKALSLDKKDIDLKQMPKGYDYAASDKSFE
SHERSFVTLYKCFEGTETIDISFVKNGPLSRADLDTNDTFIVENGSEGLWVWVG
KKATQKERQSAIKYAMELINKKKYPNNTPVTKVLEGDESVEFKSLFESWQMSE
QEKITSARLFRVSRNGIFKQVANYEPDDLEEDNIMILDVMDKIYVWIGNQFAERI
ADEAHVDKVAQRLYKRIKVAVNFDQIRL

Der f 7_iso3                                                    (SEQ ID NO: 69)

MMKFLLIAAVAFVAVSADPIHYDKITEEINKAIDDAIAAIEKSETIDPMKVPDHT
DKFERHVGILDFKGELAMRNIEARGLKQMKRQGDANVKGEEGIVKAHLLIGVH
DDIVSMEYDLAYKLGDLHPNTHVISDIQDFVVALSLEISDEGNITMTSFEVRQFA
NVVNHIGGLSILDPIFGVLSDVLTAIFQDTVRKEMTKVLAPAFKRELEKN

Der f 7_iso3_TI                                                 (SEQ ID NO: 42)

MMKFLLIAAVAFVAVSADPIHYDKITEEINKAIDDAIAAIEKSETIDPMKVPDLPI
NSNVMLVFWISKVN

Der f 20_iso1                                                   (SEQ ID NO: 70)

MVDQAVIDKLEAGFQKLQSSAECHSLLKKYLTRNVLDACKGRKTGMGATLVD
VVQSGFENLDSGVGLYAPDAESYTLFKELFDPVIEDYHKGFKPTDKHPQTDFGD
VNTLCNVDPNNEFVISTRVRCGRSLQGYPFNPCLTEAQYKEMEEKVKGQLNSF
EGELKGTYYPLLGMDKATQQQLIDDHFLFKEGDRFLQAANACRFWPVGCGIFH
NDNKTFLIWVNEEDHLRIISMQKGGDLKQVFSRLINGVNHIEKKLPFSRDDRLG
FLTFCPTNLGTTIRASVHIKLPKLAADRKKLEEVAGKYNLQVRGTAGEHTESVG
GVVYDISNKRRMGLTEYQAVKEMQDGILELIKIEKSM

Der f 20_iso1_TI                                                (SEQ ID NO: 43)

MVDQAVIDKLEAGFQKLQSSAECHSLLKKYLTRNVLDACKGRKTGMGATLVD
VVQSGFENLDSGVGLYAPDAESYTLFKELFDPVIEDYHKGFKPTDKHPQTDFGD
VNTCVMWIQIMNLSFQHVYVVADHCKVIHLIHA

Der f 20_iso1_TI                                                (SEQ ID NO: 44)

MVDQAVIDKLEAGFQKLQSSAECHSLLKKYLTRNVLDACKGRKTGMGATLVD
VVQSGFENLDSGVGLYAPDAESYTLFKELFDPVIEDYHKGFKPTDKHPQTDFGD
VNTLCNVDPNNEFVISTRVRCGRSLQGYPFNPCLTEAQYKEMEEKVKGQLNSF
EGELKGTYYPLLGMDKATQQQLIDDHFLFKEGDRFLQAANACRFWPVGCGIFH
NDNKTFLIWVNEEDHLRIISMQKGGDLKQVFSRLINGVNHIEKKLPFSRDDRLG
FLTFCPTNLGTTIRASVHIKLPKLAADRKNWKKLLANITYKYVVLPVNTPKVLA
VFTISVINVWWLLNIRPSKRCKMVFLN
```

-continued

Der f 20_iso1_TI
(SEQ ID NO: 45)
MVDQAVIDKLEAGFQKLQSSAECHSLLKKYLTRNVLDACKGRKTGMGATLVD
VVQSGFENLDSGVGLYAPDAESYTLFKELFDPVIEDYHKGFKPTDKHPQTDFGD
VNTLCNVDPNNEFVISTRVRCGRSLQGYPFNPCLTEAQYKEMEEKVKGQLNSF
EGELKGTYYPLLGMDKATQQQLIDDHFLFKEGDRFLQAANACRFWPVGCIFH
NDNKTFLIWVNEEDHLRIISMQKGGDLKQVFSRLINGVNHIEKKLPFSRDDRLG
FLTFCPTNLGTTIRASVHIKLPKLAADRKKLEEVAGKYNLQVRGTAVNTPKVLA
VFTISVINVVWVLLNIRPSKRCKMVFLN Der f 20_iso1_TI
(SEQ ID NO: 46)
MVDQAVIDKLEAGFQKLQSSAECHSLLKKYLTRNVLDACKGRKTGMGATLVD
VVQSGFENLDSGVGLYAPDAESYTLFKELFDPVIEDYHKGFKPTDKHPQTDFGD
VNTLCNVDPNNEFVISTRVRCGRSLQGYPFNPCLTEAQYKEMEEKVKGQLNSF
EGELKGTYYPLLGMDKATQQQLIDDHFLFKEGDRFLQAANACRFWPVGCIFH
NDNKTFLIWVNEEDHLRIISMQKGGDLKQVFSRLINGVNHIEKKLPFSRDDRLG
FLTFCPTNLGTTIRASVHIKLPKLAADRKKLEEVAGKYNLQVRGTAGEHTESVG
GVTISVINVVWVLLNIRPSKRCKMVFLN Der f 1_iso3
(SEQ ID NO: 71)
MKFALFVVASLIATVYGQSHQYYHTSGLRNLGGSYYRSAGISGVAGLGGLAYG
TGLGYGTRYGYGSGLGYGLGYGLGYGQAVALAPAQAVGYVAAAPAVAVQAP
AVSYAAAAPAVQTVAVQAPAVSYAAAPAVAVQAHTAQVSGPIHAAIESRRTV
EVIDGPSTGDAPVASTVVIGPNVQPINLEFQTQASPLAATQNHVPTAPAEPQQSS
YEEQPDLLRQDIVKPVVQDVHETIVPFRRITQELKPVQESVHQILPRGQERGFYQ
QQQQVRVAQHVAAPAAVAVQPVVQAAPAISAVRVAAAPAVAYAAPAVSTVS
AAPAAIGVIGVQPAAGYIGYGAGYGTGYGTGYGVAKYGTGYGLTSGLIGGGSY
GSSYSVQPASYGTGYGYTTYSSDAYPIRKK Der f 1_iso3_TI
(SEQ ID NO: 47)
MKFALFVVASLIATVYGQSHQYYHTSGLRNLGGSYYRSAGISGVAGLGGLAYG
TGLGYGTRYGYGSGLGYGLGYGLGYGQAVALAPAQAVGYVAAAPAVAVQAP
AVSYAAAAPAVQTVAVQAPAVSYAAAPAVAVQAHTAQVSGPIHAAIESRRTV
EVIDGPSTGDAPVASTVVIGPNVQPINLEFQTQASPLAATQNHVPTAPAEPQQSS
YEEQPDLLRQDIVKPVVQDVHETIVPFRRITQELKPVQESVHQILPRGQERGFYQ
QQQQVRVAQHVAAPAAVAVQPVVQAAPAISAVRVAAAPAVAYAAPAVSTVS
AAPAAIGVIGVQPAAGYIGYGAGYGTGYEQVMVLLNTEPDMVSLAV Der f 1_iso3_TI
(SEQ ID NO: 48)
MKFALFVVASLIATVYGQSHQYYHTSGLRNLGGSYYRSAGISGVAGLGGLAYG
TGLGYGTRYGYGSGLGYGLGYGLGYGQAVALAPAQAVGYVAAAPAVAVQAP
AVSYAAAAPAVQTVAVQAPAVSYAAAPAVAVQAHTAQVSGPIHAAIESRRTV
EVIDGPSTGDAPVASTVVIGPNVQPINLEFQTQASPLAATQNHVPTAPAEPQQSS
YEEQPDLLRQDIVKPVVQDVHETIVPFRRITQELKPVQESVHQILPRGQERGFYQ
QQQQVRVAQHVAAPAAVAVQPVVQAAPAISAVRVAAAPAVAYAAPAVSTVS
AAPAAIGVIGVQPAAGYIGYGAGYGTGYGTGYGVAKYGTGYGLTSGLIGVAH
MDHHIQYNQPATELVMVTLPIAVMPTQSEKNKLVLPFSF Der f 15_iso2
(SEQ ID NO: 72)
MKTIYAILSIMACIGLMNASIKRDHNDYSKNPMRIVCYVGTWSVYHKVDPYTIE
DIDPFKCTHLMYGFAKIDEYKYTIQVFDPYQDDNHNSWEKRGYERFNNLRLKN
PELTTMISLGGWYEGSEKYSDMAANPTYRQQFIQSVLDFLQEYKFDGLDLDWE
YPGSRLGNPKIDKQNYLALVRELKDAFEPHGYLLTAAVSPGKDKIDRAYDIKEL
NKLFDWMNVMTYDYHGGWENFYGHNAPLYKRPDETDELHTYFVNVNYTMHY
YLNNGATRDKLVMGVPFYGRAWSIEDRSKLKLGDPAKGMSPPGFISGEEGVLS
YIELCQLFQKEEWHIQYDEYYNAPYGYNDKIWVGYDDLASISCKLAFLKELGV
SGVIVWSLENDDFKGHCGPKNPLLNKVHNMINGDEKNSFECILGPSTTTPTTTT
PTTTPTPSPTTPTPSPTTPTTTTPSPTTPTPSPTTPTTTTPSPTTPTPTTPTPTPTTSTPSP
TTTEHTSETPKYTTYVDGHLIKCYKEGDIPHPTNIHKYLVCEFVNGGWWVHIMP
CPPGTIWCQEKLTCIGE Der f 15_iso2_TI
(SEQ ID NO: 49)
MKTIYAILSIMACIGLMNASIKRDHNDYSKNPMRIVCYVGTWSVYHKVDPYTIE
DIDPFKCTHLMYGFAKIDEYKYTIQVFDPYQDDNHNSWEKRGYERFNNLRLKN
PELTTMISLGGWYEGSEKYSDMAANPTYRQQFIQSVLDFLQEYKFDGLDWIGSI
LDLDWVTRKSTNKTIWLWLENLKTLLNLMATC Der f 20_iso2
(SEQ ID NO: 73)
MVDQATLSKLEAGFQKLQNAQDCHSLLKKYLTRDVLDQLKTKKTDMGATLL
DVIQSGVENLDSGVGIYAPDAQSYKTFAALFDPIIDDYHKGFKPTDKHPQTDFG
NIEHFVNVDPKNEYVISTRVRCGRSLKGYPFNPMLTEAQYKEMETKVKGQLAT
FEGELKGTYYPLLGMDKATQQKLIDDHFLFKEGDRFLQAANACRYWPVGRGIF
HNDKKTFLMWVNEEDHLRIISMQKGGDLKEVFGRLVKAVKHIEQKIPFSRDDR

```
LGYLTFCPTNLGTTIRASVHIKLPKLAADRKKLEEVAARYNLQVRGTAGEHTES
VGGIYDISNKRRMGLTEYQAVKEMQDGIIELIKMEKSL

Der f 20_iso2_TI
                                                    (SEQ ID NO: 50)
MVDQATLSKLEAGFQKLQNAQDCHSLLKKYLTRDVLDQLKTKKTDMGATLL
DVIQSGVENLDSGVGIYAPDAQSYKTFAALFDPIIDDYHKGFKPTDKHPQTDFG
NIEHFVNVDPKNEYVISTRVRCGRSLKGYPFNPMLTEAQYKEMETKVKGQLAT
FEGELKGTYYPLLGMDKATQQKLIDDHFLFKEGDRFLQAANACRYWPVGRGIF
HNDKKTFLMWVNEEDHLRIISMQKGGDLKEVFGRLVKAVKHIEQKIPFSRDDR
LGYLTFCPTNLGTTIRASVHIKLPKLAADRKKLEEVAARYNLQVRGTAGEHTES
VVVSMILVTNDEWVSPNTKLLRKCKMASLN Der f 20_iso2_TI
                                                    (SEQ ID NO: 51)
MVDQATLSKLEAGFQKLQNAQDCHSLLKKYLTRDVLDQLKTKKTDMGATLL
DVIQSGVENLDSGVGIYAPDAQSYKTFAALFDPIIDDYHKGFKPTDKHPQTDFG
NIEHFVNVDPKNEYVISTRVRCGRSLKGYPFNPMLTEAQYKEMETKVKGQLAT
FEGELKGTYYPLLGMDKATQQKLIDDHFLFKEGDRFLQAANACRYWPVGRGIF
HNDKKTFLMWVNEEDHLRIISMQKGGDLKEVFGRLVKAVKHIEQKIPFSRDDR
LGYLTFCPTNLGTTIRASVHIKLPKLAADRKKLEEVAARYNLQVRGTAGEHTES
VGGIYDISTNDEWVSPNTKLLRKCKMASLN
```

The sequences of TI gap peptides included (in underlined form) in the above TI proteins are the following:

```
Der f 1_iso1_TI
                                                    (SEQ ID NO: 74)
FWPTVTRLWIFLNRNSSIAHLNTDVTAIQYQEASNTSNKMVSLKKEAIHT
LHENNNADDQIRNITVSQTTAKFIHQM Der f 1_iso1_TI
                                                    (SEQ ID NO: 75)
SNIMMDEQSFNMTMVINQTIMPSTLSVTEVHKASIIGSYETVGIQPGVIA
DTDISKPETTS Der f 1_iso1_TI
                                                    (SEQ ID NO: 76)
MVINQTIMPSTLSVTEVHKASIIGSYETVGIQPGVIADTDISKPETTS Der f 1_iso1_TI
                                                    (SEQ ID NO: 77)
IGSYETVGIQPGVIADTDISKPETTS Der f 1_iso2_TI
                                                    (SEQ ID NO: 78)
FWPTVTRLWIFLNRNSSIAHLNTDVTAIQYQEASNTSNKMVSLKKEAIHT
LHENNNADDQIRNITVSQTTAKFIHQM Der f 1_iso2_TI
                                                    (SEQ ID NO: 79)
SNIMMDEQSFNMTMVINQTIMPSTLSVTEVHKASIIGSYETVGIQPGVIA
DTDISKPETTS Der f 1_iso2_TI
                                                    (SEQ ID NO: 80)
MVINQTIMPSTLSVTEVHKASIIGSYETVGIQPGVIADTDISKPETTS Der f 1_iso2_TI
                                                    (SEQ ID NO: 81)
IGSYETVGIQPGVIADTDISKPETTS Der f 23_iso1_TI
                                                    (SEQ ID NO: 82)
IFVQIGKLYIKVVQVIQDGMKKN Der f 11_iso1_TI
                                                    (SEQ ID NO: 83)
YVINVINWHVKTRNLQTILPKLNHN Der f 11_iso1_TI
                                                    (SEQ ID NO: 84)
TMKYIKNLEFLMNEYRNLQLNSNLLKIC Der f 15_iso1_TI
                                                    (SEQ ID NO: 85)
WIGSILDLDWVTRKSTNKTIWLWLENLKTLLNLMATC Der f 32_iso1_TI
                                                    (SEQ ID NO: 86)
LLKKSLKKHINIGKK Der f 25_iso1_TI
                                                    (SEQ ID NO: 87)
GPLVLVKQPVHNKHKKFIKNFDNGFLKMFEIRKLPKQFESFMVVQ Der f 25_iso1_TI
                                                    (SEQ ID NO: 88)
MFHHKLPKQFESFMVVQ Der f 16_iso1_TI
                                                    (SEQ ID NO: 89)
YKRIKVAVNFDQIRL Der f 26_iso1_TI
                                                    (SEQ ID NO: 90)
EISVHFALVKKDLVLNHPHFIVSYPIL Der f 26_iso1_TI
                                                    (SEQ ID NO: 91)
KRWKAMAHNRVNHPRK Der f 23_iso2_TI
                                                    (SEQ ID NO: 92)
IFVQIGKLYIKVVQVIQDGMKKN Der f 13_iso1_TI
                                                    (SEQ ID NO: 93)
KVTINLFKHNSVIKK Der f 7_iso1_TI
                                                    (SEQ ID NO: 94)
LPINSNVMLVFWISKVN Der f 27_iso1_TI
                                                    (SEQ ID NO: 95)
MILTKFVNQSIQLLLMKLLDKLLVVSHQLFISRKLNSVHHINCRKF Der f 7_iso2_TI
                                                    (SEQ ID NO: 96)
LPINSNVMLVFWISKVN Der f 29_iso1_TI
                                                    (SEQ ID NO: 97)
KRWKAMAHNRVNHPRK Der f 18_iso1_TI
                                                    (SEQ ID NO: 98)
KPCIIVPITYRHLTK Der f 16_iso2_TI
                                                    (SEQ ID NO: 99)
YKRIKVAVNFDQIRL
```

```
Der f 7_iso3_TI
                                   (SEQ ID NO: 100)
LPINSNVMLVFWISKVN Der f 20_iso1_TI
                                   (SEQ ID NO: 101)
CVMWIQIMNLSFQHVYVVADHCKVIHLIHA Der f 20_iso1_TI
                                   (SEQ ID NO: 102)
WKKLLANITYKYVVLPVNTPKVLAVFTISVINVVWVLLNIRPSKRCKMVF
LN Der f 20_iso1_TI
                                   (SEQ ID NO: 103)
VNTPKVLAVFTISVINVVWVLLNIRPSKRCKMVFLN Der f 20_iso1_TI
                                   (SEQ ID NO: 104)
TISVINVVWVLLNIRPSKRCKMVFLN Der f 1_iso3_TI
                                   (SEQ ID NO: 105)
EQVMVLLNTEPDMVSLAV Der f 1_iso3_TI
                                   (SEQ ID NO: 106)
VAHMDHHIQYNQPATELVMVTLPIAVMPTQSEKNKLVLPFSF Der f 15_iso2_TI
                                   (SEQ ID NO: 107)
WIGSILDLDWVTRKSTNKTIWLWLENLKTLLNLMATC Der f 20_iso2_TI
                                   (SEQ ID NO: 108)
VVSMILVTNDEWVSPNTKLLRKCKMASLN Der f 20_iso2_TI
                                   (SEQ ID NO: 109)
TNDEWVSPNTKLLRKCKMASLN
```

In conclusion, we were thus able to identify transcription infidelity (TI) events having an impact on the coding sequences of mite allergens, said TI events giving rise to protein variants which are responsible for triggering mite allergy.

Example 5: Analysis of Peanut Allergens: A Correlation Between Transcription Infidelity (TI) Peptides and Peanut Allergy A—Sensitization to Peanut In this experiment, we intraperitoneally injected either the peanut extract (400 µg of protein), or the recombinant canonic peanut protein AraH2 (400 µg) in BalbC mice once per week during 3 weeks in order to induce sensitization to peanut (in groups of 10 mice).

The immunization protocol was carried out according to FIG. 12.

The tested adjuvant was LewisX. A control sample without adjuvant was also tested. Then, we measured the rate of IgE against peanut extract in samples collected at day 33 (see FIG. 7A) and day 49 after the beginning of injections (see FIG. 7B).

Our results clearly show that the peanut extract significantly induces sensitization at day 33, and even twice more at day 49, whereas the recombinant canonic peanut protein AraH2 alone cannot induce sensitization since the level of IgE against peanut extract obtained for AraH2 sensitized mice is comparable to that obtained with controls (as shown in FIG. 7).

B—Production of Recombinant AraH2-TI Proteins and Confirmation of Their Allergenicity We have analyzed AraH2 RNA sequences of *Arachis hypogaea* by Illumina next-generation sequencing and then adapted it to sequential immunization technique in order to produce recombinant Transcription Infidelity (TI) proteins, i.e., AraH2-TI.

In order to define the positions where Transcription Infidelity (TI) events occur, the reads obtained were aligned and we have selected transcription infidelity (TI) positions of deletions which are located at the level of epitopes of AraH2. These TI deletions in epitopes of AraH2 are present in cascade as shown in FIG. 8.

We were able to identify the following TI proteins in peanut (SEQ ID NO: 121 to 131):

```
Arah2-ref1-g11-id30
                                   (SEQ ID NO: 121)
MARQQWELQGDRRCQSQLERANLRPCEQHLMRKSNVTRIHMDGTRTALVR
IRTALVRTRTDVIRTALVHMIGEALDLLSTKRGVAMS Arah2-ref1-g11-id31
                                   (SEQ ID NO: 122)
MARQQWELQGDRRCQSQLERANLRPCEQHLMQKIQRDEDSYGRDPYSLVR
IRTALVRTRTDVIRTALVHMIGEALDLLSTKRGVAMS Arah2-ref1-g11-id32
                                   (SEQ ID NO: 123)
MARQQWELQGDRRCQSQLERANLRPCEQHLMQKIQRDEDSYGRDPYSPSRI
RTALVRTRTDVIRTALVHMIGEALDLLSTKRGVAMS Arah2-ref1-g11-id33
                                   (SEQ ID NO: 124)
MARQQWELQGDRRCQSQLERANLRPCEQHLMQKIQRDEDSYGRDPYSPSQD
PYSPSQDPDRRDPYSLVHMIGEALDLLSTKRGVAMS Arah2-ref1-g11-id34
                                   (SEQ ID NO: 125)
MARQQWELQGDRRCQSQLERANLRPCEQHLMQKIQRDEDSYGRDPYSPSQD
PYSPSQDPDRRDPYSPSPYDRRGAGSLSTKRGVAMS Arah2-ref1-g12-id35
                                   (SEQ ID NO: 126)
MARQQWELQGDRRCQSQLERANLRPCEQHLMQKIQRDEDSYGRDPYSPSQD
PYSPSQDPDRRDPYSPSPYDRRGAGSSQHQERCCNELNEFENNKGACARHC
NR Arah2-ref1-g12-id36
                                   (SEQ ID NO: 127)
MARQQWELQGDRRCQSQLERANLRPCEQHLMQKIQRDEDSYGRDPYSPSQD
PYSPSQDPDRRDPYSPSPYDRRGAGSSQHQERCCNELNEFENNQGACARHC
NR Arah2-ref2-g13-id37
                                   (SEQ ID NO: 128)
MARQQWELQGDRRCQSQLERANLRPCEQHLMQKIQRDEDSYERDPYSPSQD
PYSPSPYDRRGAGSSQHQERCCNELNEFENNKGACARHCNRSWRTRAIGCR
GGNRSNSSRGSSGTCLNSAALGHHSVATWTSKVAAETDTKHLSQKKKRKEK
KIAYI Arah2-ref2-g13-id38
                                   (SEQ ID NO: 129)
MARQQWELQGDRRCQSQLERANLRPCEQHLMQKIQRDEDSYERDPYSPSQD
PYSPSPYDRRGAGSSQHQERCCNELNEFENNQGACARHCNRSWRTRAIGCR
GGNRSNSSRGSSGTCLNSAALGHHSVATWTSKVAAETDTKHLSQKKKRKEK
KIAYI
```

Arah2-ref2-g13-id39

(SEQ ID NO: 130)

MARQQWELQGDRRCQSQLERANLRPCEQHLMQKIQRDEDSYERDPYSPSQD

PYSPSPYDRRGAGSSQHQERCCNELNEFENNQRCMCEALQQIMENQSDRLQ

GRQQEQQSRGSSGTCLNSAALGHHSVATWTSKVAAETDTKHLSQKKKRKEK

KIAYI

Arah2-ref2-g13-id40

(SEQ ID NO: 131)

MARQQWELQGDRRCQSQLERANLRPCEQHLMQKIQRDEDSYERDPYSPSQD

PYSPSPYDRRGAGSSQHQERCCNELNEFENNQRCMCEALQQIMENQSDRLQ

GRQQEQQFKRELRNLPQQCGLRAHSVATWTSKVAAETDTKHLSQKKKRKEK

KIAYI

The sequences of the TI gap peptides (comprised and underlined in the above TI peanut proteins of SEQ ID NO: 121 to 131) and represented in FIG. 8 as bold, are the following:

Arah2-ref1-g11-id30

(SEQ ID NO: 110)

RKSNVTRIHMDGTRTALVRIRTALVRTRTDVIRTALVHMIGEALDLLSTK

RGVAMS

Arah2-ref1-g11-id31

(SEQ ID NO: 111)

LVRIRTALVRTRTDVIRTALVHMIGEALDLLSTKRGVAMS

Arah2-ref1-g11-id32

(SEQ ID NO: 112)

RIRTALVRTRTDVIRTALVHMIGEALDLLSTKRGVAMS

Arah2-ref1-g11-id33

(SEQ ID NO: 113)

LVHMIGEALDLLSTKRGVAMS

Arah2-ref1-g11-id34

(SEQ ID NO: 114)

LSTKRGVAMS

Arah2-ref1-g12-id35

(SEQ ID NO: 115)

KGACARHCNR

Arah2-ref1-g12-id36

(SEQ ID NO: 116)

GACARHCNR

Arah2-ref2-g13-id37

(SEQ ID NO: 117)

KGACARHCNRSWRTRAIGCRGGNRSNSSRGSSGTCLNSAALGHHSVATWT

SKVAAETDTKHLSQKKKRKEKKIAYI

Arah2-ref2-g13-id38

(SEQ ID NO: 118)

GACARHCNRSWRTRAIGCRGGNRSNSSRGSSGTCLNSAALGHHSVATWTS

KVAAETDTKHLSQKKKRKEKKIAYI

Arah2-ref2-g13-id39

(SEQ ID NO: 119)

SRGSSGTCLNSAALGHHSVATWTSKVAAETDTKHLSQKKKRKEKKIAYI

Arah2-ref2-g13-id40

(SEQ ID NO: 120)

HSVATWTSKVAAETDTKHLSQKKKRKEKKIAYI

For comparison, the sequences of the canonical proteins are provided in SEQ ID NO: 132 and 133 below:

Arah2-ref1

(SEQ ID NO: 132)

MARQQWELQGDRRCQSQLERANLRPCEQHLMQKIQRDEDSYGRDPYSPSQ

DPYSPSQDPDRRDPYSPSPYDRRGAGSSQHQERCCNELNEFENNQRCMCE

ALQQIMENQSDRLQGRQQEQQFKRELRNLPQQCGLRAPQRCDLEVESGGR

DRY

Arah2-ref2

(SEQ ID NO: 133)

MARQQWELQGDRRCQSQLERANLRPCEQHLMQKIQRDEDSYERDPYSPSQ

DPYSPSPYDRRGAGSSQHQERCCNELNEFENNQRCMCEALQQIMENQSDR

LQGRQQEQQFKRELRNLPQQCGLRAPQRCDLDVESGGRDRY

Then, we produced the recombinant proteins and measured IgE against variants 36, 38 and 40 (said variants 36, 38 and 40 corresponding to TI proteins of SEQ ID NO: 127, 129 and 131 comprising respectively TI gap peptides of SEQ ID NO: 116, 118 and 120).

We used BalbC mice previously described (see FIG. 9). Therefore, FIG. 9 shows that sensitization to peanut induces IgE reactivity specifically against variant-40 and not against variant-38. Variant-40 contains 2 epitopes (epitopes 8 and 9) that are not present in variant-38.

The recombinant variants of AraH2 are injected in BalbC mice in order to induce sensitization to peanut. A negative control is AraH2 recombinant canonic protein which does not induce sensitization.

This example allows to show that the recombinant canonic AraH2 protein (considered in the art as "allergen") is not allergenic at all. On the contrary, the recombinant AraH2-TI proteins are highly allergenic. In conclusion, only AraH2-TI protein variants which result from Transcription Infidelity (TI) deletion events are at the origin of peanut allergy.

C—Prevalence of Peanut Allergy

The data of the percentages of prevalence of allergy in relation to various peanut allergens are known in the literature (Crit Rev Food Sci Nutr. 2013, Peanut allergens: Sáiz J1, Montealegre C, Marina ml, Garcia-Ruiz C), as summarized in Table 6.

TABLE 6

Prevalence of peanut allergy

| Allergen | Prevalence (%) |
|---|---|
| Ara h 1 | 90 |
| Ara h 2 | 90 |
| Ara h 3 | 50 |
| Ara h 5 | 13 |
| Ara h 6 | 38 |
| Ara h 7 | 43 |
| Ara h 8 | 70 |
| Ara h 9 | 45 |
| Ara h 10 | 21 |
| Ara h 11 | 21 |

In this experiment, we have analyzed mRNA of Ara h 1, Ara h 2, Ara h 3, Ara h 5, Ara h 6, Ara h 7, Ara h 8, Ara h 9, Ara h 10 and Ara h 11 by Illumina next-generation sequencing in order to identify transcription infidelity deletion events. We have then selected the deletions present in the repetitions of A bases, and reported the number of the identified deletions in relation to the transcripts' size.

Results of our analysis and comparison with the known prevalence of peanut allergens (from Table 6), are shown in FIG. 10. This figure clearly demonstrates the existence of a strong correlation between TI deletion events (i.e., number of gap events affecting repetition of A within ORF per 1000 bases) and the prevalence of the peanut allergens. The correlation between these two variables, prevalence and deletions in the repetitions of A, is very highly significant (rho Spearman=0.68; p-value=0.003).

In conclusion, the allergenicity of Ara h 1, Ara h 2, Ara h 3, Ara h 5, Ara h 6, Ara h 7, Ara h 8, Ara h 9, Ara h 10 and Ara h 11 peanut proteins is strictly correlated with transcription infidelity (TI) events and peanut allergy is thus due to production of TI variants of Ara h 1, Ara h 2, Ara h 3, Ara h 5, Ara h 6, Ara h 7, Ara h 8, Ara h 9, Ara h 10 and Ara h 11, resulting from transcription infidelity gap events.

Example 6: Comparison of TI Events in Strongly Allergenic Peanut and Basically Non-Allergenic Green Beans This study relates to the comparison of the phenomenon of transcription infidelity (TI) deletion events in peanut (which is strongly allergenic) and in another leguminous plant such as the green beans (being basically non-allergenic).

In order to compare a TI phenomenon in these two plants, which affects transcripts of different size and the expression of which also varies, we used the measurement of the (RNA-DNA difference) RDD rate, which is calculated by identifying sequence variations in RNA sequences based on a comparison to a reference sequence, and expressed as the rate of deletions computed on all transcript positions (as illustrated in Table 7 below).

TABLE 7

The example of calculating of RDD rate by identifying variations in RNA sequences based on a comparison to a Reference sequence, and expressed as the rate of deletions computed on all transcript positions.

Simplistic example:

| | | | | | | | | | | |
|---|---|---|---|---|---|---|---|---|---|---|
| Reference | A | T | T | C | G | C | A | G | C | A |
| | A | T | T | C | G | C | A | G | | |
| | A | T | T | C | G | C | — | G | | |
| | A | T | T | C | G | C | A | G | C | |
| | A | T | T | C | G | C | A | G | C | A |
| | A | T | — | C | G | C | A | G | C | A |
| | A | T | T | C | G | C | A | G | C | A |
| RNA-seq reads | A | T | T | C | — | C | A | G | C | A |
| | A | T | T | C | G | C | — | G | C | A |
| | A | T | T | C | G | C | A | G | C | A |
| | A | T | — | C | G | C | — | G | C | A |
| | A | T | T | C | G | C | A | G | C | A |
| | A | T | T | C | G | C | A | G | C | A |
| | | T | C | G | C | A | G | C | A | |
| | | | C | G | C | A | G | C | A | |
| | ↓ | ↓ | ↓ | ↓ | ↓ | ↓ | ↓ | ↓ | ↓ | ↓ |
| Number of RDD | 0 | 0 | 2 | 0 | 1 | 0 | 3 | 0 | 0 | 0 |
| Number of reads | 12 | 12 | 13 | 14 | 14 | 14 | 14 | 14 | 12 | 11 |

RDD rate =

$$\text{RDD rate} = \frac{0+0+2+0+1+0+3+0+0+0}{12+12+13+14+14+14+14+14+12+11} = \frac{6}{130}$$

Our results of comparing RDD rate in peanuts and in green beans clearly show that the total RDD rate corresponding to TI deletion events, is significantly higher in peanuts than in green beans, and especially in relation to TI deletion events present in coding regions (ORF) affecting the repetitions of A or T bases. These differences are very highly significant (test of wilcoxon p-value<0.001) as demonstrated in FIG. 11.

The above data further confirm that TI deletion events which are highly present in allergenic peanut proteins, are necessarily at the origin of peanut allergy.

The invention claimed is:

1. A method for reducing immunogenicity or allergenicity of a composition, the method comprising treating the composition to remove cationic proteins, wherein the removed cationic proteins comprise proteins resulting from transcription infidelity.

2. The method of claim 1, which comprises removing at least 50% by weight of the cationic proteins of said composition having an isoelectric point above 7.4.

3. The method of claim 1, wherein the treated composition contains less than 2% by weight of cationic proteins having an isoelectric point above 8.

4. The method of claim 1, wherein the removed cationic proteins comprise a peptide sequence resulting from a transcription infidelity deletion.

5. The method of claim 1, wherein the composition is treated by cation exchange and/or affinity chromatography.

6. The method of claim 5, which comprises (i) providing a solution of the composition, (ii) adjusting, if necessary, the solution of the composition to have a pH between 7 and 9, (iii) subjecting the solution to cation exchange chromatography allowing binding of components of the solution having an isoelectric point above the adjusted pH, and (iv) recovering the unbound flow-through.

7. The method of claim 6, comprising a further step of subjecting the composition to affinity chromatography using transcription infidelity antibodies.

8. The method of claim 1, wherein the composition is or comprises a food ingredient, a feed ingredient, or a drug.

9. The method of claim 1, wherein the composition comprises purified and/or recombinant proteins, polypeptides or peptides.

10. The method of claim 1, wherein the composition comprises milk or a dairy product and the method comprises removing at least one protein comprising a transcription infidelity peptide sequence selected from SEQ ID NO: 1 to 5.

11. The method of claim 1, wherein the composition comprises a peanut product, and the method comprises removing at least one protein comprising a transcription infidelity peptide sequence selected from SEQ ID NO: 110 to 120.

12. A method for preparing a food product comprising (i) providing a food product preparation containing cationic proteins, (ii) treating the food product preparation to remove cationic proteins comprising proteins resulting from transcription infidelity, and (iii) optionally formulating the treated food product with one or more suitable excipients.

13. The method of claim 12, wherein the treated food product contains less than 2% by weight of cationic proteins resulting from transcription infidelity.

14. A method for preparing a pharmaceutical product comprising (i) providing a pharmaceutical product preparation, (ii) treating the pharmaceutical product preparation to remove cationic proteins comprising proteins resulting from transcription infidelity, and (iii) optionally formulating the treated pharmaceutical product with one or more suitable excipients.

15. The method of claim 14, wherein the pharmaceutical product is or comprises a vaccine, an immunogen, an allergen or a drug.

16. A method for reducing immunogenicity or allergenicity of a composition, the method comprising treating the composition to remove cationic proteins, and wherein the method comprises (i) providing a solution of the composition, (ii) adjusting, if necessary, the solution of the composition to have a pH between 7 and 9, (iii) subjecting the solution to cation exchange chromatography allowing binding of components of the solution having an isoelectric point above the adjusted pH, (iv) recovering the unbound flow-through, and (v) subjecting the flow-through to affinity chromatography using transcription infidelity antibodies.

17. A method for reducing immunogenicity or allergenicity of a composition, the method comprising treating the composition to remove cationic proteins, wherein the composition comprises milk or a dairy product and the method comprises removing at least one protein comprising a transcription infidelity peptide sequence selected from SEQ ID NO: 1 to 5.

18. The method of claim 1, wherein the removed cationic proteins comprise proteins comprising a C-terminal transcription infidelity peptide sequence enriched in basic amino acids resulting from a transcription infidelity deletion.

* * * * *

SEQUENCE LISTING

<160> NUMBER OF SEQ ID NOS: 133

<210> SEQ ID NO 1
<211> LENGTH: 16
<212> TYPE: PRT
<213> ORGANISM: Artificial Sequence
<220> FEATURE:
<223> OTHER INFORMATION: TI peptide

<400> SEQUENCE: 1

Leu Trp His Leu Phe Gln Lys Cys Leu Glu Arg Arg Arg Ser Met Asn
1               5                   10                  15

<210> SEQ ID NO 2
<211> LENGTH: 53
<212> TYPE: PRT
<213> ORGANISM: Artificial Sequence
<220> FEATURE:
<223> OTHER INFORMATION: TI peptide

<400> SEQUENCE: 2

Leu Pro Ala Phe Trp Leu Leu Pro Leu Gln Arg Ile Arg Trp Asn Met
1               5                   10                  15

Ser Pro Pro Val Arg Asn Leu Ser Ser Pro Arg Lys His Ile Ser Arg
                20                  25                  30

Lys Arg Ile Trp Pro Leu Ile Pro Ala Arg Arg Thr Phe Ala Pro His
            35                  40                  45

Ser Ala Arg Lys Leu
        50

<210> SEQ ID NO 3
<211> LENGTH: 44
<212> TYPE: PRT
<213> ORGANISM: Artificial Sequence
<220> FEATURE:
<223> OTHER INFORMATION: TI peptide

<400> SEQUENCE: 3

Glu Ala Phe Gln Ala Val Arg Asn Leu Leu His Ala Ser Ile Arg Lys
1               5                   10                  15

Leu Arg Ser Phe Arg Val Arg Asn Ser Ser Lys Gln Arg Met Asn Ser
                20                  25                  30

Arg Ile Lys Ser Thr Pro Leu Pro Arg His Ser Leu
            35                  40

<210> SEQ ID NO 4
<211> LENGTH: 25
<212> TYPE: PRT
<213> ORGANISM: Artificial Sequence
<220> FEATURE:
<223> OTHER INFORMATION: TI peptide

<400> SEQUENCE: 4

Phe Trp Val Pro Arg Ser Lys Thr Lys Asn Asn Gln Tyr Ala Val Arg
1               5                   10                  15

Lys Met Lys Asp Ser Ser Val Thr Lys
                20                  25

<210> SEQ ID NO 5
<211> LENGTH: 64
<212> TYPE: PRT
<213> ORGANISM: Artificial Sequence
<220> FEATURE:
<223> OTHER INFORMATION: TI peptide

<400> SEQUENCE: 5

```
Lys Ser Thr Cys Ser Ser Ala Trp Arg Thr Val Leu Ser Pro Ser Lys
1               5                   10                  15

Ala Trp Pro Ala Ser Ala Trp Ser Gly Pro Arg Arg Trp Thr Thr Arg
            20                  25                  30

Pro Trp Arg Asn Ser Thr Lys Pro Ser Arg Pro Cys Pro Cys Thr Ser
        35                  40                  45

Gly Cys Pro Ser Thr Gln Pro Ser Trp Arg Ser Ser Ala Thr Ser Arg
    50                  55                  60
```

<210> SEQ ID NO 6
<211> LENGTH: 54
<212> TYPE: PRT
<213> ORGANISM: Artificial Sequence
<220> FEATURE:
<223> OTHER INFORMATION: TI protein

<400> SEQUENCE: 6

```
Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Leu Trp His Leu Phe Gln Lys Cys Leu Glu
        35                  40                  45

Arg Arg Arg Ser Met Asn
    50
```

<210> SEQ ID NO 7
<211> LENGTH: 58
<212> TYPE: PRT
<213> ORGANISM: Artificial Sequence
<220> FEATURE:
<223> OTHER INFORMATION: TI protein

<400> SEQUENCE: 7

```
Met Lys Phe Phe Ile Leu Pro Ala Phe Trp Leu Leu Pro Leu Gln Arg
1               5                   10                  15

Ile Arg Trp Asn Met Ser Pro Pro Val Arg Asn Leu Ser Ser Pro Arg
            20                  25                  30

Lys His Ile Ser Arg Lys Arg Ile Trp Pro Leu Ile Pro Ala Arg Arg
        35                  40                  45

Thr Phe Ala Pro His Ser Ala Arg Lys Leu
    50                  55
```

<210> SEQ ID NO 8
<211> LENGTH: 107
<212> TYPE: PRT
<213> ORGANISM: Artificial Sequence
<220> FEATURE:
<223> OTHER INFORMATION: TI protein

<400> SEQUENCE: 8

```
Met Pro Leu Asn Thr Ile Tyr Lys Gln Pro Gln Asn Gln Ile Ile Ile
1               5                   10                  15
```

His Ser Ala Pro Pro Ser Leu Leu Val Leu Tyr Phe Gly Lys Lys Glu
            20                  25                  30

Leu Arg Ala Met Lys Val Leu Ile Leu Ala Cys Leu Val Ala Leu Ala
        35                  40                  45

Leu Ala Arg Glu Leu Glu Glu Leu Asn Val Pro Gly Glu Ile Val Glu
50                  55                  60

Ala Phe Gln Ala Val Arg Asn Leu Leu His Ala Ser Ile Arg Lys Leu
65                  70                  75                  80

Arg Ser Phe Arg Val Arg Asn Ser Ser Lys Gln Arg Met Asn Ser Arg
                85                  90                  95

Ile Lys Ser Thr Pro Leu Pro Arg His Ser Leu
            100                 105

<210> SEQ ID NO 9
<211> LENGTH: 42
<212> TYPE: PRT
<213> ORGANISM: Artificial Sequence
<220> FEATURE:
<223> OTHER INFORMATION: TI protein

<400> SEQUENCE: 9

Met Met Lys Ser Phe Phe Leu Val Val Thr Ile Leu Ala Leu Thr Leu
1               5                   10                  15

Pro Phe Trp Val Pro Arg Ser Lys Thr Lys Asn Asn Gln Tyr Ala Val
            20                  25                  30

Arg Lys Met Lys Asp Ser Ser Val Thr Lys
        35                  40

<210> SEQ ID NO 10
<211> LENGTH: 179
<212> TYPE: PRT
<213> ORGANISM: Artificial Sequence
<220> FEATURE:
<223> OTHER INFORMATION: TI protein

<400> SEQUENCE: 10

Met Lys Cys Leu Leu Leu Ala Leu Ala Leu Thr Cys Gly Ala Gln Ala
1               5                   10                  15

Leu Ile Val Thr Gln Thr Met Lys Gly Leu Asp Ile Gln Lys Val Ala
            20                  25                  30

Gly Thr Trp Tyr Ser Leu Ala Met Ala Ala Ser Asp Ile Ser Leu Leu
        35                  40                  45

Asp Ala Gln Ser Ala Pro Leu Arg Val Tyr Val Glu Glu Leu Lys Pro
50                  55                  60

Thr Pro Glu Gly Asp Leu Glu Ile Leu Leu Gln Lys Trp Glu Asn Gly
65                  70                  75                  80

Glu Cys Ala Gln Lys Lys Ile Ile Ala Glu Lys Thr Lys Ile Pro Ala
                85                  90                  95

Val Phe Lys Ile Asp Ala Leu Asn Glu Asn Lys Val Leu Val Leu Asp
            100                 105                 110

Thr Asp Tyr Lys Ser Thr Cys Ser Ser Ala Trp Arg Thr Val Leu Ser
        115                 120                 125

Pro Ser Lys Ala Trp Pro Ala Ser Ala Trp Ser Gly Pro Arg Arg Trp
    130                 135                 140

Thr Thr Arg Pro Trp Arg Asn Ser Thr Lys Pro Ser Arg Pro Cys Pro
145                 150                 155                 160

Cys Thr Ser Gly Cys Pro Ser Thr Gln Pro Ser Trp Arg Ser Ser Ala

<210> SEQ ID NO 11
<211> LENGTH: 200
<212> TYPE: PRT
<213> ORGANISM: Artificial Sequence
<220> FEATURE:
<223> OTHER INFORMATION: CSN1S1 protein

<400> SEQUENCE: 11

```
Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
        35                  40                  45

Lys Glu Lys Val Asn Glu Leu Ser Lys Asp Ile Gly Ser Glu Ser Thr
50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Ile
            100                 105                 110

Val Pro Asn Ser Ala Glu Glu Arg Leu His Ser Met Lys Glu Gly Ile
        115                 120                 125

His Ala Gln Gln Lys Glu Pro Met Ile Gly Val Asn Gln Glu Leu Ala
    130                 135                 140

Tyr Phe Tyr Pro Glu Leu Phe Arg Gln Phe Tyr Gln Leu Asp Ala Tyr
145                 150                 155                 160

Pro Ser Gly Ala Trp Tyr Tyr Val Pro Leu Gly Thr Gln Tyr Thr Asp
                165                 170                 175

Ala Pro Ser Phe Ser Asp Ile Pro Asn Pro Ile Gly Ser Glu Asn Ser
            180                 185                 190

Glu Lys Thr Thr Met Pro Leu Trp
        195                 200
```

<210> SEQ ID NO 12
<211> LENGTH: 222
<212> TYPE: PRT
<213> ORGANISM: Artificial Sequence
<220> FEATURE:
<223> OTHER INFORMATION: CSN1S2 protein

<400> SEQUENCE: 12

```
Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
            20                  25                  30

Glu Thr Tyr Lys Gln Glu Lys Asn Met Ala Ile Asn Pro Ser Lys Glu
        35                  40                  45

Asn Leu Cys Ser Thr Phe Cys Lys Glu Val Val Arg Asn Ala Asn Glu
50                  55                  60

Glu Glu Tyr Ser Ile Gly Ser Ser Ser Glu Glu Ser Ala Glu Val Ala
65                  70                  75                  80

Thr Glu Glu Val Lys Ile Thr Val Asp Asp Lys His Tyr Gln Lys Ala
```

```
                    85                  90                  95
Leu Asn Glu Ile Asn Gln Phe Tyr Gln Lys Phe Pro Gln Tyr Leu Gln
                100                 105                 110

Tyr Leu Tyr Gln Gly Pro Ile Val Leu Asn Pro Trp Asp Gln Val Lys
                115                 120                 125

Arg Asn Ala Val Pro Ile Thr Pro Thr Leu Asn Arg Glu Gln Leu Ser
                130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Lys Asn Arg Leu
                165                 170                 175

Asn Phe Leu Lys Lys Ile Ser Gln Arg Tyr Gln Lys Phe Ala Leu Pro
                180                 185                 190

Gln Tyr Leu Lys Thr Val Tyr Gln His Gln Lys Ala Met Lys Pro Trp
                195                 200                 205

Ile Gln Pro Lys Thr Lys Val Ile Pro Tyr Val Arg Tyr Leu
                210                 215                 220
```

<210> SEQ ID NO 13
<211> LENGTH: 259
<212> TYPE: PRT
<213> ORGANISM: Artificial Sequence
<220> FEATURE:
<223> OTHER INFORMATION: CSN2 protein

<400> SEQUENCE: 13

```
Met Pro Leu Asn Thr Ile Tyr Lys Gln Pro Gln Asn Gln Ile Ile Ile
1               5                   10                  15

His Ser Ala Pro Pro Ser Leu Leu Val Leu Tyr Phe Gly Lys Lys Glu
                20                  25                  30

Leu Arg Ala Met Lys Val Leu Ile Leu Ala Cys Leu Val Ala Leu Ala
                35                  40                  45

Leu Ala Arg Glu Leu Glu Glu Leu Asn Val Pro Gly Glu Ile Val Glu
        50                  55                  60

Ser Leu Ser Ser Ser Glu Glu Ser Ile Thr Arg Ile Asn Lys Lys Ile
65                  70                  75                  80

Glu Lys Phe Gln Ser Glu Glu Gln Gln Gln Thr Glu Asp Glu Leu Gln
                85                  90                  95

Asp Lys Ile His Pro Phe Ala Gln Thr Gln Ser Leu Val Tyr Pro Phe
                100                 105                 110

Pro Gly Pro Ile His Asn Ser Leu Pro Gln Asn Ile Pro Pro Leu Thr
                115                 120                 125

Gln Thr Pro Val Val Val Pro Pro Phe Leu Gln Pro Glu Val Met Gly
                130                 135                 140

Val Ser Lys Val Lys Glu Ala Met Ala Pro Lys His Lys Glu Met Pro
145                 150                 155                 160

Phe Pro Lys Tyr Pro Val Glu Pro Phe Thr Glu Arg Gln Ser Leu Thr
                165                 170                 175

Leu Thr Asp Val Glu Asn Leu His Leu Pro Leu Pro Leu Leu Gln Ser
                180                 185                 190

Trp Met His Gln Pro His Gln Pro Leu Pro Pro Thr Val Met Phe Pro
                195                 200                 205

Pro Gln Ser Val Leu Ser Leu Ser Gln Ser Lys Val Leu Pro Val Pro
                210                 215                 220

Gln Lys Ala Val Pro Tyr Pro Gln Arg Asp Met Pro Ile Gln Ala Phe
```

```
225                 230                 235                 240
Leu Leu Tyr Gln Glu Pro Val Leu Gly Pro Val Arg Gly Pro Phe Pro
                245                 250                 255

Ile Ile Val

<210> SEQ ID NO 14
<211> LENGTH: 190
<212> TYPE: PRT
<213> ORGANISM: Artificial Sequence
<220> FEATURE:
<223> OTHER INFORMATION: CSN3 protein

<400> SEQUENCE: 14

Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Pro Ile Arg Cys
                20                  25                  30

Glu Lys Asp Glu Arg Phe Phe Ser Asp Lys Ile Ala Lys Tyr Ile Pro
            35                  40                  45

Ile Gln Tyr Val Leu Ser Arg Tyr Pro Ser Tyr Gly Leu Asn Tyr Tyr
        50                  55                  60

Gln Gln Lys Pro Val Ala Leu Ile Asn Asn Gln Phe Leu Pro Tyr Pro
65                  70                  75                  80

Tyr Tyr Ala Lys Pro Ala Ala Val Arg Ser Pro Ala Gln Ile Leu Gln
                85                  90                  95

Trp Gln Val Leu Ser Asn Thr Val Pro Ala Lys Ser Cys Gln Ala Gln
            100                 105                 110

Pro Thr Thr Met Ala Arg His Pro His Pro His Leu Ser Phe Met Ala
        115                 120                 125

Ile Pro Pro Lys Lys Asn Gln Asp Lys Thr Glu Ile Pro Thr Ile Asn
130                 135                 140

Thr Ile Ala Ser Gly Glu Pro Thr Ser Thr Pro Thr Thr Glu Ala Val
145                 150                 155                 160

Glu Ser Thr Val Ala Thr Leu Glu Asp Ser Pro Glu Val Ile Glu Ser
                165                 170                 175

Pro Pro Glu Ile Asn Thr Val Gln Val Thr Ser Thr Ala Val
            180                 185                 190

<210> SEQ ID NO 15
<211> LENGTH: 178
<212> TYPE: PRT
<213> ORGANISM: Artificial Sequence
<220> FEATURE:
<223> OTHER INFORMATION: PAEP protein

<400> SEQUENCE: 15

Met Lys Cys Leu Leu Leu Ala Leu Ala Leu Thr Cys Gly Ala Gln Ala
1               5                   10                  15

Leu Ile Val Thr Gln Thr Met Lys Gly Leu Asp Ile Gln Lys Val Ala
                20                  25                  30

Gly Thr Trp Tyr Ser Leu Ala Met Ala Ala Ser Asp Ile Ser Leu Leu
            35                  40                  45

Asp Ala Gln Ser Ala Pro Leu Arg Val Tyr Val Glu Glu Leu Lys Pro
        50                  55                  60

Thr Pro Glu Gly Asp Leu Glu Ile Leu Leu Gln Lys Trp Glu Asn Gly
65                  70                  75                  80

Glu Cys Ala Gln Lys Lys Ile Ile Ala Glu Lys Thr Lys Ile Pro Ala
```

```
                    85                  90                  95
Val Phe Lys Ile Asp Ala Leu Asn Glu Asn Lys Val Leu Val Leu Asp
                100                 105                 110

Thr Asp Tyr Lys Lys Tyr Leu Leu Phe Cys Met Glu Asn Ser Ala Glu
                115                 120                 125

Pro Glu Gln Ser Leu Ala Cys Gln Cys Leu Val Arg Thr Pro Glu Val
            130                 135                 140

Asp Asp Glu Ala Leu Glu Lys Phe Asp Lys Ala Leu Lys Ala Leu Pro
145                 150                 155                 160

Met His Ile Arg Leu Ser Phe Asn Pro Thr Gln Leu Glu Glu Gln Cys
                165                 170                 175

His Ile

<210> SEQ ID NO 16
<211> LENGTH: 222
<212> TYPE: PRT
<213> ORGANISM: Artificial Sequence
<220> FEATURE:
<223> OTHER INFORMATION: TI protein (Der f 1_iso1_TI)

<400> SEQUENCE: 16

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
                20                  25                  30

Phe Asn Lys Asn Tyr Ala Thr Val Glu Glu Glu Val Ala Arg Lys
            35                  40                  45

Asn Phe Leu Glu Ser Leu Lys Tyr Val Glu Ala Asn Lys Gly Ala Ile
 50                 55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
                100                 105                 110

Leu Asp Leu Arg Ser Leu Arg Thr Val Thr Pro Ile Arg Met Gln Gly
            115                 120                 125

Gly Cys Gly Ser Cys Trp Ala Phe Ser Gly Val Ala Ala Thr Glu Ser
        130                 135                 140

Ala Phe Trp Pro Thr Val Thr Arg Leu Trp Ile Phe Leu Asn Arg Asn
145                 150                 155                 160

Ser Ser Ile Ala His Leu Asn Thr Asp Val Thr Ala Ile Gln Tyr Gln
                165                 170                 175

Glu Ala Ser Asn Thr Ser Asn Lys Met Val Ser Leu Lys Lys Glu Ala
            180                 185                 190

Ile His Thr Leu His Glu Asn Asn Ala Asp Asp Gln Ile Arg Asn
        195                 200                 205

Ile Thr Val Ser Gln Thr Thr Ala Lys Phe Ile His Gln Met
210                 215                 220

<210> SEQ ID NO 17
<211> LENGTH: 309
<212> TYPE: PRT
<213> ORGANISM: Artificial Sequence
<220> FEATURE:
<223> OTHER INFORMATION: TI protein (Der f 1_iso1_TI)
```

<400> SEQUENCE: 17

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Ser Asn Ile Met Met Asp Glu Gln
                245                 250                 255

Ser Phe Asn Met Thr Met Val Ile Asn Gln Thr Ile Met Pro Ser Thr
            260                 265                 270

Leu Ser Val Thr Glu Val His Lys Ala Ser Ile Ile Gly Ser Tyr Glu
        275                 280                 285

Thr Val Gly Ile Gln Pro Gly Val Ile Ala Asp Thr Asp Ile Ser Lys
    290                 295                 300

Pro Glu Thr Thr Ser
305

<210> SEQ ID NO 18
<211> LENGTH: 309
<212> TYPE: PRT
<213> ORGANISM: Artificial Sequence
<220> FEATURE:
<223> OTHER INFORMATION: TI protein (Der f 1_iso1_TI )

<400> SEQUENCE: 18

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Glu Val Ala Arg Lys

```
                35                  40                  45
Asn Phe Leu Glu Ser Leu Lys Tyr Val Glu Ala Asn Lys Gly Ala Ile
 50                  55                  60

Asn His Leu Ser Asp Leu Ser Leu Asp Glu Phe Lys Asn Arg Tyr Leu
 65                  70                  75                  80

Met Ser Ala Glu Ala Phe Glu Gln Leu Lys Thr Gln Phe Asp Leu Asn
                 85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Glu Met Val Ile Asn Gln Thr Ile Met Pro Ser Thr
            260                 265                 270

Leu Ser Val Thr Glu Val His Lys Ala Ser Ile Ile Gly Ser Tyr Glu
        275                 280                 285

Thr Val Gly Ile Gln Pro Gly Val Ile Ala Asp Thr Asp Ile Ser Lys
    290                 295                 300

Pro Glu Thr Thr Ser
305

<210> SEQ ID NO 19
<211> LENGTH: 309
<212> TYPE: PRT
<213> ORGANISM: Artificial Sequence
<220> FEATURE:
<223> OTHER INFORMATION: TI protein (Der f 1_iso1_TI)

<400> SEQUENCE:

```
                85                  90                  95
Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
            115                 120                 125

Gly Cys Gly Ser Cys Trp Ala Phe Ser Gly Val Ala Ala Thr Glu Ser
            130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
            195                 200                 205

His Tyr Gly Ile Ser Asn Tyr Cys Gln Ile Tyr Pro Pro Asp Val Lys
            210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Ile Gly Ser Tyr Glu
            275                 280                 285

Thr Val Gly Ile Gln Pro Gly Val Ile Ala Asp Thr Asp Ile Ser Lys
            290                 295                 300

Pro Glu Thr Thr Ser
305

<210> SEQ ID NO 20
<211> LENGTH: 222
<212> TYPE: PRT
<213> ORGANISM: Artificial Sequence
<220> FEATURE:
<223> OTHER INFORMATION: TI protein (Der f 1_iso2_TI )

<400> SEQUENCE: 20

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
            35                  40                  45

Asn Phe Leu Glu Ser Leu Lys Tyr Val Glu Ala Asn Lys Gly Ala Ile
        50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
            115                 120                 125

Gly Cys Gly Ser Cys Trp Ala Phe Ser Gly Val Ala Ala Thr Glu Ser
```

```
            130                 135                 140
Ala Phe Trp Pro Thr Val Thr Arg Leu Trp Ile Phe Leu Asn Arg Asn
145                 150                 155                 160

Ser Ser Ile Ala His Leu Asn Thr Asp Val Thr Ala Ile Gln Tyr Gln
                165                 170                 175

Glu Ala Ser Asn Thr Ser Asn Lys Met Val Ser Leu Lys Lys Glu Ala
                180                 185                 190

Ile His Thr Leu His Glu Asn Asn Ala Asp Asp Gln Ile Arg Asn
                195                 200                 205

Ile Thr Val Ser Gln Thr Thr Ala Lys Phe Ile His Gln Met
210                 215                 220

<210> SEQ ID NO 21
<211> LENGTH: 309
<212> TYPE: PRT
<213> ORGANISM: Artificial Sequence
<220> FEATURE:
<223> OTHER INFORMATION: TI protein (Der f 1_iso2_TI )

<400> SEQUENCE: 21

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
                20                  25                  30

Phe Asn Lys Asn Tyr Ala Thr Val Glu Glu Glu Val Ala Arg Lys
                35                  40                  45

Asn Phe Leu Glu Ser Leu Lys Tyr Val Glu Ala Asn Lys Gly Ala Ile
50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
                100                 105                 110

Leu Asp Leu Arg Ser Leu Arg Thr Val Thr Pro Ile Arg Met Gln Gly
                115                 120                 125

Gly Cys Gly Ser Cys Trp Ala Phe Ser Gly Val Ala Ala Thr Glu Ser
                130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
                180                 185                 190

Tyr Pro Tyr Val Ala Arg Glu Gln Gln Cys Arg Arg Pro Asn Ser Gln
                195                 200                 205

His Tyr Gly Ile Ser Asn Tyr Cys Gln Ile Tyr Pro Pro Asp Val Lys
                210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Ser Asn Ile Met Met Asp Glu Gln
                245                 250                 255

Ser Phe Asn Met Thr Met Val Ile Asn Gln Thr Ile Met Pro Ser Thr
                260                 265                 270

Leu Ser Val Thr Glu Val His Lys Ala Ser Ile Ile Gly Ser Tyr Glu
```

```
                275                 280                 285
Thr Val Gly Ile Gln Pro Gly Val Ile Ala Asp Thr Asp Ile Ser Lys
    290                 295                 300

Pro Glu Thr Thr Ser
305

<210> SEQ ID NO 22
<211> LENGTH: 309
<212> TYPE: PRT
<213> ORGANISM: Artificial Sequence
<220> FEATURE:
<223> OTHER INFORMATION: TI protein (Der f 1_iso2_TI )

<400> SEQUENCE: 22

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65              70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Glu Met Val Ile Asn Gln Thr Ile Met Pro Ser Thr
            260                 265                 270

Leu Ser Val Thr Glu Val His Lys Ala Ser Ile Ile Gly Ser Tyr Glu
        275                 280                 285

Thr Val Gly Ile Gln Pro Gly Val Ile Ala Asp Thr Asp Ile Ser Lys
    290                 295                 300

Pro Glu Thr Thr Ser
305
```

```
<210> SEQ ID NO 23
<211> LENGTH: 309
<212> TYPE: PRT
<213> ORGANISM: Artificial Sequence
<220> FEATURE:
<223> OTHER INFORMATION: Der f 1_iso2_TI

<400> SEQUENCE: 23

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Ile Gly Ser Tyr Glu
        275                 280                 285

Thr Val Gly Ile Gln Pro Gly Val Ile Ala Asp Thr Asp Ile Ser Lys
290                 295                 300

Pro Glu Thr Thr Ser
305

<210> SEQ ID NO 24
<211> LENGTH: 177
<212> TYPE: PRT
<213> ORGANISM: Artificial Sequence
<220> FEATURE:
<223> OTHER INFORMATION: Der f 23_iso1_TI

<400> SEQUENCE: 24
```

```
Met Lys Phe Asn Ile Thr Ile Ala Phe Val Ser Leu Ala Ile Leu Ile
1               5                   10                  15

His Ser Ser Tyr Ala Asp Ile Asp His Phe Asp Asn Asp Asp Gln Asn
            20                  25                  30

Ser Ser Thr Ser Arg Pro Asp Asp Pro Thr Thr Met Ile Asp Val
        35                  40                  45

Gln Thr Thr Thr Val Gln Pro Ser Ser Met Pro Thr Thr Ser Glu Ser
    50                  55                  60

Gln Ser Thr Val Lys Pro Thr Thr Thr Val Lys Pro Ser Pro Thr
65                  70                  75                  80

Thr Val Lys Leu Thr Thr Thr Val Lys Pro Thr Thr Thr Val
            85                  90                  95

Lys Pro Thr Thr Thr Val Lys Pro Ser Pro Thr Thr Val Lys Pro
            100                 105                 110

Thr Thr Thr Thr Val Lys Pro Ser Pro Thr Thr Thr Thr Thr Thr
            115                 120                 125

Thr Glu Gln Pro Glu Asp Glu Phe Glu Cys Pro Thr Arg Phe Gly Tyr
    130                 135                 140

Phe Ala Asp Pro Lys Asp Pro Cys Lys Phe Ile Phe Val Gln Ile Gly
145                 150                 155                 160

Lys Leu Tyr Ile Lys Val Val Gln Val Ile Gln Asp Gly Met Lys Lys
                165                 170                 175

Asn

<210> SEQ ID NO 25
<211> LENGTH: 439
<212> TYPE: PRT
<213> ORGANISM: Artificial Sequence
<220> FEATURE:
<223> OTHER INFORMATION: Der f 11_iso1_TI

<400> SEQUENCE: 25

Met Ser Ala Arg Thr Ala Lys Tyr Met Tyr Arg Ser Ser Gly Ala Gly
1               5                   10                  15

Ala Ser Gly Asp Ile Ser Val Glu Tyr Gly Thr Asp Leu Gly Ala Leu
            20                  25                  30

Thr Arg Leu Glu Asp Lys Ile Arg Leu Leu Ser Asp Asp Leu Glu Ser
        35                  40                  45

Glu Arg Glu Met Arg Gln Arg Ile Glu Arg Glu Lys Ala Glu Leu Gln
    50                  55                  60

Ile Gln Val Met Ser Leu Gly Glu Arg Leu Glu Glu Ala Glu Gly Ser
65                  70                  75                  80

Ser Glu Ser Val Thr Glu Met Asn Lys Lys Arg Asp Ser Glu Leu Ala
            85                  90                  95

Lys Leu Arg Lys Leu Leu Glu Asp Val His Ile Glu Ser Glu Glu Thr
            100                 105                 110

Ala His His Leu Arg Gln Lys His Gln Ala Ala Ile Gln Glu Met Gln
        115                 120                 125

Asp Gln Leu Asp Gln Leu Gln Lys Ala Lys Asn Lys Ser Asp Lys Glu
    130                 135                 140

Lys Gln Lys Phe Gln Ala Glu Val Phe Glu Leu Leu Ala Gln Leu Glu
145                 150                 155                 160

Thr Ala Asn Lys Glu Lys Leu Thr Ala Leu Lys Asn Val Glu Lys Leu
                165                 170                 175

Glu Tyr Thr Val His Glu Leu Asn Ile Lys Ile Glu Glu Ile Asn Arg
```

```
                180                 185                 190
Thr Val Ile Glu Leu Thr Ser His Lys Gln Arg Leu Ser Gln Glu Asn
            195                 200                 205
Thr Glu Leu Ile Lys Glu Val His Glu Val Lys Leu Gln Leu Asp Asn
        210                 215                 220
Ala Asn His Leu Lys Thr Gln Ile Ala Gln Gln Leu Glu Asp Thr Arg
225                 230                 235                 240
His Arg Leu Glu Glu Glu Arg Lys Arg Ala Ser Leu Glu Asn His
            245                 250                 255
Ala His Thr Leu Glu Val Glu Leu Glu Ser Leu Lys Val Gln Leu Asp
            260                 265                 270
Glu Glu Ser Glu Ala Arg Leu Glu Leu Glu Arg Gln Leu Thr Lys Ala
        275                 280                 285
Asn Gly Asp Ala Ala Ser Trp Lys Ser Lys Tyr Glu Ala Glu Leu Gln
        290                 295                 300
Ala His Ala Asp Glu Val Glu Glu Leu Arg Arg Lys Met Ala Gln Lys
305                 310                 315                 320
Ile Ser Glu Tyr Glu Glu Gln Leu Glu Ala Leu Leu Asn Lys Cys Ser
            325                 330                 335
Ser Leu Glu Lys Gln Lys Ser Arg Leu Gln Ser Glu Val Glu Val Leu
            340                 345                 350
Ile Met Asp Leu Glu Lys Ala Thr Ala His Ala Gln Gln Leu Glu Lys
        355                 360                 365
Arg Val Ala Gln Leu Glu Lys Ile Asn Leu Asp Leu Lys Asn Lys Leu
370                 375                 380
Glu Glu Val Thr Met Leu Met Glu Gln Ala Gln Lys Glu Leu Arg Val
385                 390                 395                 400
Lys Ile Ala Glu Leu Gln Lys Leu Gln His Glu Tyr Glu Asn Tyr Val
            405                 410                 415
Ile Asn Val Ile Asn Trp His Val Lys Thr Arg Asn Leu Gln Thr Ile
        420                 425                 430
Leu Pro Lys Leu Asn His Asn
        435

<210> SEQ ID NO 26
<211> LENGTH: 694
<212> TYPE: PRT
<213> ORGANISM: Artificial Sequence
<220> FEATURE:
<223> OTHER INFORMATION: Der f 11_iso1_TI

<400> SEQUENCE: 26

Met Ser Ala Arg Thr Ala Lys Tyr Met Tyr Arg Ser Ser Gly Ala Gly
1               5                   10                  15
Ala Ser Gly Asp Ile Ser Val Glu Tyr Gly Thr Asp Leu Gly Ala Leu
            20                  25                  30
Thr Arg Leu Glu Asp Lys Ile Arg Leu Leu Ser Asp Asp Leu Glu Ser
        35                  40                  45
Glu Arg Glu Met Arg Gln Arg Ile Glu Arg Glu Lys Ala Glu Leu Gln
    50                  55                  60
Ile Gln Val Met Ser Leu Gly Glu Arg Leu Glu Glu Ala Glu Gly Ser
65                  70                  75                  80
Ser Glu Ser Val Thr Glu Met Asn Lys Lys Arg Asp Ser Glu Leu Ala
            85                  90                  95
Lys Leu Arg Lys Leu Leu Glu Asp Val His Ile Glu Ser Glu Glu Thr
```

```
                100             105             110
Ala His His Leu Arg Gln Lys His Gln Ala Ile Gln Glu Met Gln
            115                 120             125

Asp Gln Leu Asp Gln Leu Gln Lys Ala Lys Asn Lys Ser Asp Lys Glu
        130                 135             140

Lys Gln Lys Phe Gln Ala Glu Val Phe Glu Leu Leu Ala Gln Leu Glu
145             150                 155                 160

Thr Ala Asn Lys Glu Lys Leu Thr Ala Leu Lys Asn Val Glu Lys Leu
            165                 170                 175

Glu Tyr Thr Val His Glu Leu Asn Ile Lys Ile Glu Glu Ile Asn Arg
                180                 185                 190

Thr Val Ile Glu Leu Thr Ser His Lys Gln Arg Leu Ser Gln Glu Asn
            195                 200                 205

Thr Glu Leu Ile Lys Glu Val His Glu Val Lys Leu Gln Leu Asp Asn
        210                 215                 220

Ala Asn His Leu Lys Thr Gln Ile Ala Gln Gln Leu Glu Asp Thr Arg
225                 230                 235                 240

His Arg Leu Glu Glu Glu Arg Lys Arg Ala Ser Leu Glu Asn His
                245                 250                 255

Ala His Thr Leu Glu Val Glu Leu Glu Ser Leu Lys Val Gln Leu Asp
            260                 265                 270

Glu Glu Ser Glu Ala Arg Leu Glu Leu Glu Arg Gln Leu Thr Lys Ala
        275                 280                 285

Asn Gly Asp Ala Ala Ser Trp Lys Ser Lys Tyr Glu Ala Glu Leu Gln
        290                 295                 300

Ala His Ala Asp Glu Val Glu Glu Leu Arg Arg Lys Met Ala Gln Lys
305                 310                 315                 320

Ile Ser Glu Tyr Glu Glu Gln Leu Glu Ala Leu Leu Asn Lys Cys Ser
                325                 330                 335

Ser Leu Glu Lys Gln Lys Ser Arg Leu Gln Ser Glu Val Glu Val Leu
            340                 345                 350

Ile Met Asp Leu Glu Lys Ala Thr His Ala Gln Gln Leu Glu Lys
        355                 360                 365

Arg Val Ala Gln Leu Glu Lys Ile Asn Leu Asp Leu Lys Asn Lys Leu
            370                 375                 380

Glu Glu Val Thr Met Leu Met Glu Gln Ala Gln Lys Glu Leu Arg Val
385                 390                 395                 400

Lys Ile Ala Glu Leu Gln Lys Leu Gln His Glu Tyr Glu Lys Leu Arg
                405                 410                 415

Asp Gln Arg Asp Gln Leu Ala Arg Glu Asn Lys Lys Leu Thr Asp Asp
            420                 425                 430

Leu Ala Glu Ala Lys Ser Gln Leu Asn Asp Ala His Arg Arg Ile His
        435                 440                 445

Glu Gln Glu Ile Glu Ile Lys Arg Leu Glu Asn Glu Arg Asp Glu Leu
        450                 455                 460

Ser Ala Ala Tyr Lys Glu Ala Glu Thr Leu Arg Lys Gln Glu Glu Ala
465                 470                 475                 480

Lys Asn Gln Arg Leu Ile Ala Glu Leu Ala Gln Val Arg His Asp Tyr
                485                 490                 495

Glu Lys Arg Leu Ala Gln Lys Asp Glu Glu Ile Glu Ala Leu Arg Lys
            500                 505                 510

Gln Tyr Gln Ile Glu Ile Glu Gln Leu Asn Met Arg Leu Ala Glu Ala
        515                 520                 525
```

```
Glu Ala Lys Leu Lys Thr Glu Ile Ala Arg Leu Lys Lys Lys Tyr Gln
            530                 535                 540

Ala Gln Ile Thr Glu Leu Glu Leu Ser Leu Asp Ala Ala Asn Lys Ala
545                 550                 555                 560

Asn Ile Asp Leu Gln Lys Thr Ile Lys Lys Gln Ala Leu Gln Ile Thr
                565                 570                 575

Ser Glu Leu Gln Ala His Tyr Asp Glu Val His Arg Gln Leu Gln Gln
            580                 585                 590

Ala Val Asp Gln Leu Gly Val Thr Gln Arg Arg Cys Gln Ala Leu Gln
        595                 600                 605

Ala Glu Leu Glu Glu Met Arg Ile Ala Leu Glu Gln Ala Asn Arg Ala
610                 615                 620

Lys Arg Gln Ala Glu Gln Leu His Glu Glu Ala Val Arg Val Asn
625                 630                 635                 640

Glu Leu Thr Thr Ile Asn Val Asn Leu Ala Ser Ala Lys Ser Lys Leu
                645                 650                 655

Glu Ser Glu Phe Ser Ala Leu Gln Ala Asp Thr Met Lys Tyr Ile Lys
            660                 665                 670

Asn Leu Glu Phe Leu Met Asn Glu Tyr Arg Asn Leu Gln Leu Asn Ser
        675                 680                 685

Asn Leu Leu Lys Ile Cys
    690

<210> SEQ ID NO 27
<211> LENGTH: 193
<212> TYPE: PRT
<213> ORGANISM: Artificial Sequence
<220> FEATURE:
<223> OTHER INFORMATION: Der f 15_iso1_TI

<400> SEQUENCE: 27

Met Lys Thr Ile Tyr Ala Ile Leu Ser Ile Met Ala Cys Ile Gly Leu
1               5                   10                  15

Met Asn Ala Ser Ile Lys Arg Asp His Asn Asp Tyr Ser Lys Asn Pro
            20                  25                  30

Met Arg Ile Val Cys Tyr Val Gly Thr Trp Ser Val Tyr His Lys Val
        35                  40                  45

Asp Pro Tyr Thr Ile Glu Asp Ile Asp Pro Phe Lys Cys Thr His Leu
    50                  55                  60

Met Tyr Gly Phe Ala Lys Ile Asp Glu Tyr Lys Tyr Thr Ile Gln Val
65                  70                  75                  80

Phe Asp Pro Tyr Gln Asp Asp Asn His Asn Ser Trp Glu Lys Arg Gly
                85                  90                  95

Tyr Glu Arg Phe Asn Asn Leu Arg Leu Lys Asn Pro Glu Leu Thr Thr
            100                 105                 110

Met Ile Ser Leu Gly Gly Trp Tyr Glu Gly Ser Glu Lys Tyr Ser Asp
        115                 120                 125

Met Ala Ala Asn Pro Thr Tyr Arg Gln Gln Phe Ile Gln Ser Val Leu
    130                 135                 140

Asp Phe Leu Gln Glu Tyr Lys Phe Asp Gly Leu Asp Trp Ile Gly Ser
145                 150                 155                 160

Ile Leu Asp Leu Asp Trp Val Thr Arg Lys Ser Thr Asn Lys Thr Ile
                165                 170                 175

Trp Leu Trp Leu Glu Asn Leu Lys Thr Leu Leu Asn Leu Met Ala Thr
            180                 185                 190
```

Cys

```
<210> SEQ ID NO 28
<211> LENGTH: 234
<212> TYPE: PRT
<213> ORGANISM: Artificial Sequence
<220> FEATURE:
<223> OTHER INFORMATION: Der f 32_iso1_TI

<400> SEQUENCE: 28
```

Met Ser Thr Thr Asn Tyr Ser Val Asp His Arg Gly Ser Phe Asn Ser
1               5                   10                  15

Leu Asp Tyr Arg Ile Tyr Phe Lys Asp Asn Ser Asn Gly Lys Ile Ile
            20                  25                  30

Ser Pro Trp His Asp Ile Pro Leu Phe Val Asp Lys Ser Ala Lys His
        35                  40                  45

Tyr Asn Met Val Val Glu Ile Pro Arg Trp Thr Asn Glu Lys Met Glu
    50                  55                  60

Ile Ala Thr Ala Glu Pro Met Ser Pro Ile Lys Gln Asp Ile Lys Lys
65                  70                  75                  80

Gly Ala Leu Arg Tyr Val Lys Asn Val Phe Pro His Lys Gly Tyr Ile
                85                  90                  95

Trp Asn Tyr Gly Ala Phe Pro Gln Thr Trp Glu Asn Pro Asn His Ile
            100                 105                 110

Asp Gln Asp Thr Lys Thr Lys Gly Asp Asn Asp Pro Ile Asp Val Ile
        115                 120                 125

Glu Ile Gly Ser Arg Val Ala Lys Arg Gly Asp Val Val Pro Val Lys
    130                 135                 140

Ile Leu Gly Thr Ile Ala Leu Ile Asp Glu Gly Glu Thr Asp Trp Lys
145                 150                 155                 160

Ile Ile Ala Ile Asp Thr Arg Asp Glu Leu Ala Ser Gln Met Asn Asn
                165                 170                 175

Val Asp Asp Val Glu Lys Leu Leu Pro Gly Leu Leu Arg Ala Thr Val
            180                 185                 190

Glu Trp Phe Lys Ile Tyr Lys Ile Pro Asp Gly Lys Pro Ala Asn Lys
        195                 200                 205

Phe Ala Phe Asn Gly Glu Ala Lys Asp Arg Glu Leu Leu Lys Lys Ser
    210                 215                 220

Leu Lys Lys His Ile Asn Ile Gly Lys Lys
225                 230

```
<210> SEQ ID NO 29
<211> LENGTH: 210
<212> TYPE: PRT
<213> ORGANISM: Artificial Sequence
<220> FEATURE:
<223> OTHER INFORMATION: Der f 25_iso1_TI

<400> SEQUENCE: 29
```

Met Val Arg Lys Phe Phe Val Gly Gly Asn Trp Lys Met Asn Gly Ser
1               5                   10                  15

Arg Ala Thr Asn Glu Asp Leu Ile Lys Thr Leu Ser Asn Gly Pro Leu
            20                  25                  30

Asp Pro Asn Thr Asp Val Val Val Gly Val Pro Ser Ile Tyr Met Ala
        35                  40                  45

Glu Val Arg Gln Lys Leu Pro Lys Thr Ile Gly Val Ala Ala Gln Asn
    50                  55                  60

Cys Tyr Lys Val Pro Lys Gly Ala Phe Thr Gly Glu Ile Ser Pro Ala
 65                  70                  75                  80

Met Ile Lys Asp Val Gly Ala Glu Trp Val Ile Leu Gly His Ser Glu
                 85                  90                  95

Arg Arg Asn Val Phe Gly Glu Ser Asp Gln Leu Ile Gly Glu Lys Val
            100                 105                 110

Glu His Ala Leu Gln Glu Gly Leu His Val Ile Ala Cys Ile Gly Glu
        115                 120                 125

Leu Leu Glu Glu Arg Glu Ala Gly Lys Thr Thr Glu Val Val Phe Arg
    130                 135                 140

Gln Thr Gln Val Ile Ser Lys His Val Lys Asp Trp Ser Lys Val Val
145                 150                 155                 160

Leu Ala Tyr Glu Pro Val Gly Pro Leu Val Leu Lys Gln Pro Val
                165                 170                 175

His Asn Lys His Lys Lys Phe Ile Lys Asn Phe Asp Asn Gly Phe Leu
            180                 185                 190

Lys Met Phe His His Lys Leu Pro Lys Gln Phe Glu Ser Phe Met Val
        195                 200                 205

Val Gln
    210

<210> SEQ ID NO 30
<211> LENGTH: 210
<212> TYPE: PRT
<213> ORGANISM: Artificial Sequence
<220> FEATURE:
<223> OTHER INFORMATION: Der f 25_iso1_TI

<400> SEQUENCE: 30

Met Val Arg Lys Phe Phe Val Gly Gly Asn Trp Lys Met Asn Gly Ser
1               5                   10                  15

Arg Ala Thr Asn Glu Asp Leu Ile Lys Thr Leu Ser Asn Gly Pro Leu
            20                  25                  30

Asp Pro Asn Thr Asp Val Val Gly Val Pro Ser Ile Tyr Met Ala
        35                  40                  45

Glu Val Arg Gln Lys Leu Pro Lys Thr Ile Gly Val Ala Ala Gln Asn
    50                  55                  60

Cys Tyr Lys Val Pro Lys Gly Ala Phe Thr Gly Glu Ile Ser Pro Ala
 65                 70                  75                  80

Met Ile Lys Asp Val Gly Ala Glu Trp Val Ile Leu Gly His Ser Glu
                85                  90                  95

Arg Arg Asn Val Phe Gly Glu Ser Asp Gln Leu Ile Gly Glu Lys Val
            100                 105                 110

Glu His Ala Leu Gln Glu Gly Leu His Val Ile Ala Cys Ile Gly Glu
        115                 120                 125

Leu Leu Glu Glu Arg Glu Ala Gly Lys Thr Thr Glu Val Val Phe Arg
    130                 135                 140

Gln Thr Gln Val Ile Ser Lys His Val Lys Asp Trp Ser Lys Val Val
145                 150                 155                 160

Leu Ala Tyr Glu Pro Val Trp Ala Ile Gly Thr Gly Lys Thr Ala Ser
                165                 170                 175

Pro Gln Gln Ala Gln Glu Val His Gln Lys Leu Arg Gln Trp Phe Ser
            180                 185                 190

Glu Met Phe His His Lys Leu Pro Lys Gln Phe Glu Ser Phe Met Val
        195                 200                 205

Val Gln
    210

<210> SEQ ID NO 31
<211> LENGTH: 460
<212> TYPE: PRT
<213> ORGANISM: Artificial Sequence
<220> FEATURE:
<223> OTHER INFORMATION: Der f 16_iso1_TI

<400> SEQUENCE: 31

Met Ala Ala His Asp Lys Asn Phe Asp Val Ile Pro Ile Gly His Thr
1               5                   10                  15

Phe Phe Phe Ile Trp Arg Ile Lys Gln Phe Glu Leu Val Pro Val Pro
                20                  25                  30

Lys Glu Asp Tyr Gly Lys Phe Tyr Lys Gly Asp Cys Tyr Ile Val Ala
            35                  40                  45

Cys Cys Thr Glu Asn Pro Thr Gly Gly His Ser Lys Met Glu Ser Lys
    50                  55                  60

Pro Ile Leu Asn Gly His Gly Tyr Cys His Ile His Phe Trp Ile Gly
65                  70                  75                  80

Ser Glu Ser Thr Lys Asp Glu Ala Gly Val Ala Ala Ile Lys Ser Val
                85                  90                  95

Glu Leu Asp Asp Phe Leu Gly Gly Tyr Pro Val Gln His Arg Glu Ile
            100                 105                 110

Glu Glu Phe Glu Ser Arg Gln Phe Ser Ser Tyr Phe Lys Asn Gly Ile
        115                 120                 125

Ile Tyr Leu Lys Gly Gly Tyr Glu Ser Gly Phe Thr Lys Met Ile Asp
130                 135                 140

Glu Leu Lys Pro Ser Leu Leu His Val Lys Gly Lys Lys Arg Pro Ile
145                 150                 155                 160

Val Tyr Glu Cys Ala Glu Ile Ser Trp Lys Val Met Asn Asn Gly Asp
                165                 170                 175

Val Phe Ile Leu Leu Val Pro Asn Phe Val Phe Val Trp Thr Gly Lys
            180                 185                 190

His Ser Asn Arg Met Glu Arg Thr Thr Ala Ile Arg Val Ala Asn Asp
        195                 200                 205

Leu Lys Ser Glu Leu Asn Arg Phe Lys Leu Ser Ser Val Ile Leu Glu
210                 215                 220

Asp Gly Lys Glu Val Glu Gln Thr Ser Gly Ala Glu Tyr Asp Ala Phe
225                 230                 235                 240

Asn Lys Ala Leu Ser Leu Asp Lys Asp Ile Asp Leu Lys Gln Met
                245                 250                 255

Pro Lys Gly Tyr Asp Tyr Ala Ala Ser Asp Lys Ser Phe Glu Ser His
            260                 265                 270

Glu Arg Ser Phe Val Thr Leu Tyr Lys Cys Phe Glu Gly Thr Glu Thr
        275                 280                 285

Ile Asp Ile Ser Phe Val Lys Asn Gly Pro Leu Ser Arg Ala Asp Leu
290                 295                 300

Asp Thr Asn Asp Thr Phe Ile Val Glu Asn Gly Ser Glu Gly Leu Trp
305                 310                 315                 320

Val Trp Val Gly Lys Lys Ala Thr Gln Lys Glu Arg Gln Ser Ala Ile
                325                 330                 335

Lys Tyr Ala Met Glu Leu Ile Asn Lys Lys Tyr Pro Asn Asn Thr
            340                 345                 350

```
Pro Val Thr Lys Val Leu Glu Gly Asp Glu Ser Val Glu Phe Lys Ser
        355                 360                 365

Leu Phe Glu Ser Trp Gln Met Ser Glu Gln Glu Lys Ile Thr Ser Ala
370                 375                 380

Arg Leu Phe Arg Val Ser Arg Asn Gly Ile Phe Lys Gln Val Ala Asn
385                 390                 395                 400

Tyr Glu Pro Asp Asp Leu Glu Glu Asp Asn Ile Met Ile Leu Asp Val
            405                 410                 415

Met Asp Lys Ile Tyr Val Trp Ile Gly Asn Gln Phe Ala Glu Arg Ile
                420                 425                 430

Ala Asp Glu Ala His Val Asp Lys Val Ala Gln Arg Leu Tyr Lys Arg
            435                 440                 445

Ile Lys Val Ala Val Asn Phe Asp Gln Ile Arg Leu
        450                 455                 460

<210> SEQ ID NO 32
<211> LENGTH: 60
<212> TYPE: PRT
<213> ORGANISM: Artificial Sequence
<220> FEATURE:
<223> OTHER INFORMATION: Der f 26_iso1_TI

<400> SEQUENCE: 32

Met Ala Leu Pro Arg Val Phe Phe Asp Ile Ala Ala Asp Asn Gln Pro
1               5                   10                  15

Leu Gly Arg Ile Val Ile Glu Leu Arg Ser Asp Val Val Pro Lys Thr
            20                  25                  30

Ala Glu Ile Ser Val His Phe Ala Leu Val Lys Lys Asp Leu Val Leu
        35                  40                  45

Asn His Pro His Phe Ile Val Ser Tyr Pro Ile Leu
    50                  55                  60

<210> SEQ ID NO 33
<211> LENGTH: 155
<212> TYPE: PRT
<213> ORGANISM: Artificial Sequence
<220> FEATURE:
<223> OTHER INFORMATION: Der f 26_iso1_TI

<400> SEQUENCE: 33

Met Ala Leu Pro Arg Val Phe Phe Asp Ile Ala Ala Asp Asn Gln Pro
1               5                   10                  15

Leu Gly Arg Ile Val Ile Glu Leu Arg Ser Asp Val Val Pro Lys Thr
            20                  25                  30

Ala Glu Asn Phe Arg Ala Leu Cys Thr Gly Glu Lys Gly Phe Gly Phe
        35                  40                  45

Lys Ser Ser Phe His Arg Ile Ile Pro Asn Phe Met Ile Gln Gly
    50                  55                  60

Gly Asp Phe Thr Asn His Asn Gly Thr Gly Gly Lys Ser Ile Tyr Gly
65                  70                  75                  80

Asn Lys Phe Ala Asp Glu Asn Phe Thr Leu Gln His Thr Gly Pro Gly
                85                  90                  95

Ile Met Ser Met Ala Asn Ala Gly Pro Asn Thr Asn Gly Ser Gln Phe
            100                 105                 110

Phe Ile Thr Thr Val Lys Thr Thr Trp Leu Asp Gly Lys His Val Val
        115                 120                 125

Phe Gly Ser Val Val Glu Gly Met Asp Ile Val Lys Arg Trp Lys Ala
```

```
                130               135               140
Met Ala His Asn Arg Val Asn His Pro Arg Lys
145                 150               155

<210> SEQ ID NO 34
<211> LENGTH: 100
<212> TYPE: PRT
<213> ORGANISM: Artificial Sequence
<220> FEATURE:
<223> OTHER INFORMATION: Der f 23_iso2_TI

<400> SEQUENCE: 34

Met Lys Phe Asn Ile Thr Ile Ala Phe Val Ser Leu Ala Ile Leu Ile
1               5                   10                  15

His Ser Ser Tyr Ala Asp Ile Asp His Phe Asp Asn Asp Asp Gln Asn
                20                  25                  30

Ser Ser Thr Ser Arg Pro Asp Asp Pro Thr Thr Met Ile Asp Val
            35                  40                  45

Gln Thr Thr Thr Val Gln Pro Ser Asp Glu Phe Glu Cys Pro Thr Arg
    50                  55                  60

Phe Gly Tyr Phe Ala Asp Pro Lys Asp Pro Cys Lys Phe Ile Phe Val
65                  70                  75                  80

Gln Ile Gly Lys Leu Tyr Ile Lys Val Val Gln Val Ile Gln Asp Gly
                85                  90                  95

Met Lys Lys Asn
            100

<210> SEQ ID NO 35
<211> LENGTH: 101
<212> TYPE: PRT
<213> ORGANISM: Artificial Sequence
<220> FEATURE:
<223> OTHER INFORMATION: Der f 13_iso1_TI

<400> SEQUENCE: 35

Met Ala Ser Ile Glu Gly Lys Tyr Lys Leu Glu Lys Ser Glu Lys Phe
1               5                   10                  15

Asp Glu Phe Leu Asp Lys Leu Gly Val Gly Phe Met Val Lys Thr Ala
                20                  25                  30

Ala Lys Thr Leu Lys Pro Thr Phe Glu Val Ala Ile Glu Asn Asp Gln
            35                  40                  45

Tyr Ile Phe Arg Ser Leu Ser Thr Phe Lys Asn Thr Glu Ala Lys Phe
    50                  55                  60

Lys Leu Gly Glu Glu Phe Glu Glu Asp Arg Ala Asp Gly Lys Arg Val
65                  70                  75                  80

Lys Thr Val Ile Gln Lys Lys Val Thr Ile Asn Leu Phe Lys His Asn
                85                  90                  95

Ser Val Ile Lys Lys
            100

<210> SEQ ID NO 36
<211> LENGTH: 70
<212> TYPE: PRT
<213> ORGANISM: Artificial Sequence
<220> FEATURE:
<223> OTHER INFORMATION: Der f 7_iso1_TI

<400> SEQUENCE: 36

Met Met Lys Phe Leu Leu Ile Ala Ala Val Ala Phe Val Ala Val Ser
1               5                   10                  15
```

Ala Asp Pro Ile His Tyr Asp Lys Ile Thr Glu Glu Ile Asn Lys Ala
            20                  25                  30

Ile Asp Asp Ala Ile Ala Ala Ile Glu Lys Ser Glu Thr Ile Asp Pro
        35                  40                  45

Met Lys Val Pro Asp Leu Pro Ile Asn Ser Asn Val Met Leu Val Phe
    50                  55                  60

Trp Ile Ser Lys Val Asn
65                  70

<210> SEQ ID NO 37
<211> LENGTH: 335
<212> TYPE: PRT
<213> ORGANISM: Artificial Sequence
<220> FEATURE:
<223> OTHER INFORMATION: Der f 27_iso1_TI

<400> SEQUENCE: 37

Met Lys Phe Phe Leu Leu Ser Phe Val Leu Met Ile Val Ala Ala Thr
1               5                   10                  15

Ala Thr Tyr Ala Ala His Val Gly Ser Gly Ser Arg Asp Asn Asn Asn
            20                  25                  30

Asn Lys Pro Val Pro Ala Glu Gly Phe Ala Lys Ala Ser Asn Glu Phe
        35                  40                  45

Gly Phe His Leu Leu Lys Glu Val Ile Gln His Arg Ser Ser Ser Gly
    50                  55                  60

Ser Arg Gly Ser Ser Glu Asn Val Leu Phe Ser Pro Tyr Ser Val Ala
65                  70                  75                  80

Val Ala Leu Ser Met Val His Gln Gly Thr Gln Gly Ser Thr Ala Glu
            85                  90                  95

Gln Phe Lys Arg Val Leu Tyr Tyr Asp Arg Val Gln Gln Leu Asn Gly
        100                 105                 110

Gly Glu Tyr Gln Thr Val Ala Asn Ser Val Lys Gln Ile Gln Asn Gln
    115                 120                 125

Ile Lys Gln Ser Asp Gln Ser Asn Gln Phe Asp Trp Gly Asn Met Leu
130                 135                 140

Met Val Asp Gln Gln Ile Pro Val Lys Asp Gln Tyr Lys Lys Ile Ile
145                 150                 155                 160

Glu Gln Tyr Tyr Asp Gly Gln Val Met Ser Val Asp Phe Arg Lys Glu
            165                 170                 175

Ser Lys Asn Val Met Glu Arg Ile Asn Gln Phe Val Ser Asn Lys Thr
        180                 185                 190

His Gly Leu Ile Asp Arg Met Leu Glu Gln Pro Pro Ser Ala Asp Thr
    195                 200                 205

Gly Leu Ala Leu Ile Asn Ala Val Tyr Phe Lys Gly Glu Trp Leu Lys
210                 215                 220

Pro Phe Asp Ser Met Arg Thr Glu Gln Ser Val Phe Tyr Gly His His
225                 230                 235                 240

Gly Gln Glu Tyr Lys Asn Val Gln Tyr Ile Asn Gly Gln Gly Pro Tyr
            245                 250                 255

Gly Tyr Val Glu Val Pro Gln Trp Asn Ser Asp Leu Ile Gln Leu Pro
        260                 265                 270

Tyr Lys Gly Glu Asp Ile Ala Phe Tyr Gly Val Leu Pro Arg Glu Arg
    275                 280                 285

Asn Met Ile Leu Thr Lys Phe Val Asn Gln Ser Ile Gln Leu Leu Leu
290                 295                 300

Met Lys Leu Leu Asp Lys Leu Leu Val Val Ser His Gln Leu Phe Ile
305                 310                 315                 320

Ser Arg Lys Leu Asn Ser Val His His Ile Asn Cys Arg Lys Phe
                325                 330                 335

<210> SEQ ID NO 38
<211> LENGTH: 70
<212> TYPE: PRT
<213> ORGANISM: Artificial Sequence
<220> FEATURE:
<223> OTHER INFORMATION: Der f 7_iso2_TI

<400> SEQUENCE: 38

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
            20                  25                  30

Ile Asp Asp Ala Ile Ala Ala Ile Glu Lys Ser Glu Thr Ile Asp Pro
        35                  40                  45

Met Lys Val Pro Asp Leu Pro Ile Asn Ser Asn Val Met Leu Val Phe
    50                  55                  60

Trp Ile Ser Lys Val Asn
65                  70

<210> SEQ ID NO 39
<211> LENGTH: 155
<212> TYPE: PRT
<213> ORGANISM: Artificial Sequence
<220> FEATURE:
<223> OTHER INFORMATION: Der f 29_iso1_TI

<400> SEQUENCE: 39

Met Ala Leu Pro Arg Val Phe Phe Asp Ile Ala Ala Asp Asn Gln Pro
1               5                   10                  15

Leu Gly Arg Ile Val Ile Glu Leu Arg Ser Asp Val Val Pro Lys Thr
            20                  25                  30

Ala Glu Asn Phe Arg Ala Leu Cys Thr Gly Glu Lys Gly Phe Gly Phe
        35                  40                  45

Lys Ser Ser Ser Phe His Arg Ile Ile Pro Asn Phe Met Ile Gln Gly
    50                  55                  60

Gly Asp Phe Thr Asn His Asn Gly Thr Gly Gly Lys Ser Ile Tyr Gly
65                  70                  75                  80

Asn Lys Phe Ala Asp Glu Asn Phe Thr Leu Gln His Thr Gly Pro Gly
                85                  90                  95

Ile Met Ser Met Ala Asn Ala Gly Pro Asn Thr Asn Gly Ser Gln Phe
            100                 105                 110

Phe Ile Thr Thr Val Lys Thr Thr Trp Leu Asp Gly Lys His Val Val
        115                 120                 125

Phe Gly Ser Val Val Glu Gly Met Asp Ile Val Lys Arg Trp Lys Ala
    130                 135                 140

Met Ala His Asn Arg Val Asn His Pro Arg Lys
145                 150                 155

<210> SEQ ID NO 40
<211> LENGTH: 448
<212> TYPE: PRT
<213> ORGANISM: Artificial Sequence
<220> FEATURE:
<223> OTHER INFORMATION: Der f 18_iso1_TI

<400> SEQUENCE: 40

```
Met Thr Arg Phe Ser Leu Thr Val Leu Ala Val Leu Ala Ala Cys Phe
1               5                   10                  15

Gly Ser Asn Ile Arg Pro Asn Val Ala Thr Leu Glu Pro Lys Thr Val
            20                  25                  30

Cys Tyr Tyr Glu Ser Trp Val His Trp Arg Gln Gly Glu Gly Lys Met
                35                  40                  45

Asp Pro Glu Asp Ile Asp Thr Ser Leu Cys Thr His Ile Val Tyr Ser
        50                  55                  60

Tyr Phe Gly Ile Asp Ala Ala Thr His Glu Ile Lys Leu Leu Asp Glu
65                  70                  75                  80

Tyr Leu Met Lys Asp Leu His Asp Met Glu His Phe Thr Gln His Lys
                85                  90                  95

Gly Asn Ala Lys Ala Met Ile Ala Val Gly Gly Ser Thr Met Ser Asp
            100                 105                 110

Gln Phe Ser Lys Thr Ala Ala Val Glu His Tyr Arg Glu Thr Phe Val
        115                 120                 125

Val Ser Thr Val Asp Leu Met Thr Arg Tyr Gly Phe Asp Gly Val Met
130                 135                 140

Ile Asp Trp Ser Gly Met Gln Ala Lys Asp Ser Asp Asn Phe Ile Lys
145                 150                 155                 160

Leu Leu Asp Lys Phe Asp Glu Lys Phe Ala His Thr Ser Phe Val Met
                165                 170                 175

Gly Val Thr Leu Pro Ala Thr Ile Ala Ser Tyr Asp Asn Tyr Asn Ile
            180                 185                 190

Pro Ala Ile Ser Asn Tyr Val Asp Phe Met Asn Val Leu Ser Leu Asp
        195                 200                 205

Tyr Thr Gly Ser Trp Ala His Thr Val Gly His Ala Ser Pro Phe Pro
210                 215                 220

Glu Gln Leu Lys Thr Leu Glu Ala Tyr His Lys Arg Gly Ala Pro Arg
225                 230                 235                 240

His Lys Met Val Met Ala Val Pro Phe Tyr Ala Arg Thr Trp Ile Leu
                245                 250                 255

Glu Lys Met Asn Lys Gln Asp Ile Gly Asp Lys Ala Ser Gly Pro Gly
            260                 265                 270

Pro Arg Gly Gln Phe Thr Gln Thr Asp Gly Phe Leu Ser Tyr Asn Glu
        275                 280                 285

Leu Cys Val Gln Ile Gln Ala Glu Thr Asn Ala Phe Thr Ile Thr Arg
290                 295                 300

Asp His Asp Asn Thr Ala Ile Tyr Ala Val Tyr Val His Ser Asn His
305                 310                 315                 320

Ala Glu Trp Ile Ser Phe Glu Asp Arg His Thr Leu Gly Glu Lys Ala
                325                 330                 335

Lys Asn Ile Thr Gln Gln Gly Tyr Ala Gly Met Ser Val Ser Tyr Thr Leu
            340                 345                 350

Ser Asn Glu Asp Val His Gly Val Cys Gly Asp Lys Asn Pro Leu Leu
        355                 360                 365

His Ala Ile Gln Ser Asn Tyr Tyr His Gly Val Val Thr Glu Pro Thr
370                 375                 380

Val Val Thr Leu Pro Pro Val Thr His Thr Thr Glu His Val Thr Asp
385                 390                 395                 400

Ile Pro Gly Val Phe His Cys His Glu Glu Gly Phe Phe Arg Asp Lys
```

-continued

```
                405                 410                 415
Thr Tyr Cys Ala Thr Tyr Tyr Glu Cys Lys Lys Gly Asp Phe Gly Leu
            420                 425                 430

Glu Lys Pro Cys Ile Ile Val Pro Ile Thr Tyr Arg His Leu Thr Lys
            435                 440                 445

<210> SEQ ID NO 41
<211> LENGTH: 460
<212> TYPE: PRT
<213> ORGANISM: Artificial Sequence
<220> FEATURE:
<223> OTHER INFORMATION: Der f 16_iso2_TI

<400> SEQUENCE: 41

Met Ala Ala His Asp Lys Asn Phe Asp Val Ile Pro Ile Gly His Thr
1               5                   10                  15

Phe Phe Phe Ile Trp Arg Ile Lys Gln Phe Glu Leu Val Pro Val Pro
                20                  25                  30

Lys Glu Asp Tyr Gly Lys Phe Tyr Lys Gly Asp Cys Tyr Ile Val Ala
            35                  40                  45

Cys Cys Thr Glu Asn Pro Thr Gly Gly His Ser Lys Met Glu Ser Lys
        50                  55                  60

Pro Ile Leu Asn Gly His Gly Tyr Cys His Ile His Phe Trp Ile Gly
65                  70                  75                  80

Ser Glu Ser Thr Lys Asp Glu Ala Gly Val Ala Ala Ile Lys Ser Val
                85                  90                  95

Glu Leu Asp Asp Phe Leu Gly Gly Tyr Pro Val Gln His Arg Glu Ile
            100                 105                 110

Glu Glu Phe Glu Ser Arg Gln Phe Ser Ser Tyr Phe Lys Asn Gly Ile
        115                 120                 125

Ile Tyr Leu Lys Gly Gly Tyr Glu Ser Gly Phe Thr Lys Met Ile Asp
130                 135                 140

Glu Leu Lys Pro Ser Leu Leu His Val Lys Gly Lys Lys Arg Pro Ile
145                 150                 155                 160

Val Tyr Glu Cys Ala Glu Ile Ser Trp Lys Val Met Asn Asn Gly Asp
                165                 170                 175

Val Phe Ile Leu Leu Val Pro Asn Phe Val Phe Val Trp Thr Gly Lys
            180                 185                 190

His Ser Asn Arg Met Glu Arg Thr Thr Ala Ile Arg Val Ala Asn Asp
        195                 200                 205

Leu Lys Ser Glu Leu Asn Arg Phe Lys Leu Ser Ser Val Ile Leu Glu
210                 215                 220

Asp Gly Lys Glu Val Glu Gln Thr Ser Gly Ala Glu Tyr Asp Ala Phe
225                 230                 235                 240

Asn Lys Ala Leu Ser Leu Asp Lys Lys Asp Ile Asp Leu Lys Gln Met
                245                 250                 255

Pro Lys Gly Tyr Asp Tyr Ala Ala Ser Asp Lys Ser Phe Glu Ser His
            260                 265                 270

Glu Arg Ser Phe Val Thr Leu Tyr Lys Cys Phe Glu Gly Thr Glu Thr
        275                 280                 285

Ile Asp Ile Ser Phe Val Lys Asn Gly Pro Leu Ser Arg Ala Asp Leu
290                 295                 300

Asp Thr Asn Asp Thr Phe Ile Val Glu Asn Gly Ser Glu Gly Leu Trp
305                 310                 315                 320

Val Trp Val Gly Lys Lys Ala Thr Gln Lys Glu Arg Gln Ser Ala Ile
```

```
                  325                 330                 335
Lys Tyr Ala Met Glu Leu Ile Asn Lys Lys Tyr Pro Asn Asn Thr
                340                 345                 350

Pro Val Thr Lys Val Leu Glu Gly Asp Glu Ser Val Glu Phe Lys Ser
                355                 360                 365

Leu Phe Glu Ser Trp Gln Met Ser Glu Gln Glu Lys Ile Thr Ser Ala
            370                 375                 380

Arg Leu Phe Arg Val Ser Arg Asn Gly Ile Phe Lys Gln Val Ala Asn
385                 390                 395                 400

Tyr Glu Pro Asp Asp Leu Glu Glu Asp Asn Ile Met Ile Leu Asp Val
                405                 410                 415

Met Asp Lys Ile Tyr Val Trp Ile Gly Asn Gln Phe Ala Glu Arg Ile
                420                 425                 430

Ala Asp Glu Ala His Val Asp Lys Val Ala Gln Arg Leu Tyr Lys Arg
                435                 440                 445

Ile Lys Val Ala Val Asn Phe Asp Gln Ile Arg Leu
                450                 455                 460

<210> SEQ ID NO 42
<211> LENGTH: 70
<212> TYPE: PRT
<213> ORGANISM: Artificial Sequence
<220> FEATURE:
<223> OTHER INFORMATION: Der f 7_iso3_TI

<400> SEQUENCE: 42

Met Met Lys Phe Leu Leu Ile Ala Ala Val Phe Val Ala Val Ser
1               5                   10                  15

Ala Asp Pro Ile His Tyr Asp Lys Ile Thr Glu Glu Ile Asn Lys Ala
                20                  25                  30

Ile Asp Asp Ala Ile Ala Ala Ile Glu Lys Ser Glu Thr Ile Asp Pro
            35                  40                  45

Met Lys Val Pro Asp Leu Pro Ile Asn Ser Asn Val Met Leu Val Phe
        50                  55                  60

Trp Ile Ser Lys Val Asn
65                  70

<210> SEQ ID NO 43
<211> LENGTH: 139
<212> TYPE: PRT
<213> ORGANISM: Artificial Sequence
<220> FEATURE:
<223> OTHER INFORMATION: Der f 20_iso1_TI

<400> SEQUENCE: 43

Met Val Asp Gln Ala Val Ile Asp Lys Leu Glu Ala Gly Phe Gln Lys
1               5                   10                  15

Leu Gln Ser Ser Ala Glu Cys His Ser Leu Leu Lys Lys Tyr Leu Thr
                20                  25                  30

Arg Asn Val Leu Asp Ala Cys Lys Gly Arg Lys Thr Gly Met Gly Ala
            35                  40                  45

Thr Leu Val Asp Val Val Gln Ser Gly Phe Glu Asn Leu Asp Ser Gly
        50                  55                  60

Val Gly Leu Tyr Ala Pro Asp Ala Glu Ser Tyr Thr Leu Phe Lys Glu
65                  70                  75                  80

Leu Phe Asp Pro Val Ile Glu Asp Tyr His Lys Gly Phe Lys Pro Thr
                85                  90                  95
```

```
Asp Lys His Pro Gln Thr Asp Phe Gly Asp Val Asn Thr Cys Val Met
            100                 105                 110

Trp Ile Gln Ile Met Asn Leu Ser Phe Gln His Val Tyr Val Val Ala
        115                 120                 125

Asp His Cys Lys Val Ile His Leu Ile His Ala
        130                 135
```

<210> SEQ ID NO 44
<211> LENGTH: 348
<212> TYPE: PRT
<213> ORGANISM: Artificial Sequence
<220> FEATURE:
<223> OTHER INFORMATION: Der f 20_iso1_TI

<400> SEQUENCE: 44

```
Met Val Asp Gln Ala Val Ile Asp Lys Leu Glu Ala Gly Phe Gln Lys
1               5                   10                  15

Leu Gln Ser Ser Ala Glu Cys His Ser Leu Leu Lys Lys Tyr Leu Thr
            20                  25                  30

Arg Asn Val Leu Asp Ala Cys Lys Gly Arg Lys Thr Gly Met Gly Ala
        35                  40                  45

Thr Leu Val Asp Val Val Gln Ser Gly Phe Glu Asn Leu Asp Ser Gly
    50                  55                  60

Val Gly Leu Tyr Ala Pro Asp Ala Glu Ser Tyr Thr Leu Phe Lys Glu
65                  70                  75                  80

Leu Phe Asp Pro Val Ile Glu Asp Tyr His Lys Gly Phe Lys Pro Thr
                85                  90                  95

Asp Lys His Pro Gln Thr Asp Phe Gly Asp Val Asn Thr Leu Cys Asn
            100                 105                 110

Val Asp Pro Asn Asn Glu Phe Val Ile Ser Thr Arg Val Arg Cys Gly
        115                 120                 125

Arg Ser Leu Gln Gly Tyr Pro Phe Asn Pro Cys Leu Thr Glu Ala Gln
    130                 135                 140

Tyr Lys Glu Met Glu Glu Lys Val Lys Gly Gln Leu Asn Ser Phe Glu
145                 150                 155                 160

Gly Glu Leu Lys Gly Thr Tyr Tyr Pro Leu Leu Gly Met Asp Lys Ala
                165                 170                 175

Thr Gln Gln Leu Ile Asp Asp His Phe Leu Phe Lys Glu Gly Asp
            180                 185                 190

Arg Phe Leu Gln Ala Ala Asn Ala Cys Arg Phe Trp Pro Val Gly Cys
        195                 200                 205

Gly Ile Phe His Asn Asp Asn Lys Thr Phe Leu Ile Trp Val Asn Glu
    210                 215                 220

Glu Asp His Leu Arg Ile Ser Met Gln Lys Gly Gly Asp Leu Lys
225                 230                 235                 240

Gln Val Phe Ser Arg Leu Ile Asn Gly Val Asn His Ile Glu Lys Lys
                245                 250                 255

Leu Pro Phe Ser Arg Asp Asp Arg Leu Gly Phe Leu Thr Phe Cys Pro
            260                 265                 270

Thr Asn Leu Gly Thr Thr Ile Arg Ala Ser Val His Ile Lys Leu Pro
        275                 280                 285

Lys Leu Ala Ala Asp Arg Lys Asn Trp Lys Lys Leu Leu Ala Asn Ile
    290                 295                 300

Ile Tyr Lys Tyr Val Val Leu Pro Val Asn Thr Pro Lys Val Leu Ala
305                 310                 315                 320
```

Val Phe Thr Ile Ser Val Ile Asn Val Val Trp Val Leu Leu Asn Ile
            325                 330                 335
Arg Pro Ser Lys Arg Cys Lys Met Val Phe Leu Asn
            340                 345

<210> SEQ ID NO 45
<211> LENGTH: 348
<212> TYPE: PRT
<213> ORGANISM: Artificial Sequence
<220> FEATURE:
<223> OTHER INFORMATION: Der f 20_iso1_TI

<400> SEQUENCE: 45

Met Val Asp Gln Ala Val Ile Asp Lys Leu Glu Ala Gly Phe Gln Lys
1               5                   10                  15
Leu Gln Ser Ser Ala Glu Cys His Ser Leu Leu Lys Lys Tyr Leu Thr
            20                  25                  30
Arg Asn Val Leu Asp Ala Cys Lys Gly Arg Lys Thr Gly Met Gly Ala
        35                  40                  45
Thr Leu Val Asp Val Val Gln Ser Gly Phe Glu Asn Leu Asp Ser Gly
    50                  55                  60
Val Gly Leu Tyr Ala Pro Asp Ala Glu Ser Tyr Thr Leu Phe Lys Glu
65                  70                  75                  80
Leu Phe Asp Pro Val Ile Glu Asp Tyr His Lys Gly Phe Lys Pro Thr
                85                  90                  95
Asp Lys His Pro Gln Thr Asp Phe Gly Asp Val Asn Thr Leu Cys Asn
            100                 105                 110
Val Asp Pro Asn Asn Glu Phe Val Ile Ser Thr Arg Val Arg Cys Gly
        115                 120                 125
Arg Ser Leu Gln Gly Tyr Pro Phe Asn Pro Cys Leu Thr Glu Ala Gln
    130                 135                 140
Tyr Lys Glu Met Glu Glu Lys Val Lys Gly Gln Leu Asn Ser Phe Glu
145                 150                 155                 160
Gly Glu Leu Lys Gly Thr Tyr Tyr Pro Leu Leu Gly Met Asp Lys Ala
                165                 170                 175
Thr Gln Gln Gln Leu Ile Asp Asp His Phe Leu Phe Lys Glu Gly Asp
            180                 185                 190
Arg Phe Leu Gln Ala Ala Asn Ala Cys Arg Phe Trp Pro Val Gly Cys
        195                 200                 205
Gly Ile Phe His Asn Asp Asn Lys Thr Phe Leu Ile Trp Val Asn Glu
    210                 215                 220
Glu Asp His Leu Arg Ile Ile Ser Met Gln Lys Gly Gly Asp Leu Lys
225                 230                 235                 240
Gln Val Phe Ser Arg Leu Ile Asn Gly Val Asn His Ile Glu Lys Lys
                245                 250                 255
Leu Pro Phe Ser Arg Asp Asp Arg Leu Gly Phe Leu Thr Phe Cys Pro
            260                 265                 270
Thr Asn Leu Gly Thr Thr Ile Arg Ala Ser Val His Ile Lys Leu Pro
        275                 280                 285
Lys Leu Ala Ala Asp Arg Lys Lys Leu Glu Glu Val Ala Gly Lys Tyr
    290                 295                 300
Asn Leu Gln Val Arg Gly Thr Ala Val Asn Thr Pro Lys Val Leu Ala
305                 310                 315                 320
Val Phe Thr Ile Ser Val Ile Asn Val Val Trp Val Leu Leu Asn Ile
                325                 330                 335

```
Arg Pro Ser Lys Arg Cys Lys Met Val Phe Leu Asn
            340                 345
```

<210> SEQ ID NO 46
<211> LENGTH: 348
<212> TYPE: PRT
<213> ORGANISM: Artificial Sequence
<220> FEATURE:
<223> OTHER INFORMATION: Der f 20_iso1_TI

<400> SEQUENCE: 46

```
Met Val Asp Gln Ala Val Ile Asp Lys Leu Glu Ala Gly Phe Gln Lys
1               5                   10                  15

Leu Gln Ser Ser Ala Glu Cys His Ser Leu Leu Lys Lys Tyr Leu Thr
            20                  25                  30

Arg Asn Val Leu Asp Ala Cys Lys Gly Arg Lys Thr Gly Met Gly Ala
        35                  40                  45

Thr Leu Val Asp Val Val Gln Ser Gly Phe Glu Asn Leu Asp Ser Gly
    50                  55                  60

Val Gly Leu Tyr Ala Pro Asp Ala Glu Ser Tyr Thr Leu Phe Lys Glu
65                  70                  75                  80

Leu Phe Asp Pro Val Ile Glu Asp Tyr His Lys Gly Phe Lys Pro Thr
                85                  90                  95

Asp Lys His Pro Gln Thr Asp Phe Gly Asp Val Asn Thr Leu Cys Asn
            100                 105                 110

Val Asp Pro Asn Asn Glu Phe Val Ile Ser Thr Arg Val Arg Cys Gly
        115                 120                 125

Arg Ser Leu Gln Gly Tyr Pro Phe Asn Pro Cys Leu Thr Glu Ala Gln
130                 135                 140

Tyr Lys Glu Met Glu Lys Val Lys Gly Gln Leu Asn Ser Phe Glu
145                 150                 155                 160

Gly Glu Leu Lys Gly Thr Tyr Tyr Pro Leu Leu Gly Met Asp Lys Ala
                165                 170                 175

Thr Gln Gln Gln Leu Ile Asp Asp His Phe Leu Phe Lys Glu Gly Asp
            180                 185                 190

Arg Phe Leu Gln Ala Ala Asn Ala Cys Arg Phe Trp Pro Val Gly Cys
        195                 200                 205

Gly Ile Phe His Asn Asp Asn Lys Thr Phe Leu Ile Trp Val Asn Glu
    210                 215                 220

Glu Asp His Leu Arg Ile Ile Ser Met Gln Lys Gly Gly Asp Leu Lys
225                 230                 235                 240

Gln Val Phe Ser Arg Leu Ile Asn Gly Val Asn His Ile Glu Lys Lys
                245                 250                 255

Leu Pro Phe Ser Arg Asp Asp Arg Leu Gly Phe Leu Thr Phe Cys Pro
            260                 265                 270

Thr Asn Leu Gly Thr Thr Ile Arg Ala Ser Val His Ile Lys Leu Pro
        275                 280                 285

Lys Leu Ala Ala Asp Arg Lys Lys Leu Glu Glu Val Ala Gly Lys Tyr
    290                 295                 300

Asn Leu Gln Val Arg Gly Thr Ala Gly Glu His Thr Glu Ser Val Gly
305                 310                 315                 320

Gly Val Thr Ile Ser Val Ile Asn Val Val Trp Val Leu Leu Asn Ile
                325                 330                 335

Arg Pro Ser Lys Arg Cys Lys Met Val Phe Leu Asn
            340                 345
```

<210> SEQ ID NO 47
<211> LENGTH: 363
<212> TYPE: PRT
<213> ORGANISM: Artificial Sequence
<220> FEATURE:
<223> OTHER INFORMATION: Der f 1_iso3_TI

<400> SEQUENCE: 47

```
Met Lys Phe Ala Leu Phe Val Val Ala Ser Leu Ile Ala Thr Val Tyr
1               5                   10                  15

Gly Gln Ser His Gln Tyr Tyr His Thr Ser Gly Leu Arg Asn Leu Gly
            20                  25                  30

Gly Ser Tyr Tyr Arg Ser Ala Gly Ile Ser Gly Val Ala Gly Leu Gly
        35                  40                  45

Gly Leu Ala Tyr Gly Thr Gly Leu Gly Tyr Gly Thr Arg Tyr Gly Tyr
    50                  55                  60

Gly Ser Gly Leu Gly Tyr Gly Leu Gly Tyr Gly Leu Gly Tyr Gly Gln
65                  70                  75                  80

Ala Val Ala Leu Ala Pro Ala Gln Ala Val Gly Tyr Val Ala Ala Ala
                85                  90                  95

Pro Ala Val Ala Val Gln Ala Pro Ala Val Ser Tyr Ala Ala Ala Ala
            100                 105                 110

Pro Ala Val Gln Thr Val Ala Val Gln Ala Pro Ala Val Ser Tyr Ala
        115                 120                 125

Ala Ala Pro Ala Val Ala Val Gln Ala His Thr Ala Gln Val Ser Gly
    130                 135                 140

Pro Ile His Ala Ala Ile Glu Ser Arg Arg Thr Val Glu Val Ile Asp
145                 150                 155                 160

Gly Pro Ser Thr Gly Asp Ala Pro Val Ala Ser Thr Val Ile Gly
                165                 170                 175

Pro Asn Val Gln Pro Ile Asn Leu Glu Phe Gln Thr Gln Ala Ser Pro
            180                 185                 190

Leu Ala Ala Thr Gln Asn His Val Pro Thr Ala Pro Ala Glu Pro Gln
        195                 200                 205

Gln Ser Ser Tyr Glu Glu Gln Pro Asp Leu Leu Arg Gln Asp Ile Val
    210                 215                 220

Lys Pro Val Val Gln Asp Val His Glu Thr Ile Val Pro Phe Arg Arg
225                 230                 235                 240

Ile Thr Gln Glu Leu Lys Pro Val Gly Glu Ser Val His Gln Ile Leu
                245                 250                 255

Pro Arg Gly Gln Glu Arg Gly Phe Tyr Gln Gln Gln Gln Gln Val Arg
            260                 265                 270

Val Ala Gln His Val Ala Ala Pro Ala Ala Val Ala Val Gln Pro Val
        275                 280                 285

Val Gln Ala Ala Pro Ala Ile Ser Ala Val Arg Val Ala Ala Ala Pro
    290                 295                 300

Ala Val Ala Tyr Ala Ala Pro Ala Val Ser Thr Val Ser Ala Ala Pro
305                 310                 315                 320

Ala Ala Ile Gly Val Ile Gly Val Gln Pro Ala Ala Gly Tyr Ile Gly
                325                 330                 335

Tyr Gly Ala Gly Tyr Gly Thr Gly Tyr Glu Gln Val Met Val Leu Leu
            340                 345                 350

Asn Thr Glu Pro Asp Met Val Ser Leu Ala Val
        355                 360
```

<210> SEQ ID NO 48
<211> LENGTH: 408
<212> TYPE: PRT
<213> ORGANISM: Artificial Sequence
<220> FEATURE:
<223> OTHER INFORMATION: Der f 1_iso3_TI

<400> SEQUENCE: 48

```
Met Lys Phe Ala Leu Phe Val Ala Ser Leu Ile Ala Thr Val Tyr
1               5                   10                  15

Gly Gln Ser His Gln Tyr Tyr His Thr Ser Gly Leu Arg Asn Leu Gly
                20                  25                  30

Gly Ser Tyr Tyr Arg Ser Ala Gly Ile Ser Gly Val Ala Gly Leu Gly
            35                  40                  45

Gly Leu Ala Tyr Gly Thr Gly Leu Gly Tyr Gly Thr Arg Tyr Gly Tyr
        50                  55                  60

Gly Ser Gly Leu Gly Tyr Gly Leu Gly Tyr Gly Leu Gly Tyr Gly Gln
65                  70                  75                  80

Ala Val Ala Leu Ala Pro Ala Gln Ala Val Gly Tyr Val Ala Ala Ala
                85                  90                  95

Pro Ala Val Ala Val Gln Ala Pro Ala Val Ser Tyr Ala Ala Ala Ala
                100                 105                 110

Pro Ala Val Gln Thr Val Ala Val Gln Ala Pro Ala Val Ser Tyr Ala
            115                 120                 125

Ala Ala Pro Ala Val Ala Val Gln Ala His Thr Ala Gln Val Ser Gly
        130                 135                 140

Pro Ile His Ala Ala Ile Glu Ser Arg Arg Thr Val Glu Val Ile Asp
145                 150                 155                 160

Gly Pro Ser Thr Gly Asp Ala Pro Val Ala Ser Thr Val Ile Gly
                165                 170                 175

Pro Asn Val Gln Pro Ile Asn Leu Glu Phe Gln Thr Gln Ala Ser Pro
                180                 185                 190

Leu Ala Ala Thr Gln Asn His Val Pro Thr Ala Pro Ala Glu Pro Gln
            195                 200                 205

Gln Ser Ser Tyr Glu Glu Gln Pro Asp Leu Leu Arg Gln Asp Ile Val
        210                 215                 220

Lys Pro Val Val Gln Asp Val His Glu Thr Ile Val Pro Phe Arg Arg
225                 230                 235                 240

Ile Thr Gln Glu Leu Lys Pro Val Gly Glu Ser Val His Gln Ile Leu
                245                 250                 255

Pro Arg Gly Gln Glu Arg Gly Phe Tyr Gln Gln Gln Gln Val Arg
                260                 265                 270

Val Ala Gln His Val Ala Ala Pro Ala Val Ala Val Gln Pro Val
            275                 280                 285

Val Gln Ala Ala Pro Ala Ile Ser Ala Val Arg Val Ala Ala Pro
        290                 295                 300

Ala Val Ala Tyr Ala Ala Pro Ala Val Ser Thr Val Ser Ala Ala Pro
305                 310                 315                 320

Ala Ala Ile Gly Val Ile Gly Val Gln Pro Ala Ala Gly Tyr Ile Gly
                325                 330                 335

Tyr Gly Ala Gly Tyr Gly Thr Gly Tyr Gly Thr Gly Tyr Gly Val Ala
            340                 345                 350

Lys Tyr Gly Thr Gly Tyr Gly Leu Thr Ser Gly Leu Ile Gly Val Ala
        355                 360                 365
```

His Met Asp His His Ile Gln Tyr Asn Gln Pro Ala Thr Glu Leu Val
            370                 375                 380

Met Val Thr Leu Pro Ile Ala Val Met Pro Thr Gln Ser Glu Lys Asn
385                 390                 395                 400

Lys Leu Val Leu Pro Phe Ser Phe
                405

<210> SEQ ID NO 49
<211> LENGTH: 193
<212> TYPE: PRT
<213> ORGANISM: Artificial Sequence
<220> FEATURE:
<223> OTHER INFORMATION: Der f 15_iso2_TI

<400> SEQUENCE: 49

Met Lys Thr Ile Tyr Ala Ile Leu Ser Ile Met Ala Cys Ile Gly Leu
1               5                   10                  15

Met Asn Ala Ser Ile Lys Arg Asp His Asn Asp Tyr Ser Lys Asn Pro
            20                  25                  30

Met Arg Ile Val Cys Tyr Val Gly Thr Trp Ser Val Tyr His Lys Val
        35                  40                  45

Asp Pro Tyr Thr Ile Glu Asp Ile Asp Pro Phe Lys Cys Thr His Leu
50                  55                  60

Met Tyr Gly Phe Ala Lys Ile Asp Glu Tyr Lys Tyr Thr Ile Gln Val
65                  70                  75                  80

Phe Asp Pro Tyr Gln Asp Asp Asn His Asn Ser Trp Glu Lys Arg Gly
                85                  90                  95

Tyr Glu Arg Phe Asn Asn Leu Arg Leu Lys Asn Pro Glu Leu Thr Thr
            100                 105                 110

Met Ile Ser Leu Gly Gly Trp Tyr Glu Gly Ser Glu Lys Tyr Ser Asp
        115                 120                 125

Met Ala Ala Asn Pro Thr Tyr Arg Gln Gln Phe Ile Gln Ser Val Leu
    130                 135                 140

Asp Phe Leu Gln Glu Tyr Lys Phe Asp Gly Leu Asp Trp Ile Gly Ser
145                 150                 155                 160

Ile Leu Asp Leu Asp Trp Val Thr Arg Lys Ser Thr Asn Lys Thr Ile
                165                 170                 175

Trp Leu Trp Leu Glu Asn Leu Lys Thr Leu Leu Asn Leu Met Ala Thr
            180                 185                 190

Cys

<210> SEQ ID NO 50
<211> LENGTH: 348
<212> TYPE: PRT
<213> ORGANISM: Artificial Sequence
<220> FEATURE:
<223> OTHER INFORMATION: Der f 20_iso2_TI

<400> SEQUENCE: 50

Met Val Asp Gln Ala Thr Leu Ser Lys Leu Glu Ala Gly Phe Gln Lys
1               5                   10                  15

Leu Gln Asn Ala Gln Asp Cys His Ser Leu Leu Lys Lys Tyr Leu Thr
            20                  25                  30

Arg Asp Val Leu Asp Gln Leu Lys Thr Lys Lys Thr Asp Met Gly Ala
        35                  40                  45

Thr Leu Leu Asp Val Ile Gln Ser Gly Val Glu Asn Leu Asp Ser Gly
50                  55                  60

Val Gly Ile Tyr Ala Pro Asp Ala Gln Ser Tyr Lys Thr Phe Ala Ala
65                  70                  75                  80

Leu Phe Asp Pro Ile Ile Asp Asp Tyr His Lys Gly Phe Lys Pro Thr
                85                  90                  95

Asp Lys His Pro Gln Thr Asp Phe Gly Asn Ile Glu His Phe Val Asn
            100                 105                 110

Val Asp Pro Lys Asn Glu Tyr Val Ile Ser Thr Arg Val Arg Cys Gly
        115                 120                 125

Arg Ser Leu Lys Gly Tyr Pro Phe Asn Pro Met Leu Thr Glu Ala Gln
    130                 135                 140

Tyr Lys Glu Met Glu Thr Lys Val Lys Gly Gln Leu Ala Thr Phe Glu
145                 150                 155                 160

Gly Glu Leu Lys Gly Thr Tyr Tyr Pro Leu Leu Gly Met Asp Lys Ala
                165                 170                 175

Thr Gln Gln Lys Leu Ile Asp Asp His Phe Leu Phe Lys Glu Gly Asp
            180                 185                 190

Arg Phe Leu Gln Ala Ala Asn Ala Cys Arg Tyr Trp Pro Val Gly Arg
    195                 200                 205

Gly Ile Phe His Asn Asp Lys Lys Thr Phe Leu Met Trp Val Asn Glu
210                 215                 220

Glu Asp His Leu Arg Ile Ile Ser Met Gln Lys Gly Gly Asp Leu Lys
225                 230                 235                 240

Glu Val Phe Gly Arg Leu Val Lys Ala Lys His Ile Glu Gln Lys
                245                 250                 255

Ile Pro Phe Ser Arg Asp Asp Arg Leu Gly Tyr Leu Thr Phe Cys Pro
            260                 265                 270

Thr Asn Leu Gly Thr Thr Ile Arg Ala Ser Val His Ile Lys Leu Pro
    275                 280                 285

Lys Leu Ala Ala Asp Arg Lys Lys Leu Glu Glu Val Ala Ala Arg Tyr
290                 295                 300

Asn Leu Gln Val Arg Gly Thr Ala Gly Glu His Thr Glu Ser Val Val
305                 310                 315                 320

Val Ser Met Ile Leu Val Thr Asn Asp Glu Trp Val Ser Pro Asn Thr
                325                 330                 335

Lys Leu Leu Arg Lys Cys Lys Met Ala Ser Leu Asn
            340                 345

<210> SEQ ID NO 51
<211> LENGTH: 348
<212> TYPE: PRT
<213> ORGANISM: Artificial Sequence
<220> FEATURE:
<223> OTHER INFORMATION: Der f 20_iso2_TI

<400> SEQUENCE: 51

Met Val Asp Gln Ala Thr Leu Ser Lys Leu Glu Ala Gly Phe Gln Lys
1               5                   10                  15

Leu Gln Asn Ala Gln Asp Cys His Ser Leu Leu Lys Lys Tyr Leu Thr
                20                  25                  30

Arg Asp Val Leu Asp Gln Leu Lys Thr Lys Thr Asp Met Gly Ala
        35                  40                  45

Thr Leu Leu Asp Val Ile Gln Ser Gly Val Glu Asn Leu Asp Ser Gly
    50                  55                  60

Val Gly Ile Tyr Ala Pro Asp Ala Gln Ser Tyr Lys Thr Phe Ala Ala
65                  70                  75                  80

Leu Phe Asp Pro Ile Ile Asp Asp Tyr His Lys Gly Phe Lys Pro Thr
              85                  90                  95

Asp Lys His Pro Gln Thr Asp Phe Gly Asn Ile Glu His Phe Val Asn
            100                 105                 110

Val Asp Pro Lys Asn Glu Tyr Val Ile Ser Thr Arg Val Arg Cys Gly
            115                 120                 125

Arg Ser Leu Lys Gly Tyr Pro Phe Asn Pro Met Leu Thr Glu Ala Gln
            130                 135                 140

Tyr Lys Glu Met Glu Thr Lys Val Lys Gly Gln Leu Ala Thr Phe Glu
145                 150                 155                 160

Gly Glu Leu Lys Gly Thr Tyr Tyr Pro Leu Leu Gly Met Asp Lys Ala
                165                 170                 175

Thr Gln Gln Lys Leu Ile Asp Asp His Phe Leu Phe Lys Glu Gly Asp
            180                 185                 190

Arg Phe Leu Gln Ala Ala Asn Ala Cys Arg Tyr Trp Pro Val Gly Arg
            195                 200                 205

Gly Ile Phe His Asn Asp Lys Lys Thr Phe Leu Met Trp Val Asn Glu
            210                 215                 220

Glu Asp His Leu Arg Ile Ile Ser Met Gln Lys Gly Gly Asp Leu Lys
225                 230                 235                 240

Glu Val Phe Gly Arg Leu Val Lys Ala Val Lys His Ile Glu Gln Lys
                245                 250                 255

Ile Pro Phe Ser Arg Asp Asp Arg Leu Gly Tyr Leu Thr Phe Cys Pro
            260                 265                 270

Thr Asn Leu Gly Thr Thr Ile Arg Ala Ser Val His Ile Lys Leu Pro
            275                 280                 285

Lys Leu Ala Ala Asp Arg Lys Lys Leu Glu Glu Val Ala Ala Arg Tyr
290                 295                 300

Asn Leu Gln Val Arg Gly Thr Ala Gly Glu His Thr Glu Ser Val Gly
305                 310                 315                 320

Gly Ile Tyr Asp Ile Ser Thr Asn Asp Glu Trp Val Ser Pro Asn Thr
                325                 330                 335

Lys Leu Leu Arg Lys Cys Lys Met Ala Ser Leu Asn
            340                 345

<210> SEQ ID NO 52
<211> LENGTH: 321
<212> TYPE: PRT
<213> ORGANISM: Artificial Sequence
<220> FEATURE:
<223> OTHER INFORMATION: Der f 1_iso1

<400> SEQUENCE: 52

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
                20                  25                  30

Phe Asn Lys Asn Tyr Ala Thr Val Glu Glu Glu Glu Val Ala Arg Lys
            35                  40                  45

Asn Phe Leu Glu Ser Leu Lys Tyr Val Glu Ala Asn Lys Gly Ala Ile
        50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

```
Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Tyr Trp Ile Val Arg
        275                 280                 285

Asn Ser Trp Asp Thr Thr Trp Gly Asp Ser Gly Tyr Gly Tyr Phe Gln
    290                 295                 300

Ala Gly Asn Asn Leu Met Met Ile Glu Gln Tyr Pro Tyr Val Val Ile
305                 310                 315                 320

Met

<210> SEQ ID NO 53
<211> LENGTH: 321
<212> TYPE: PRT
<213> ORGANISM: Artificial Sequence
<220> FEATURE:
<223> OTHER INFORMATION: Der f 1_iso2

<400> SEQUENCE: 53

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
```

```
        130                 135                 140
Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Tyr Trp Ile Val Arg
        275                 280                 285

Asn Ser Trp Asp Thr Thr Trp Gly Asp Ser Gly Tyr Gly Tyr Phe Gln
    290                 295                 300

Ala Gly Asn Asn Leu Met Met Ile Glu Gln Tyr Pro Tyr Val Val Ile
305                 310                 315                 320

Met
```

<210> SEQ ID NO 54
<211> LENGTH: 181
<212> TYPE: PRT
<213> ORGANISM: Artificial Sequence
<220> FEATURE:
<223> OTHER INFORMATION: Der f 23_iso1

<400> SEQUENCE: 54

```
Met Lys Phe Asn Ile Thr Ile Ala Phe Val Ser Leu Ala Ile Leu Ile
1               5                   10                  15

His Ser Ser Tyr Ala Asp Ile Asp His Phe Asp Asn Asp Gln Asn
                20                  25                  30

Ser Ser Thr Ser Arg Pro Asp Asp Pro Thr Thr Met Ile Asp Val
            35                  40                  45

Gln Thr Thr Thr Val Gln Pro Ser Ser Met Pro Thr Thr Ser Glu Ser
50                  55                  60

Gln Ser Thr Val Lys Pro Thr Thr Thr Val Lys Pro Ser Pro Thr
65                  70                  75                  80

Thr Val Lys Leu Thr Thr Thr Thr Val Lys Pro Thr Thr Thr Val
                85                  90                  95

Lys Pro Thr Thr Thr Thr Val Lys Pro Ser Pro Thr Thr Val Lys Pro
                100                 105                 110

Thr Thr Thr Thr Val Lys Pro Ser Pro Thr Thr Thr Thr Thr Thr
            115                 120                 125

Thr Glu Gln Pro Glu Asp Glu Phe Glu Cys Pro Thr Arg Phe Gly Tyr
        130                 135                 140

Phe Ala Asp Pro Lys Asp Pro Cys Lys Phe Tyr Ile Cys Ser Asn Trp
145                 150                 155                 160

Glu Ala Ile His Lys Ser Cys Pro Gly Asn Thr Arg Trp Asn Glu Lys
                165                 170                 175
```

Glu Leu Thr Cys Thr
        180

<210> SEQ ID NO 55
<211> LENGTH: 876
<212> TYPE: PRT
<213> ORGANISM: Artificial Sequence
<220> FEATURE:
<223> OTHER INFORMATION: Der f 11_iso1

<400> SEQUENCE: 55

Met Ser Ala Arg Thr Ala Lys Tyr Met Tyr Arg Ser Ser Gly Ala Gly
1               5                   10                  15

Ala Ser Gly Asp Ile Ser Val Glu Tyr Gly Thr Asp Leu Gly Ala Leu
            20                  25                  30

Thr Arg Leu Glu Asp Lys Ile Arg Leu Leu Ser Asp Asp Leu Glu Ser
        35                  40                  45

Glu Arg Glu Met Arg Gln Arg Ile Glu Arg Glu Lys Ala Glu Leu Gln
    50                  55                  60

Ile Gln Val Met Ser Leu Gly Glu Arg Leu Glu Glu Ala Glu Gly Ser
65                  70                  75                  80

Ser Glu Ser Val Thr Glu Met Asn Lys Lys Arg Asp Ser Glu Leu Ala
                85                  90                  95

Lys Leu Arg Lys Leu Leu Glu Asp Val His Ile Glu Ser Glu Glu Thr
            100                 105                 110

Ala His His Leu Arg Gln Lys His Gln Ala Ala Ile Gln Glu Met Gln
        115                 120                 125

Asp Gln Leu Asp Gln Leu Gln Lys Ala Lys Asn Lys Ser Asp Lys Glu
    130                 135                 140

Lys Gln Lys Phe Gln Ala Glu Val Phe Glu Leu Leu Ala Gln Leu Glu
145                 150                 155                 160

Thr Ala Asn Lys Glu Lys Leu Thr Ala Leu Lys Asn Val Glu Lys Leu
                165                 170                 175

Glu Tyr Thr Val His Glu Leu Asn Ile Lys Ile Glu Glu Ile Asn Arg
            180                 185                 190

Thr Val Ile Glu Leu Thr Ser His Lys Gln Arg Leu Ser Gln Glu Asn
        195                 200                 205

Thr Glu Leu Ile Lys Glu Val His Glu Val Lys Leu Gln Leu Asp Asn
    210                 215                 220

Ala Asn His Leu Lys Thr Gln Ile Ala Gln Leu Glu Asp Thr Arg
225                 230                 235                 240

His Arg Leu Glu Glu Glu Glu Arg Lys Arg Ala Ser Leu Glu Asn His
                245                 250                 255

Ala His Thr Leu Glu Val Glu Leu Ser Leu Lys Val Gln Leu Asp
            260                 265                 270

Glu Glu Ser Glu Ala Arg Leu Glu Leu Glu Arg Gln Leu Thr Lys Ala
        275                 280                 285

Asn Gly Asp Ala Ala Ser Trp Lys Ser Lys Tyr Glu Ala Glu Leu Gln
    290                 295                 300

Ala His Ala Asp Glu Val Glu Glu Leu Arg Arg Lys Met Ala Gln Lys
305                 310                 315                 320

Ile Ser Glu Tyr Glu Glu Gln Leu Glu Ala Leu Leu Asn Lys Cys Ser
                325                 330                 335

Ser Leu Glu Lys Gln Lys Ser Arg Leu Gln Ser Glu Val Glu Val Leu
            340                 345                 350

```
Ile Met Asp Leu Glu Lys Ala Thr Ala His Ala Gln Gln Leu Glu Lys
            355                 360                 365

Arg Val Ala Gln Leu Glu Lys Ile Asn Leu Asp Leu Lys Asn Lys Leu
    370                 375                 380

Glu Glu Val Thr Met Leu Met Glu Gln Ala Gln Lys Glu Leu Arg Val
385                 390                 395                 400

Lys Ile Ala Glu Leu Gln Lys Leu Gln His Glu Tyr Glu Lys Leu Arg
                405                 410                 415

Asp Gln Arg Asp Gln Leu Ala Arg Glu Asn Lys Lys Leu Thr Asp Asp
            420                 425                 430

Leu Ala Glu Ala Lys Ser Gln Leu Asn Asp Ala His Arg Arg Ile His
    435                 440                 445

Glu Gln Glu Ile Glu Ile Lys Arg Leu Glu Asn Glu Arg Asp Glu Leu
                450                 455                 460

Ser Ala Ala Tyr Lys Glu Ala Glu Thr Leu Arg Lys Gln Glu Glu Ala
465                 470                 475                 480

Lys Asn Gln Arg Leu Ile Ala Glu Leu Ala Gln Val Arg His Asp Tyr
                485                 490                 495

Glu Lys Arg Leu Ala Gln Lys Asp Glu Glu Ile Glu Ala Leu Arg Lys
            500                 505                 510

Gln Tyr Gln Ile Glu Ile Glu Gln Leu Asn Met Arg Leu Ala Glu Ala
    515                 520                 525

Glu Ala Lys Leu Lys Thr Glu Ile Ala Arg Leu Lys Lys Lys Tyr Gln
530                 535                 540

Ala Gln Ile Thr Glu Leu Glu Leu Ser Leu Asp Ala Ala Asn Lys Ala
545                 550                 555                 560

Asn Ile Asp Leu Gln Lys Thr Ile Lys Lys Gln Ala Leu Gln Ile Thr
                565                 570                 575

Ser Glu Leu Gln Ala His Tyr Asp Glu Val His Arg Gln Leu Gln Gln
            580                 585                 590

Ala Val Asp Gln Leu Gly Val Thr Gln Arg Arg Cys Gln Ala Leu Gln
    595                 600                 605

Ala Glu Leu Glu Glu Met Arg Ile Ala Leu Glu Gln Ala Asn Arg Ala
    610                 615                 620

Lys Arg Gln Ala Glu Gln Leu His Glu Glu Ala Val Arg Val Asn
625                 630                 635                 640

Glu Leu Thr Thr Ile Asn Val Asn Leu Ala Ser Ala Lys Ser Lys Leu
                645                 650                 655

Glu Ser Glu Phe Ser Ala Leu Gln Ala Asp Tyr Asp Glu Val His Lys
            660                 665                 670

Glu Leu Arg Ile Ser Asp Glu Arg Val Gln Lys Leu Thr Ile Glu Leu
    675                 680                 685

Lys Ser Thr Lys Asp Leu Leu Ile Glu Glu Gln Glu Arg Leu Val Lys
690                 695                 700

Leu Glu Thr Val Lys Lys Ser Leu Glu Gln Glu Val Arg Thr Leu His
705                 710                 715                 720

Val Arg Ile Glu Glu Val Glu Ala Asn Ala Leu Ala Gly Gly Lys Arg
                725                 730                 735

Val Ile Ala Lys Leu Glu Ser Arg Ile Arg Asp Val Glu Ile Glu Val
            740                 745                 750

Glu Glu Glu Arg Arg Arg His Ala Glu Thr Asp Lys Met Leu Arg Lys
    755                 760                 765
```

Lys Asp His Arg Val Lys Glu Leu Leu Gln Asn Glu Glu Asp His
770             775                 780

Lys Gln Ile Gln Leu Leu Gln Glu Met Thr Asp Lys Leu Asn Glu Lys
785             790                 795                 800

Val Lys Val Tyr Lys Arg Gln Met Gln Glu Gln Glu Gly Met Ser Gln
        805                 810                 815

Gln Asn Leu Thr Arg Val Arg Arg Phe Gln Arg Glu Leu Glu Ala Ala
            820                 825                 830

Glu Asp Arg Ala Asp Gln Ala Glu Ser Asn Leu Ser Phe Ile Arg Ala
            835                 840                 845

Lys His Arg Ser Trp Val Thr Thr Ser Gln Val Pro Gly Gly Thr Arg
850                 855                 860

Gln Val Phe Thr Thr Gln Glu Glu Thr Thr Asn Tyr
865                 870                 875

<210> SEQ ID NO 56
<211> LENGTH: 556
<212> TYPE: PRT
<213> ORGANISM: Artificial Sequence
<220> FEATURE:
<223> OTHER INFORMATION: Der f 15_iso1

<400> SEQUENCE: 56

Met Lys Thr Ile Tyr Ala Ile Leu Ser Ile Met Ala Cys Ile Gly Leu
1               5                   10                  15

Met Asn Ala Ser Ile Lys Arg Asp His Asn Asp Tyr Ser Lys Asn Pro
            20                  25                  30

Met Arg Ile Val Cys Tyr Val Gly Thr Trp Ser Val Tyr His Lys Val
        35                  40                  45

Asp Pro Tyr Thr Ile Glu Asp Ile Asp Pro Phe Lys Cys Thr His Leu
    50                  55                  60

Met Tyr Gly Phe Ala Lys Ile Asp Glu Tyr Lys Tyr Thr Ile Gln Val
65              70                  75                  80

Phe Asp Pro Tyr Gln Asp Asp Asn His Asn Ser Trp Glu Lys Arg Gly
            85                  90                  95

Tyr Glu Arg Phe Asn Asn Leu Arg Leu Lys Asn Pro Glu Leu Thr Thr
        100                 105                 110

Met Ile Ser Leu Gly Gly Trp Tyr Glu Gly Ser Glu Lys Tyr Ser Asp
    115                 120                 125

Met Ala Ala Asn Pro Thr Tyr Arg Gln Gln Phe Ile Gln Ser Val Leu
130                 135                 140

Asp Phe Leu Gln Glu Tyr Lys Phe Asp Gly Leu Asp Leu Asp Trp Glu
145                 150                 155                 160

Tyr Pro Gly Ser Arg Leu Gly Asn Pro Lys Ile Asp Lys Gln Asn Tyr
            165                 170                 175

Leu Ala Leu Val Arg Glu Leu Lys Asp Ala Phe Glu Pro His Gly Tyr
        180                 185                 190

Leu Leu Thr Ala Ala Val Ser Pro Gly Lys Asp Lys Ile Asp Arg Ala
    195                 200                 205

Tyr Asp Ile Lys Glu Leu Asn Lys Leu Phe Asp Trp Met Asn Val Met
210                 215                 220

Thr Tyr Asp Tyr His Gly Gly Trp Glu Asn Phe Tyr Gly His Asn Ala
225                 230                 235                 240

Pro Leu Tyr Lys Arg Pro Asp Glu Thr Asp Glu Leu His Thr Tyr Phe
            245                 250                 255

Asn Val Asn Tyr Thr Met His Tyr Tyr Leu Asn Asn Gly Ala Thr Arg
            260                 265                 270

Asp Lys Leu Val Met Gly Val Pro Phe Tyr Gly Arg Ala Trp Ser Ile
            275                 280                 285

Glu Asp Arg Ser Lys Leu Lys Leu Gly Asp Pro Ala Lys Gly Met Ser
        290                 295                 300

Pro Pro Gly Phe Ile Ser Gly Glu Gly Val Leu Ser Tyr Ile Glu
305                 310                 315                 320

Leu Cys Gln Leu Phe Gln Lys Glu Glu Trp His Ile Gln Tyr Asp Glu
                325                 330                 335

Tyr Tyr Asn Ala Pro Tyr Gly Tyr Asn Asp Lys Ile Trp Val Gly Tyr
            340                 345                 350

Asp Asp Leu Ala Ser Ile Ser Cys Lys Leu Ala Phe Leu Lys Glu Leu
            355                 360                 365

Gly Val Ser Gly Val Ile Val Trp Ser Leu Glu Asn Asp Asp Phe Lys
        370                 375                 380

Gly His Cys Gly Pro Lys Asn Pro Leu Leu Asn Lys Val His Asn Met
385                 390                 395                 400

Ile Asn Gly Asp Glu Lys Asn Ser Phe Glu Cys Ile Leu Gly Pro Ser
                405                 410                 415

Thr Thr Thr Pro Thr Pro Thr Thr Thr Pro Thr Thr Thr Pro Thr Pro
            420                 425                 430

Ser Pro Thr Thr Pro Thr Pro Ser Pro Thr Thr Pro Thr Thr Thr Pro
        435                 440                 445

Ser Pro Thr Thr Pro Thr Pro Ser Pro Thr Thr Pro Thr Thr Thr Pro
450                 455                 460

Ser Pro Thr Thr Pro Thr Pro Thr Thr Pro Thr Pro Thr Pro Thr Thr
465                 470                 475                 480

Ser Thr Pro Ser Pro Thr Thr Glu His Thr Ser Glu Thr Pro Lys
            485                 490                 495

Tyr Thr Thr Tyr Val Asp Gly His Leu Ile Lys Cys Tyr Lys Glu Gly
            500                 505                 510

Asp Ile Pro His Pro Thr Asn Ile His Lys Tyr Leu Val Cys Glu Phe
            515                 520                 525

Val Asn Gly Gly Trp Trp Val His Ile Met Pro Cys Pro Pro Gly Thr
        530                 535                 540

Ile Trp Cys Gln Glu Lys Leu Thr Cys Ile Gly Glu
545                 550                 555

<210> SEQ ID NO 57
<211> LENGTH: 296
<212> TYPE: PRT
<213> ORGANISM: Artificial Sequence
<220> FEATURE:
<223> OTHER INFORMATION: Der f 32_iso1

<400> SEQUENCE: 57

Met Ser Thr Thr Asn Tyr Ser Val Asp His Arg Gly Ser Phe Asn Ser
1               5                   10                  15

Leu Asp Tyr Arg Ile Tyr Phe Lys Asp Asn Ser Asn Gly Lys Ile Ile
            20                  25                  30

Ser Pro Trp His Asp Ile Pro Leu Phe Val Asp Lys Ser Ala Lys His
        35                  40                  45

Tyr Asn Met Val Val Glu Ile Pro Arg Trp Thr Asn Glu Lys Met Glu
    50                  55                  60

```
Ile Ala Thr Ala Glu Pro Met Ser Pro Ile Lys Gln Asp Ile Lys Lys
 65                  70                  75                  80

Gly Ala Leu Arg Tyr Val Lys Asn Val Phe Pro His Lys Gly Tyr Ile
                 85                  90                  95

Trp Asn Tyr Gly Ala Phe Pro Gln Thr Trp Glu Asn Pro Asn His Ile
            100                 105                 110

Asp Gln Asp Thr Lys Thr Lys Gly Asp Asn Asp Pro Ile Asp Val Ile
        115                 120                 125

Glu Ile Gly Ser Arg Val Ala Lys Arg Gly Asp Val Pro Val Lys
    130                 135                 140

Ile Leu Gly Thr Ile Ala Leu Ile Asp Glu Gly Glu Thr Asp Trp Lys
145                 150                 155                 160

Ile Ile Ala Ile Asp Thr Arg Asp Glu Leu Ala Ser Gln Met Asn Asn
                165                 170                 175

Val Asp Asp Val Glu Lys Leu Leu Pro Gly Leu Leu Arg Ala Thr Val
            180                 185                 190

Glu Trp Phe Lys Ile Tyr Lys Ile Pro Asp Gly Lys Pro Ala Asn Lys
        195                 200                 205

Phe Ala Phe Asn Gly Glu Ala Lys Asp Arg Glu Phe Ala Glu Lys Ile
210                 215                 220

Val Glu Glu Thr His Gln Tyr Trp Gln Glu Met Met Glu Asn Lys Ser
225                 230                 235                 240

Gly Glu His Lys Leu Asp Leu Lys Asn Val Thr Leu Gly Asn Ser Phe
                245                 250                 255

Ser Ile Asn Asp Glu Gln Ala Lys Gln Phe Leu Glu Thr Arg Pro Ser
            260                 265                 270

Ser Asp Ala Val Glu Pro Thr Pro Ile Ala Asp Gln Val Ala Ile Asp
        275                 280                 285

Lys Trp His His Val Lys Leu Ile
            290                 295

<210> SEQ ID NO 58
<211> LENGTH: 247
<212> TYPE: PRT
<213> ORGANISM: Artificial Sequence
<220> FEATURE:
<223> OTHER INFORMATION: Der f 25_iso1

<400> SEQUENCE: 58

Met Val Arg Lys Phe Phe Val Gly Gly Asn Trp Lys Met Asn Gly Ser
1               5                   10                  15

Arg Ala Thr Asn Glu Asp Leu Ile Lys Thr Leu Ser Asn Gly Pro Leu
            20                  25                  30

Asp Pro Asn Thr Asp Val Val Val Gly Val Pro Ser Ile Tyr Met Ala
        35                  40                  45

Glu Val Arg Gln Lys Leu Pro Lys Thr Ile Gly Val Ala Ala Gln Asn
    50                  55                  60

Cys Tyr Lys Val Pro Lys Gly Ala Phe Thr Gly Glu Ile Ser Pro Ala
 65                  70                  75                  80

Met Ile Lys Asp Val Gly Ala Glu Trp Val Ile Leu Gly His Ser Glu
                 85                  90                  95

Arg Arg Asn Val Phe Gly Glu Ser Asp Gln Leu Ile Gly Glu Lys Val
            100                 105                 110

Glu His Ala Leu Gln Glu Gly Leu His Val Ile Ala Cys Ile Gly Glu
        115                 120                 125
```

```
Leu Leu Glu Glu Arg Glu Ala Gly Lys Thr Thr Glu Val Val Phe Arg
            130                 135                 140

Gln Thr Gln Val Ile Ser Lys His Val Lys Asp Trp Ser Lys Val Val
145                 150                 155                 160

Leu Ala Tyr Glu Pro Val Trp Ala Ile Gly Thr Gly Lys Thr Ala Ser
                165                 170                 175

Pro Gln Gln Ala Gln Glu Val His Gln Lys Leu Arg Gln Trp Phe Ser
                180                 185                 190

Glu Asn Val Ser Pro Gln Ile Ala Glu Thr Ile Arg Ile Ile Tyr Gly
            195                 200                 205

Gly Ser Val Thr Ala Asn Asn Ala Lys Glu Leu Ala Ser Gln Ala Asp
210                 215                 220

Val Asp Gly Phe Leu Val Gly Gly Ala Ser Leu Lys Pro Glu Phe Val
225                 230                 235                 240

Gln Ile Val Asn Ala Arg Gln
                245

<210> SEQ ID NO 59
<211> LENGTH: 480
<212> TYPE: PRT
<213> ORGANISM: Artificial Sequence
<220> FEATURE:
<223> OTHER INFORMATION: Der f 16_iso1

<400> SEQUENCE: 59

Met Ala Ala His Asp Lys Asn Phe Asp Val Ile Pro Ile Gly His Thr
1               5                   10                  15

Phe Phe Phe Ile Trp Arg Ile Lys Gln Phe Glu Leu Val Pro Val Pro
                20                  25                  30

Lys Glu Asp Tyr Gly Lys Phe Tyr Lys Gly Asp Cys Tyr Ile Val Ala
            35                  40                  45

Cys Cys Thr Glu Asn Pro Thr Gly Gly His Ser Lys Met Glu Ser Lys
50                  55                  60

Pro Ile Leu Asn Gly His Gly Tyr Cys His Ile His Phe Trp Ile Gly
65                  70                  75                  80

Ser Glu Ser Thr Lys Asp Glu Ala Gly Val Ala Ala Ile Lys Ser Val
                85                  90                  95

Glu Leu Asp Asp Phe Leu Gly Gly Tyr Pro Val Gln His Arg Glu Ile
            100                 105                 110

Glu Glu Phe Glu Ser Arg Gln Phe Ser Ser Tyr Phe Lys Asn Gly Ile
        115                 120                 125

Ile Tyr Leu Lys Gly Gly Tyr Glu Ser Gly Phe Thr Lys Met Ile Asp
130                 135                 140

Glu Leu Lys Pro Ser Leu Leu His Val Lys Gly Lys Lys Arg Pro Ile
145                 150                 155                 160

Val Tyr Glu Cys Ala Glu Ile Ser Trp Lys Val Met Asn Asn Gly Asp
                165                 170                 175

Val Phe Ile Leu Leu Val Pro Asn Phe Val Phe Val Trp Thr Gly Lys
            180                 185                 190

His Ser Asn Arg Met Glu Arg Thr Thr Ala Ile Arg Val Ala Asn Asp
        195                 200                 205

Leu Lys Ser Glu Leu Asn Arg Phe Lys Leu Ser Ser Val Ile Leu Glu
210                 215                 220

Asp Gly Lys Glu Val Glu Gln Thr Ser Gly Ala Glu Tyr Asp Ala Phe
225                 230                 235                 240
```

```
Asn Lys Ala Leu Ser Leu Asp Lys Lys Asp Ile Asp Leu Lys Gln Met
            245                 250                 255
Pro Lys Gly Tyr Asp Tyr Ala Ala Ser Asp Lys Ser Phe Glu Ser His
        260                 265                 270
Glu Arg Ser Phe Val Thr Leu Tyr Lys Cys Phe Glu Gly Thr Glu Thr
    275                 280                 285
Ile Asp Ile Ser Phe Val Lys Asn Gly Pro Leu Ser Arg Ala Asp Leu
290                 295                 300
Asp Thr Asn Asp Thr Phe Ile Val Glu Asn Gly Ser Glu Gly Leu Trp
305                 310                 315                 320
Val Trp Val Gly Lys Lys Ala Thr Gln Lys Glu Arg Gln Ser Ala Ile
                325                 330                 335
Lys Tyr Ala Met Glu Leu Ile Asn Lys Lys Tyr Pro Asn Asn Thr
            340                 345                 350
Pro Val Thr Lys Val Leu Glu Gly Asp Glu Ser Val Glu Phe Lys Ser
        355                 360                 365
Leu Phe Glu Ser Trp Gln Met Ser Glu Gln Glu Lys Ile Thr Ser Ala
    370                 375                 380
Arg Leu Phe Arg Val Ser Arg Asn Gly Ile Phe Lys Gln Val Ala Asn
385                 390                 395                 400
Tyr Glu Pro Asp Asp Leu Glu Glu Asp Asn Ile Met Ile Leu Asp Val
                405                 410                 415
Met Asp Lys Ile Tyr Val Trp Ile Gly Asn Gln Phe Ala Glu Arg Ile
            420                 425                 430
Ala Asp Glu Ala His Val Asp Lys Val Ala Gln Arg Phe Ile Gln Glu
        435                 440                 445
Asp Lys Ser Gly Arg Lys Phe Arg Pro Asn Gln Ile Ile Lys Leu Lys
    450                 455                 460
Gln Gly Ser Glu Asp Gly Ala Phe Lys Ser Tyr Phe Pro Lys Trp Asn
465                 470                 475                 480

<210> SEQ ID NO 60
<211> LENGTH: 164
<212> TYPE: PRT
<213> ORGANISM: Artificial Sequence
<220> FEATURE:
<223> OTHER INFORMATION: Der f 26_iso1

<400> SEQUENCE: 60

Met Ala Leu Pro Arg Val Phe Phe Asp Ile Ala Ala Asp Asn Gln Pro
1               5                   10                  15
Leu Gly Arg Ile Val Ile Glu Leu Arg Ser Asp Val Val Pro Lys Thr
            20                  25                  30
Ala Glu Asn Phe Arg Ala Leu Cys Thr Gly Glu Lys Gly Phe Gly Phe
        35                  40                  45
Lys Ser Ser Ser Phe His Arg Ile Ile Pro Asn Phe Met Ile Gln Gly
    50                  55                  60
Gly Asp Phe Thr Asn His Asn Gly Thr Gly Lys Ser Ile Tyr Gly
65                  70                  75                  80
Asn Lys Phe Ala Asp Glu Asn Phe Thr Leu Gln His Thr Gly Pro Gly
                85                  90                  95
Ile Met Ser Met Ala Asn Ala Gly Pro Asn Thr Asn Gly Ser Gln Phe
            100                 105                 110
Phe Ile Thr Thr Val Lys Thr Thr Trp Leu Asp Gly Lys His Val Val
        115                 120                 125
```

```
Phe Gly Ser Val Val Glu Gly Met Asp Ile Val Lys Val Glu Ser
    130                 135                 140

Tyr Gly Ser Gln Ser Gly Lys Pro Ser Lys Val Thr Ile Ala Asn
145                 150                 155                 160

Cys Gly Gln Leu

<210> SEQ ID NO 61
<211> LENGTH: 104
<212> TYPE: PRT
<213> ORGANISM: Artificial Sequence
<220> FEATURE:
<223> OTHER INFORMATION: Der f 23_iso2

<400> SEQUENCE: 61

Met Lys Phe Asn Ile Thr Ile Ala Phe Val Ser Leu Ala Ile Leu Ile
1               5                   10                  15

His Ser Ser Tyr Ala Asp Ile Asp His Phe Asp Asn Asp Gln Asn
            20                  25                  30

Ser Ser Thr Ser Arg Pro Asp Asp Pro Thr Thr Met Ile Asp Val
        35                  40                  45

Gln Thr Thr Thr Val Gln Pro Ser Asp Glu Phe Glu Cys Pro Thr Arg
50                  55                  60

Phe Gly Tyr Phe Ala Asp Pro Lys Asp Pro Cys Lys Phe Tyr Ile Cys
65                  70                  75                  80

Ser Asn Trp Glu Ala Ile His Lys Ser Cys Pro Gly Asn Thr Arg Trp
            85                  90                  95

Asn Glu Lys Glu Leu Thr Cys Thr
            100

<210> SEQ ID NO 62
<211> LENGTH: 131
<212> TYPE: PRT
<213> ORGANISM: Artificial Sequence
<220> FEATURE:
<223> OTHER INFORMATION: Der f 13_iso1

<400> SEQUENCE: 62

Met Ala Ser Ile Glu Gly Lys Tyr Lys Leu Gln Ser Glu Lys Phe
1               5                   10                  15

Asp Glu Phe Leu Asp Lys Leu Gly Val Gly Phe Met Val Lys Thr Ala
            20                  25                  30

Ala Lys Thr Leu Lys Pro Thr Phe Glu Val Ala Ile Glu Asn Asp Gln
        35                  40                  45

Tyr Ile Phe Arg Ser Leu Ser Thr Phe Lys Asn Thr Glu Ala Lys Phe
50                  55                  60

Lys Leu Gly Glu Glu Phe Glu Glu Asp Arg Ala Asp Gly Lys Arg Val
65                  70                  75                  80

Lys Thr Val Ile Gln Lys Glu Gly Asp Asn Lys Phe Val Gln Thr Gln
            85                  90                  95

Phe Gly Asp Lys Glu Val Lys Ile Ile Arg Glu Phe Asn Gly Asp Glu
            100                 105                 110

Val Val Val Thr Ala Ser Cys Asp Gly Val Thr Ser Val Arg Thr Tyr
            115                 120                 125

Lys Arg Ile
    130

<210> SEQ ID NO 63
<211> LENGTH: 213
```

```
<212> TYPE: PRT
<213> ORGANISM: Artificial Sequence
<220> FEATURE:
<223> OTHER INFORMATION: Der f 7_iso1

<400> SEQUENCE: 63
```

| | | | | | | | | | | | | | | |
|---|---|---|---|---|---|---|---|---|---|---|---|---|---|---|
| Met | Met | Lys | Phe | Leu | Leu | Ile | Ala | Ala | Val | Phe | Ala | Val | Ser |
| 1 | | | | 5 | | | | | 10 | | | | | 15 |

Ala Asp Pro Ile His Tyr Asp Lys Ile Thr Glu Glu Ile Asn Lys Ala
            20                  25                  30

Ile Asp Asp Ala Ile Ala Ile Glu Lys Ser Glu Thr Ile Asp Pro
        35                  40                  45

Met Lys Val Pro Asp His Thr Asp Lys Phe Glu Arg His Val Gly Ile
 50                  55                  60

Leu Asp Phe Lys Gly Glu Leu Ala Met Arg Asn Ile Glu Ala Arg Gly
 65                  70                  75                  80

Leu Lys Gln Met Lys Arg Gln Gly Asp Ala Asn Val Lys Gly Glu Glu
                 85                  90                  95

Gly Ile Val Lys Ala His Leu Leu Ile Gly Val His Asp Asp Ile Val
                100                 105                 110

Ser Met Glu Tyr Asp Leu Ala Tyr Lys Leu Gly Asp Leu His Pro Asn
            115                 120                 125

Thr His Val Ile Ser Asp Ile Gln Asp Phe Val Val Ala Leu Ser Leu
130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
    210

```
<210> SEQ ID NO 64
<211> LENGTH: 427
<212> TYPE: PRT
<213> ORGANISM: Artificial Sequence
<220> FEATURE:
<223> OTHER INFORMATION: Der f 27_iso1

<400> SEQUENCE: 64
```

Met Lys Phe Phe Leu Leu Ser Phe Val Leu Met Ile Val Ala Ala Thr
1               5                   10                  15

Ala Thr Tyr Ala Ala His Val Gly Ser Gly Ser Arg Asp Asn Asn Asn
            20                  25                  30

Asn Lys Pro Val Pro Ala Glu Gly Phe Ala Lys Ala Ser Asn Glu Phe
        35                  40                  45

Gly Phe His Leu Leu Lys Glu Val Ile Gln His Arg Ser Ser Ser Gly
 50                  55                  60

Ser Arg Gly Ser Ser Glu Asn Val Leu Phe Ser Pro Tyr Ser Val Ala
 65                  70                  75                  80

Val Ala Leu Ser Met Val His Gln Gly Thr Gln Gly Ser Thr Ala Glu
                 85                  90                  95

Gln Phe Lys Arg Val Leu Tyr Tyr Asp Arg Val Gln Gln Leu Asn Gly
            100                 105                 110

Gly Glu Tyr Gln Thr Val Ala Asn Ser Val Lys Gln Ile Gln Asn Gln
            115                 120                 125

Ile Lys Gln Ser Asp Gln Ser Asn Gln Phe Asp Trp Gly Asn Met Leu
    130                 135                 140

Met Val Asp Gln Gln Ile Pro Val Lys Asp Gln Tyr Lys Lys Ile Ile
145                 150                 155                 160

Glu Gln Tyr Tyr Asp Gly Gln Val Met Ser Val Asp Phe Arg Lys Glu
                165                 170                 175

Ser Lys Asn Val Met Glu Arg Ile Asn Gln Phe Val Ser Asn Lys Thr
            180                 185                 190

His Gly Leu Ile Asp Arg Met Leu Glu Gln Pro Pro Ser Ala Asp Thr
        195                 200                 205

Gly Leu Ala Leu Ile Asn Ala Val Tyr Phe Lys Gly Glu Trp Leu Lys
    210                 215                 220

Pro Phe Asp Ser Met Arg Thr Glu Gln Ser Val Phe Tyr Gly His His
225                 230                 235                 240

Gly Gln Glu Tyr Lys Asn Val Gln Tyr Ile Asn Gly Gln Gly Pro Tyr
                245                 250                 255

Gly Tyr Val Glu Val Pro Gln Trp Asn Ser Asp Leu Ile Gln Leu Pro
            260                 265                 270

Tyr Lys Gly Glu Asp Ile Ala Phe Tyr Gly Val Leu Pro Arg Glu Arg
        275                 280                 285

Asn Tyr Asp Leu Asp Lys Ile Arg Gln Ser Ile Asn Ser Thr Phe Val
    290                 295                 300

Asp Glu Ile Val Gly Gln Ile Thr Gly Ser Gln Ser Thr Val Tyr
305                 310                 315                 320

Phe Pro Lys Ile Glu Leu Ser Thr Ser Tyr Gln Leu Pro Glu Ile Leu
                325                 330                 335

Lys Ser Met Gly Leu Gln Asp Val Phe Thr Glu Ser Ala Asp Leu Ser
            340                 345                 350

Gly Ile Thr Asp Lys Lys Pro Met Lys Ile Asp Asp Ala Ile His Lys
        355                 360                 365

Ala Lys Leu Ile Leu Asn Glu Gln Gly Thr Glu Ala Gly Ala Gly Thr
    370                 375                 380

Tyr Ile Gln Met Ala Val Leu Ser Ala Leu Glu Thr Ser His Thr Phe
385                 390                 395                 400

Arg Phe Asp His Pro Phe Met Tyr Phe Ile Arg His Leu Pro Thr Gly
                405                 410                 415

Gln Ile Leu Phe Leu Gly Glu Ile His Asp Phe
            420                 425

<210> SEQ ID NO 65
<211> LENGTH: 213
<212> TYPE: PRT
<213> ORGANISM: Artificial Sequence
<220> FEATURE:
<223> OTHER INFORMATION: Der f 7_iso2

<400> SEQUENCE: 65

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
            20                  25                  30

Ile Asp Asp Ala Ile Ala Ala Ile Glu Lys Ser Glu Thr Ile Asp Pro
        35                  40                  45

```
Met Lys Val Pro Asp His Thr Asp Lys Phe Glu Arg His Val Gly Ile
         50                  55                  60

Leu Asp Phe Lys Gly Glu Leu Ala Met Arg Asn Ile Glu Ala Arg Gly
 65                  70                  75                  80

Leu Lys Gln Met Lys Arg Gln Gly Asp Ala Asn Val Lys Gly Glu Glu
                 85                  90                  95

Gly Ile Val Lys Ala His Leu Leu Ile Gly Val His Asp Asp Ile Val
                100                 105                 110

Ser Met Glu Tyr Asp Leu Ala Tyr Lys Leu Gly Asp Leu His Pro Asn
                115                 120                 125

Thr His Val Ile Ser Asp Ile Gln Asp Phe Val Val Ala Leu Ser Leu
                130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Gly Val Leu Ser Asp Val Leu Thr Ala Ile Phe Gln Asp
                180                 185                 190

Thr Val Arg Lys Glu Met Thr Lys Val Leu Ala Pro Ala Phe Lys Arg
                195                 200                 205

Glu Leu Glu Lys Asn
                210

<210> SEQ ID NO 66
<211> LENGTH: 164
<212> TYPE: PRT
<213> ORGANISM: Artificial Sequence
<220> FEATURE:
<223> OTHER INFORMATION: Der f 29_iso1

<400> SEQUENCE: 66

Met Ala Leu Pro Arg Val Phe Phe Asp Ile Ala Ala Asp Asn Gln Pro
 1               5                  10                  15

Leu Gly Arg Ile Val Ile Glu Leu Arg Ser Asp Val Val Pro Lys Thr
                20                  25                  30

Ala Glu Asn Phe Arg Ala Leu Cys Thr Gly Glu Lys Gly Phe Gly Phe
                35                  40                  45

Lys Ser Ser Ser Phe His Arg Ile Ile Pro Asn Phe Met Ile Gln Gly
                50                  55                  60

Gly Asp Phe Thr Asn His Asn Gly Thr Gly Lys Ser Ile Tyr Gly
 65                  70                  75                  80

Asn Lys Phe Ala Asp Glu Asn Phe Thr Leu Gln His Thr Gly Pro Gly
                 85                  90                  95

Ile Met Ser Met Ala Asn Ala Gly Pro Asn Thr Asn Gly Ser Gln Phe
                100                 105                 110

Phe Ile Thr Thr Val Lys Thr Thr Trp Leu Asp Gly Lys His Val Val
                115                 120                 125

Phe Gly Ser Val Val Glu Gly Met Asp Ile Val Lys Lys Val Glu Ser
                130                 135                 140

Tyr Gly Ser Gln Ser Gly Lys Pro Ser Lys Val Thr Ile Ala Asn
145                 150                 155                 160

Cys Gly Gln Leu

<210> SEQ ID NO 67
<211> LENGTH: 462
```

```
<212> TYPE: PRT
<213> ORGANISM: Artificial Sequence
<220> FEATURE:
<223> OTHER INFORMATION: Der f 18_iso1

<400> SEQUENCE: 67

Met Thr Arg Phe Ser Leu Thr Val Leu Ala Val Leu Ala Ala Cys Phe
1               5                   10                  15

Gly Ser Asn Ile Arg Pro Asn Val Ala Thr Leu Glu Pro Lys Thr Val
            20                  25                  30

Cys Tyr Tyr Glu Ser Trp Val His Trp Arg Gln Gly Glu Gly Lys Met
        35                  40                  45

Asp Pro Glu Asp Ile Asp Thr Ser Leu Cys Thr His Ile Val Tyr Ser
    50                  55                  60

Tyr Phe Gly Ile Asp Ala Ala Thr His Glu Ile Lys Leu Leu Asp Glu
65                  70                  75                  80

Tyr Leu Met Lys Asp Leu His Asp Met Glu His Phe Thr Gln His Lys
                85                  90                  95

Gly Asn Ala Lys Ala Met Ile Ala Val Gly Ser Thr Met Ser Asp
            100                 105                 110

Gln Phe Ser Lys Thr Ala Ala Val Glu His Tyr Arg Glu Thr Phe Val
        115                 120                 125

Val Ser Thr Val Asp Leu Met Thr Arg Tyr Gly Phe Asp Gly Val Met
    130                 135                 140

Ile Asp Trp Ser Gly Met Gln Ala Lys Asp Ser Asp Asn Phe Ile Lys
145                 150                 155                 160

Leu Leu Asp Lys Phe Asp Glu Lys Phe Ala His Thr Ser Phe Val Met
                165                 170                 175

Gly Val Thr Leu Pro Ala Thr Ile Ala Ser Tyr Asp Asn Tyr Asn Ile
            180                 185                 190

Pro Ala Ile Ser Asn Tyr Val Asp Phe Met Asn Val Leu Ser Leu Asp
        195                 200                 205

Tyr Thr Gly Ser Trp Ala His Thr Val Gly His Ala Ser Pro Phe Pro
    210                 215                 220

Glu Gln Leu Lys Thr Leu Glu Ala Tyr His Lys Arg Gly Ala Pro Arg
225                 230                 235                 240

His Lys Met Val Met Ala Val Pro Phe Tyr Ala Arg Thr Trp Ile Leu
                245                 250                 255

Glu Lys Met Asn Lys Gln Asp Ile Gly Asp Lys Ala Ser Gly Pro Gly
            260                 265                 270

Pro Arg Gly Gln Phe Thr Gln Thr Asp Gly Phe Leu Ser Tyr Asn Glu
        275                 280                 285

Leu Cys Val Gln Ile Gln Ala Glu Thr Asn Ala Phe Thr Ile Thr Arg
    290                 295                 300

Asp His Asp Asn Thr Ala Ile Tyr Ala Val Tyr Val His Ser Asn His
305                 310                 315                 320

Ala Glu Trp Ile Ser Phe Glu Asp Arg His Thr Leu Gly Glu Lys Ala
                325                 330                 335

Lys Asn Ile Thr Gln Gln Gly Tyr Ala Gly Met Ser Val Tyr Thr Leu
            340                 345                 350

Ser Asn Glu Asp Val His Gly Val Cys Gly Asp Lys Asn Pro Leu Leu
        355                 360                 365

His Ala Ile Gln Ser Asn Tyr Tyr His Gly Val Val Thr Glu Pro Thr
    370                 375                 380
```

```
Val Val Thr Leu Pro Pro Val Thr His Thr Glu His Val Thr Asp
385                 390                 395                 400

Ile Pro Gly Val Phe His Cys His Glu Glu Gly Phe Phe Arg Asp Lys
                405                 410                 415

Thr Tyr Cys Ala Thr Tyr Tyr Glu Cys Lys Lys Gly Asp Phe Gly Leu
            420                 425                 430

Glu Lys Thr Val His His Cys Ala Asn His Leu Gln Ala Phe Asp Glu
        435                 440                 445

Val Ser Arg Thr Cys Ile Asp His Thr Lys Ile Pro Gly Cys
    450                 455                 460
```

<210> SEQ ID NO 68
<211> LENGTH: 480
<212> TYPE: PRT
<213> ORGANISM: Artificial Sequence
<220> FEATURE:
<223> OTHER INFORMATION: Der f 16_iso2

<400> SEQUENCE: 68

```
Met Ala Ala His Asp Lys Asn Phe Asp Val Ile Pro Ile Gly His Thr
1               5                   10                  15

Phe Phe Phe Ile Trp Arg Ile Lys Gln Phe Glu Leu Val Pro Val Pro
                20                  25                  30

Lys Glu Asp Tyr Gly Lys Phe Tyr Lys Gly Asp Cys Tyr Ile Val Ala
            35                  40                  45

Cys Cys Thr Glu Asn Pro Thr Gly Gly His Ser Lys Met Glu Ser Lys
        50                  55                  60

Pro Ile Leu Asn Gly His Gly Tyr Cys His Ile His Phe Trp Ile Gly
65                  70                  75                  80

Ser Glu Ser Thr Lys Asp Glu Ala Gly Val Ala Ala Ile Lys Ser Val
                85                  90                  95

Glu Leu Asp Asp Phe Leu Gly Gly Tyr Pro Val Gln His Arg Glu Ile
                100                 105                 110

Glu Glu Phe Glu Ser Arg Gln Phe Ser Ser Tyr Phe Lys Asn Gly Ile
            115                 120                 125

Ile Tyr Leu Lys Gly Gly Tyr Glu Ser Gly Phe Thr Lys Met Ile Asp
        130                 135                 140

Glu Leu Lys Pro Ser Leu Leu His Val Lys Gly Lys Lys Arg Pro Ile
145                 150                 155                 160

Val Tyr Glu Cys Ala Glu Ile Ser Trp Lys Val Met Asn Asn Gly Asp
                165                 170                 175

Val Phe Ile Leu Leu Val Pro Asn Phe Val Phe Val Trp Thr Gly Lys
                180                 185                 190

His Ser Asn Arg Met Glu Arg Thr Thr Ala Ile Arg Val Ala Asn Asp
            195                 200                 205

Leu Lys Ser Glu Leu Asn Arg Phe Lys Leu Ser Ser Val Ile Leu Glu
210                 215                 220

Asp Gly Lys Glu Val Glu Gln Thr Ser Gly Ala Glu Tyr Asp Ala Phe
225                 230                 235                 240

Asn Lys Ala Leu Ser Leu Asp Lys Lys Asp Ile Asp Leu Lys Gln Met
                245                 250                 255

Pro Lys Gly Tyr Asp Tyr Ala Ala Ser Asp Lys Ser Phe Glu Ser His
            260                 265                 270

Glu Arg Ser Phe Val Thr Leu Tyr Lys Cys Phe Glu Gly Thr Glu Thr
        275                 280                 285
```

```
Ile Asp Ile Ser Phe Val Lys Asn Gly Pro Leu Ser Arg Ala Asp Leu
            290                 295                 300

Asp Thr Asn Asp Thr Phe Ile Val Glu Asn Gly Ser Glu Gly Leu Trp
305                 310                 315                 320

Val Trp Val Gly Lys Lys Ala Thr Gln Lys Glu Arg Gln Ser Ala Ile
                325                 330                 335

Lys Tyr Ala Met Glu Leu Ile Asn Lys Lys Tyr Pro Asn Asn Thr
                340                 345                 350

Pro Val Thr Lys Val Leu Glu Gly Asp Glu Ser Val Glu Phe Lys Ser
                355                 360                 365

Leu Phe Glu Ser Trp Gln Met Ser Glu Gln Lys Ile Thr Ser Ala
                370                 375                 380

Arg Leu Phe Arg Val Ser Arg Asn Gly Ile Phe Lys Gln Val Ala Asn
385                 390                 395                 400

Tyr Glu Pro Asp Asp Leu Glu Asp Asn Ile Met Ile Leu Asp Val
                405                 410                 415

Met Asp Lys Ile Tyr Val Trp Ile Gly Asn Gln Phe Ala Glu Arg Ile
                420                 425                 430

Ala Asp Glu Ala His Val Asp Lys Val Ala Gln Arg Phe Ile Gln Glu
                435                 440                 445

Asp Lys Ser Gly Arg Lys Phe Arg Pro Asn Gln Ile Ile Lys Leu Lys
450                 455                 460

Gln Gly Ser Glu Asp Gly Ala Phe Lys Ser Tyr Phe Pro Lys Trp Asn
465                 470                 475                 480

<210> SEQ ID NO 69
<211> LENGTH: 213
<212> TYPE: PRT
<213> ORGANISM: Artificial Sequence
<220> FEATURE:
<223> OTHER INFORMATION: Der f 7_iso3

<400> SEQUENCE: 69

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
                20                  25                  30

Ile Asp Asp Ala Ile Ala Ala Ile Glu Lys Ser Glu Thr Ile Asp Pro
            35                  40                  45

Met Lys Val Pro Asp His Thr Asp Lys Phe Glu Arg His Val Gly Ile
50                  55                  60

Leu Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
                100                 105                 110

Ser Met Glu Tyr Asp Leu Ala Tyr Lys Leu Gly Asp Leu His Pro Asn
                115                 120                 125

Thr His Val Ile Ser Asp Ile Gln Asp Phe Val Ala Leu Ser Leu
                130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175
```

Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
            195                 200                 205

Glu Leu Glu Lys Asn
    210

<210> SEQ ID NO 70
<211> LENGTH: 356
<212> TYPE: PRT
<213> ORGANISM: Artificial Sequence
<220> FEATURE:
<223> OTHER INFORMATION: Der f 20_iso1

<400> SEQUENCE: 70

Met Val Asp Gln Ala Val Ile Asp Lys Leu Glu Ala Gly Phe Gln Lys
1               5                   10                  15

Leu Gln Ser Ser Ala Glu Cys His Ser Leu Leu Lys Lys Tyr Leu Thr
            20                  25                  30

Arg Asn Val Leu Asp Ala Cys Lys Gly Arg Lys Thr Gly Met Gly Ala
        35                  40                  45

Thr Leu Val Asp Val Val Gln Ser Gly Phe Glu Asn Leu Asp Ser Gly
    50                  55                  60

Val Gly Leu Tyr Ala Pro Asp Ala Glu Ser Tyr Thr Leu Phe Lys Glu
65                  70                  75                  80

Leu Phe Asp Pro Val Ile Glu Asp Tyr His Lys Gly Phe Lys Pro Thr
                85                  90                  95

Asp Lys His Pro Gln Thr Asp Phe Gly Asp Val Asn Thr Leu Cys Asn
            100                 105                 110

Val Asp Pro Asn Asn Glu Phe Val Ile Ser Thr Arg Val Arg Cys Gly
        115                 120                 125

Arg Ser Leu Gln Gly Tyr Pro Phe Asn Pro Cys Leu Thr Glu Ala Gln
    130                 135                 140

Tyr Lys Glu Met Glu Glu Lys Val Lys Gly Gln Leu Asn Ser Phe Glu
145                 150                 155                 160

Gly Glu Leu Lys Gly Thr Tyr Tyr Pro Leu Leu Gly Met Asp Lys Ala
                165                 170                 175

Thr Gln Gln Leu Ile Asp Asp His Phe Leu Phe Lys Glu Gly Asp
            180                 185                 190

Arg Phe Leu Gln Ala Ala Asn Ala Cys Arg Phe Trp Pro Val Gly Cys
    195                 200                 205

Gly Ile Phe His Asn Asp Asn Lys Thr Phe Leu Ile Trp Val Asn Glu
    210                 215                 220

Glu Asp His Leu Arg Ile Ile Ser Met Gln Lys Gly Gly Asp Leu Lys
225                 230                 235                 240

Gln Val Phe Ser Arg Leu Ile Asn Gly Val Asn His Ile Glu Lys Lys
                245                 250                 255

Leu Pro Phe Ser Arg Asp Asp Arg Leu Gly Phe Leu Thr Phe Cys Pro
            260                 265                 270

Thr Asn Leu Gly Thr Thr Ile Arg Ala Ser Val His Ile Lys Leu Pro
        275                 280                 285

Lys Leu Ala Ala Asp Arg Lys Lys Leu Glu Glu Val Ala Gly Lys Tyr
    290                 295                 300

Asn Leu Gln Val Arg Gly Thr Ala Gly Glu His Thr Glu Ser Val Gly
305                 310                 315                 320

```
Gly Val Tyr Asp Ile Ser Asn Lys Arg Arg Met Gly Leu Thr Glu Tyr
            325                 330                 335

Gln Ala Val Lys Glu Met Gln Asp Gly Ile Leu Glu Leu Ile Lys Ile
        340                 345                 350

Glu Lys Ser Met
    355

<210> SEQ ID NO 71
<211> LENGTH: 400
<212> TYPE: PRT
<213> ORGANISM: Artificial Sequence
<220> FEATURE:
<223> OTHER INFORMATION: Der f 1_iso3

<400> SEQUENCE: 71

Met Lys Phe Ala Leu Phe Val Val Ala Ser Leu Ile Ala Thr Val Tyr
1               5                   10                  15

Gly Gln Ser His Gln Tyr Tyr His Thr Ser Gly Leu Arg Asn Leu Gly
            20                  25                  30

Gly Ser Tyr Tyr Arg Ser Ala Gly Ile Ser Gly Val Ala Gly Leu Gly
        35                  40                  45

Gly Leu Ala Tyr Gly Thr Gly Leu Gly Tyr Gly Thr Arg Tyr Gly Tyr
50                  55                  60

Gly Ser Gly Leu Gly Tyr Gly Leu Gly Tyr Gly Leu Gly Tyr Gly Gln
65                  70                  75                  80

Ala Val Ala Leu Ala Pro Ala Gln Ala Val Gly Tyr Val Ala Ala Ala
                85                  90                  95

Pro Ala Val Ala Val Gln Ala Pro Val Ser Tyr Ala Ala Ala Ala
            100                 105                 110

Pro Ala Val Gln Thr Val Ala Val Gln Ala Pro Ala Val Ser Tyr Ala
        115                 120                 125

Ala Ala Pro Ala Val Ala Val Gln Ala His Thr Ala Gln Val Ser Gly
130                 135                 140

Pro Ile His Ala Ala Ile Glu Ser Arg Arg Thr Val Glu Val Ile Asp
145                 150                 155                 160

Gly Pro Ser Thr Gly Asp Ala Pro Val Ala Ser Thr Val Ile Gly
                165                 170                 175

Pro Asn Val Gln Pro Ile Asn Leu Glu Phe Gln Thr Gln Ala Ser Pro
            180                 185                 190

Leu Ala Ala Thr Gln Asn His Val Pro Thr Ala Pro Ala Glu Pro Gln
        195                 200                 205

Gln Ser Ser Tyr Glu Glu Gln Pro Asp Leu Leu Arg Gln Asp Ile Val
210                 215                 220

Lys Pro Val Val Gln Asp Val His Glu Thr Ile Val Pro Phe Arg Arg
225                 230                 235                 240

Ile Thr Gln Glu Leu Lys Pro Val Gln Glu Ser Val His Gln Ile Leu
                245                 250                 255

Pro Arg Gly Gln Glu Arg Gly Phe Tyr Gln Gln Gln Gln Val Arg
            260                 265                 270

Val Ala Gln His Val Ala Ala Pro Ala Ala Val Ala Val Gln Pro Val
        275                 280                 285

Val Gln Ala Ala Pro Ala Ile Ser Ala Val Arg Val Ala Ala Pro
290                 295                 300

Ala Val Ala Tyr Ala Ala Pro Ala Val Ser Thr Val Ser Ala Ala Pro
305                 310                 315                 320
```

```
Ala Ala Ile Gly Val Ile Gly Val Gln Pro Ala Ala Gly Tyr Ile Gly
                325                 330                 335

Tyr Gly Ala Gly Tyr Gly Thr Gly Tyr Gly Thr Gly Tyr Gly Val Ala
            340                 345                 350

Lys Tyr Gly Thr Gly Tyr Gly Leu Thr Ser Gly Leu Ile Gly Gly Gly
            355                 360                 365

Ser Tyr Gly Ser Ser Tyr Ser Val Gln Pro Ala Ser Tyr Gly Thr Gly
            370                 375                 380

Tyr Gly Tyr Thr Thr Tyr Ser Ser Asp Ala Tyr Pro Ile Arg Lys Lys
385             390                 395                 400

<210> SEQ ID NO 72
<211> LENGTH: 556
<212> TYPE: PRT
<213> ORGANISM: Artificial Sequence
<220> FEATURE:
<223> OTHER INFORMATION: Der f 15_iso2

<400> SEQUENCE: 72

Met Lys Thr Ile Tyr Ala Ile Leu Ser Ile Met Ala Cys Ile Gly Leu
1               5                   10                  15

Met Asn Ala Ser Ile Lys Arg Asp His Asn Asp Tyr Ser Lys Asn Pro
            20                  25                  30

Met Arg Ile Val Cys Tyr Val Gly Thr Trp Ser Val Tyr His Lys Val
        35                  40                  45

Asp Pro Tyr Thr Ile Glu Asp Ile Asp Pro Phe Lys Cys Thr His Leu
    50                  55                  60

Met Tyr Gly Phe Ala Lys Ile Asp Glu Tyr Lys Tyr Thr Ile Gln Val
65                  70                  75                  80

Phe Asp Pro Tyr Gln Asp Asn His Asn Ser Trp Glu Lys Arg Gly
                85                  90                  95

Tyr Glu Arg Phe Asn Asn Leu Arg Leu Lys Asn Pro Glu Leu Thr Thr
            100                 105                 110

Met Ile Ser Leu Gly Gly Trp Tyr Glu Gly Ser Glu Lys Tyr Ser Asp
        115                 120                 125

Met Ala Ala Asn Pro Thr Tyr Arg Gln Gln Phe Ile Gln Ser Val Leu
    130                 135                 140

Asp Phe Leu Gln Glu Tyr Lys Phe Asp Gly Leu Asp Leu Asp Trp Glu
145                 150                 155                 160

Tyr Pro Gly Ser Arg Leu Gly Asn Pro Lys Ile Asp Lys Gln Asn Tyr
                165                 170                 175

Leu Ala Leu Val Arg Glu Leu Lys Asp Ala Phe Glu Pro His Gly Tyr
            180                 185                 190

Leu Leu Thr Ala Ala Val Ser Pro Gly Lys Asp Lys Ile Asp Arg Ala
        195                 200                 205

Tyr Asp Ile Lys Glu Leu Asn Lys Leu Phe Asp Trp Met Asn Val Met
    210                 215                 220

Thr Tyr Asp Tyr His Gly Gly Trp Glu Asn Phe Tyr Gly His Asn Ala
225                 230                 235                 240

Pro Leu Tyr Lys Arg Pro Asp Glu Thr Asp Glu Leu His Thr Tyr Phe
                245                 250                 255

Asn Val Asn Tyr Thr Met His Tyr Tyr Leu Asn Asn Gly Ala Thr Arg
            260                 265                 270

Asp Lys Leu Val Met Gly Val Pro Phe Tyr Gly Arg Ala Trp Ser Ile
        275                 280                 285
```

```
Glu Asp Arg Ser Lys Leu Lys Leu Gly Asp Pro Ala Lys Gly Met Ser
    290                 295                 300
Pro Pro Gly Phe Ile Ser Gly Glu Glu Gly Val Leu Ser Tyr Ile Glu
305                 310                 315                 320
Leu Cys Gln Leu Phe Gln Lys Glu Glu Trp His Ile Gln Tyr Asp Glu
                325                 330                 335
Tyr Tyr Asn Ala Pro Tyr Gly Tyr Asn Asp Lys Ile Trp Val Gly Tyr
            340                 345                 350
Asp Asp Leu Ala Ser Ile Ser Cys Lys Leu Ala Phe Leu Lys Glu Leu
        355                 360                 365
Gly Val Ser Gly Val Ile Val Trp Ser Leu Glu Asn Asp Asp Phe Lys
    370                 375                 380
Gly His Cys Gly Pro Lys Asn Pro Leu Leu Asn Lys Val His Asn Met
385                 390                 395                 400
Ile Asn Gly Asp Glu Lys Asn Ser Phe Glu Cys Ile Leu Gly Pro Ser
                405                 410                 415
Thr Thr Thr Pro Thr Pro Thr Thr Thr Pro Thr Thr Thr Pro Thr Pro
            420                 425                 430
Ser Pro Thr Thr Pro Thr Pro Ser Pro Thr Thr Pro Thr Thr Thr Pro
        435                 440                 445
Ser Pro Thr Thr Pro Thr Pro Ser Pro Thr Thr Pro Thr Thr Thr Pro
    450                 455                 460
Ser Pro Thr Thr Pro Thr Pro Thr Thr Pro Thr Pro Thr Pro Thr Thr
465                 470                 475                 480
Ser Thr Pro Ser Pro Thr Thr Thr Glu His Thr Ser Glu Thr Pro Lys
                485                 490                 495
Tyr Thr Thr Tyr Val Asp Gly His Leu Ile Lys Cys Tyr Lys Glu Gly
            500                 505                 510
Asp Ile Pro His Pro Thr Asn Ile His Lys Tyr Leu Val Cys Glu Phe
        515                 520                 525
Val Asn Gly Gly Trp Trp Val His Ile Met Pro Cys Pro Pro Gly Thr
    530                 535                 540
Ile Trp Cys Gln Glu Lys Leu Thr Cys Ile Gly Glu
545                 550                 555
```

<210> SEQ ID NO 73
<211> LENGTH: 356
<212> TYPE: PRT
<213> ORGANISM: Artificial Sequence
<220> FEATURE:
<223> OTHER INFORMATION: Der f 20_iso2

<400> SEQUENCE: 73

```
Met Val Asp Gln Ala Thr Leu Ser Lys Leu Glu Ala Gly Phe Gln Lys
1               5                   10                  15
Leu Gln Asn Ala Gln Asp Cys His Ser Leu Leu Lys Lys Tyr Leu Thr
            20                  25                  30
Arg Asp Val Leu Asp Gln Leu Lys Thr Lys Thr Asp Met Gly Ala
        35                  40                  45
Thr Leu Leu Asp Val Ile Gln Ser Gly Val Glu Asn Leu Asp Ser Gly
    50                  55                  60
Val Gly Ile Tyr Ala Pro Asp Ala Gln Ser Tyr Lys Thr Phe Ala Ala
65                  70                  75                  80
Leu Phe Asp Pro Ile Ile Asp Asp Tyr His Lys Gly Phe Lys Pro Thr
                85                  90                  95
```

```
Asp Lys His Pro Gln Thr Asp Phe Gly Asn Ile Glu His Phe Val Asn
            100                 105                 110

Val Asp Pro Lys Asn Glu Tyr Val Ile Ser Thr Arg Val Arg Cys Gly
        115                 120                 125

Arg Ser Leu Lys Gly Tyr Pro Phe Asn Pro Met Leu Thr Glu Ala Gln
    130                 135                 140

Tyr Lys Glu Met Glu Thr Lys Val Lys Gly Gln Leu Ala Thr Phe Glu
145                 150                 155                 160

Gly Glu Leu Lys Gly Thr Tyr Tyr Pro Leu Leu Gly Met Asp Lys Ala
                165                 170                 175

Thr Gln Gln Lys Leu Ile Asp Asp His Phe Leu Phe Lys Glu Gly Asp
            180                 185                 190

Arg Phe Leu Gln Ala Ala Asn Ala Cys Arg Tyr Trp Pro Val Gly Arg
        195                 200                 205

Gly Ile Phe His Asn Asp Lys Lys Thr Phe Leu Met Trp Val Asn Glu
    210                 215                 220

Glu Asp His Leu Arg Ile Ile Ser Met Gln Lys Gly Gly Asp Leu Lys
225                 230                 235                 240

Glu Val Phe Gly Arg Leu Val Lys Ala Val Lys His Ile Glu Gln Lys
                245                 250                 255

Ile Pro Phe Ser Arg Asp Asp Arg Leu Gly Tyr Leu Thr Phe Cys Pro
            260                 265                 270

Thr Asn Leu Gly Thr Thr Ile Arg Ala Ser Val His Ile Lys Leu Pro
        275                 280                 285

Lys Leu Ala Ala Asp Arg Lys Lys Leu Glu Glu Val Ala Ala Arg Tyr
    290                 295                 300

Asn Leu Gln Val Arg Gly Thr Ala Gly Glu His Thr Glu Ser Val Gly
305                 310                 315                 320

Gly Ile Tyr Asp Ile Ser Asn Lys Arg Arg Met Gly Leu Thr Glu Tyr
                325                 330                 335

Gln Ala Val Lys Glu Met Gln Asp Gly Ile Ile Glu Leu Ile Lys Met
            340                 345                 350

Glu Lys Ser Leu
        355

<210> SEQ ID NO 74
<211> LENGTH: 77
<212> TYPE: PRT
<213> ORGANISM: Artificial Sequence
<220> FEATURE:
<223> OTHER INFORMATION: Der f 1_iso1_TI

<400> SEQUENCE: 74

Phe Trp Pro Thr Val Thr Arg Leu Trp Ile Phe Leu Asn Arg Asn Ser
1               5                   10                  15

Ser Ile Ala His Leu Asn Thr Asp Val Thr Ala Ile Gln Tyr Gln Glu
            20                  25                  30

Ala Ser Asn Thr Ser Asn Lys Met Val Ser Leu Lys Lys Glu Ala Ile
        35                  40                  45

His Thr Leu His Glu Asn Asn Ala Asp Asp Gln Ile Arg Asn Ile
    50                  55                  60

Thr Val Ser Gln Thr Thr Ala Lys Phe Ile His Gln Met
65                  70                  75

<210> SEQ ID NO 75
<211> LENGTH: 61
```

```
<212> TYPE: PRT
<213> ORGANISM: Artificial Sequence
<220> FEATURE:
<223> OTHER INFORMATION: Der f 1_iso1_TI

<400> SEQUENCE: 75

Ser Asn Ile Met Met Asp Glu Gln Ser Phe Asn Met Thr Met Val Ile
1               5                   10                  15

Asn Gln Thr Ile Met Pro Ser Thr Leu Ser Val Thr Glu Val His Lys
            20                  25                  30

Ala Ser Ile Ile Gly Ser Tyr Glu Thr Val Gly Ile Gln Pro Gly Val
        35                  40                  45

Ile Ala Asp Thr Asp Ile Ser Lys Pro Glu Thr Thr Ser
    50                  55                  60

<210> SEQ ID NO 76
<211> LENGTH: 48
<212> TYPE: PRT
<213> ORGANISM: Artificial Sequence
<220> FEATURE:
<223> OTHER INFORMATION: Der f 1_iso1_TI

<400> SEQUENCE: 76

Met Val Ile Asn Gln Thr Ile Met Pro Ser Thr Leu Ser Val Thr Glu
1               5                   10                  15

Val His Lys Ala Ser Ile Ile Gly Ser Tyr Glu Thr Val Gly Ile Gln
            20                  25                  30

Pro Gly Val Ile Ala Asp Thr Asp Ile Ser Lys Pro Glu Thr Thr Ser
        35                  40                  45

<210> SEQ ID NO 77
<211> LENGTH: 26
<212> TYPE: PRT
<213> ORGANISM: Artificial Sequence
<220> FEATURE:
<223> OTHER INFORMATION: Der f 1_iso1_TI

<400> SEQUENCE: 77

Ile Gly Ser Tyr Glu Thr Val Gly Ile Gln Pro Gly Val Ile Ala Asp
1               5                   10                  15

Thr Asp Ile Ser Lys Pro Glu Thr Thr Ser
            20                  25

<210> SEQ ID NO 78
<211> LENGTH: 77
<212> TYPE: PRT
<213> ORGANISM: Artificial Sequence
<220> FEATURE:
<223> OTHER INFORMATION: Der f 1_iso2_TI

<400> SEQUENCE: 78

Phe Trp Pro Thr Val Thr Arg Leu Trp Ile Phe Leu Asn Arg Asn Ser
1               5                   10                  15

Ser Ile Ala His Leu Asn Thr Asp Val Thr Ala Ile Gln Tyr Gln Glu
            20                  25                  30

Ala Ser Asn Thr Ser Asn Lys Met Val Ser Leu Lys Lys Glu Ala Ile
        35                  40                  45

His Thr Leu His Glu Asn Asn Asn Ala Asp Asp Gln Ile Arg Asn Ile
    50                  55                  60

Thr Val Ser Gln Thr Thr Ala Lys Phe Ile His Gln Met
65                  70                  75
```

<210> SEQ ID NO 79
<211> LENGTH: 61
<212> TYPE: PRT
<213> ORGANISM: Artificial Sequence
<220> FEATURE:
<223> OTHER INFORMATION: Der f 1_iso2_TI

<400> SEQUENCE: 79

Ser Asn Ile Met Met Asp Glu Gln Ser Phe Asn Met Thr Met Val Ile
1               5                   10                  15

Asn Gln Thr Ile Met Pro Ser Thr Leu Ser Val Thr Glu Val His Lys
            20                  25                  30

Ala Ser Ile Ile Gly Ser Tyr Glu Thr Val Gly Ile Gln Pro Gly Val
        35                  40                  45

Ile Ala Asp Thr Asp Ile Ser Lys Pro Glu Thr Thr Ser
    50                  55                  60

<210> SEQ ID NO 80
<211> LENGTH: 48
<212> TYPE: PRT
<213> ORGANISM: Artificial Sequence
<220> FEATURE:
<223> OTHER INFORMATION: Der f 1_iso2_TI

<400> SEQUENCE: 80

Met Val Ile Asn Gln Thr Ile Met Pro Ser Thr Leu Ser Val Thr Glu
1               5                   10                  15

Val His Lys Ala Ser Ile Ile Gly Ser Tyr Glu Thr Val Gly Ile Gln
            20                  25                  30

Pro Gly Val Ile Ala Asp Thr Asp Ile Ser Lys Pro Glu Thr Thr Ser
        35                  40                  45

<210> SEQ ID NO 81
<211> LENGTH: 26
<212> TYPE: PRT
<213> ORGANISM: Artificial Sequence
<220> FEATURE:
<223> OTHER INFORMATION: Der f 1_iso2_TI

<400> SEQUENCE: 81

Ile Gly Ser Tyr Glu Thr Val Gly Ile Gln Pro Gly Val Ile Ala Asp
1               5                   10                  15

Thr Asp Ile Ser Lys Pro Glu Thr Thr Ser
            20                  25

<210> SEQ ID NO 82
<211> LENGTH: 23
<212> TYPE: PRT
<213> ORGANISM: Artificial Sequence
<220> FEATURE:
<223> OTHER INFORMATION: Der f 23_iso1_TI

<400> SEQUENCE: 82

Ile Phe Val Gln Ile Gly Lys Leu Tyr Ile Lys Val Val Gln Val Ile
1               5                   10                  15

Gln Asp Gly Met Lys Lys Asn
            20

<210> SEQ ID NO 83
<211> LENGTH: 25
<212> TYPE: PRT
<213> ORGANISM: Artificial Sequence
<220> FEATURE:

<223> OTHER INFORMATION: Der f 11_iso1_TI

<400> SEQUENCE: 83

Tyr Val Ile Asn Val Ile Asn Trp His Val Lys Thr Arg Asn Leu Gln
1               5                   10                  15
Thr Ile Leu Pro Lys Leu Asn His Asn
            20                  25

<210> SEQ ID NO 84
<211> LENGTH: 28
<212> TYPE: PRT
<213> ORGANISM: Artificial Sequence
<220> FEATURE:
<223> OTHER INFORMATION: Der f 11_iso1_TI

<400> SEQUENCE: 84

Thr Met Lys Tyr Ile Lys Asn Leu Glu Phe Leu Met Asn Glu Tyr Arg
1               5                   10                  15
Asn Leu Gln Leu Asn Ser Asn Leu Leu Lys Ile Cys
            20                  25

<210> SEQ ID NO 85
<211> LENGTH: 37
<212> TYPE: PRT
<213> ORGANISM: Artificial Sequence
<220> FEATURE:
<223> OTHER INFORMATION: Der f 15_iso1_TI

<400> SEQUENCE: 85

Trp Ile Gly Ser Ile Leu Asp Leu Asp Trp Val Thr Arg Lys Ser Thr
1               5                   10                  15
Asn Lys Thr Ile Trp Leu Trp Leu Glu Asn Leu Lys Thr Leu Leu Asn
            20                  25                  30
Leu Met Ala Thr Cys
                35

<210> SEQ ID NO 86
<211> LENGTH: 15
<212> TYPE: PRT
<213> ORGANISM: Artificial Sequence
<220> FEATURE:
<223> OTHER INFORMATION: Der f 32_iso1_TI

<400> SEQUENCE: 86

Leu Leu Lys Lys Ser Leu Lys Lys His Ile Asn Ile Gly Lys Lys
1               5                   10                  15

<210> SEQ ID NO 87
<211> LENGTH: 44
<212> TYPE: PRT
<213> ORGANISM: Artificial Sequence
<220> FEATURE:
<223> OTHER INFORMATION: Der f 25_iso1_TI

<400> SEQUENCE: 87

Gly Pro Leu Val Leu Val Lys Gln Pro Val His Asn Lys His Lys Lys
1               5                   10                  15
Phe Ile Lys Asn Phe Asp Asn Gly Phe Leu Lys Met Phe His His Lys
            20                  25                  30
Leu Pro Lys Gln Phe Glu Ser Phe Met Val Val Gln
        35                  40

<210> SEQ ID NO 88

```
<211> LENGTH: 17
<212> TYPE: PRT
<213> ORGANISM: Artificial Sequence
<220> FEATURE:
<223> OTHER INFORMATION: Der f 25_iso1_TI

<400> SEQUENCE: 88

Met Phe His His Lys Leu Pro Lys Gln Phe Glu Ser Phe Met Val Val
1               5                   10                  15

Gln

<210> SEQ ID NO 89
<211> LENGTH: 15
<212> TYPE: PRT
<213> ORGANISM: Artificial Sequence
<220> FEATURE:
<223> OTHER INFORMATION: Der f 16_iso1_TI

<400> SEQUENCE: 89

Tyr Lys Arg Ile Lys Val Ala Val Asn Phe Asp Gln Ile Arg Leu
1               5                   10                  15

<210> SEQ ID NO 90
<211> LENGTH: 27
<212> TYPE: PRT
<213> ORGANISM: Artificial Sequence
<220> FEATURE:
<223> OTHER INFORMATION: Der f 26_iso1_TI

<400> SEQUENCE: 90

Glu Ile Ser Val His Phe Ala Leu Val Lys Lys Asp Leu Val Leu Asn
1               5                   10                  15

His Pro His Phe Ile Val Ser Tyr Pro Ile Leu
            20                  25

<210> SEQ ID NO 91
<211> LENGTH: 16
<212> TYPE: PRT
<213> ORGANISM: Artificial Sequence
<220> FEATURE:
<223> OTHER INFORMATION: Der f 26_iso1_TI

<400> SEQUENCE: 91

Lys Arg Trp Lys Ala Met Ala His Asn Arg Val Asn His Pro Arg Lys
1               5                   10                  15

<210> SEQ ID NO 92
<211> LENGTH: 23
<212> TYPE: PRT
<213> ORGANISM: Artificial Sequence
<220> FEATURE:
<223> OTHER INFORMATION: Der f 23_iso2_TI

<400> SEQUENCE: 92

Ile Phe Val Gln Ile Gly Lys Leu Tyr Ile Lys Val Val Gln Val Ile
1               5                   10                  15

Gln Asp Gly Met Lys Lys Asn
            20

<210> SEQ ID NO 93
<211> LENGTH: 15
<212> TYPE: PRT
<213> ORGANISM: Artificial Sequence
<220> FEATURE:
<223> OTHER INFORMATION: Der f 13_iso1_TI
```

```
<400> SEQUENCE: 93

Lys Val Thr Ile Asn Leu Phe Lys His Asn Ser Val Ile Lys Lys
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Der f 7_iso1_TI

<400> SEQUENCE: 94

Leu Pro Ile Asn Ser Asn Val Met Leu Val Phe Trp Ile Ser Lys Val
1               5                   10                  15

Asn

<210> SEQ ID NO 95
<211> LENGTH: 46
<212> TYPE: PRT
<213> ORGANISM: Artificial Sequence
<220> FEATURE:
<223> OTHER INFORMATION: Der f 27_iso1_TI

<400> SEQUENCE: 95

Met Ile Leu Thr Lys Phe Val Asn Gln Ser Ile Gln Leu Leu Leu Met
1               5                   10                  15

Lys Leu Leu Asp Lys Leu Leu Val Val Ser His Gln Leu Phe Ile Ser
            20                  25                  30

Arg Lys Leu Asn Ser Val His His Ile Asn Cys Arg Lys Phe
        35                  40                  45

<210> SEQ ID NO 96
<211> LENGTH: 17
<212> TYPE: PRT
<213> ORGANISM: Artificial Sequence
<220> FEATURE:
<223> OTHER INFORMATION: Der f 7_iso2_TI

<400> SEQUENCE: 96

Leu Pro Ile Asn Ser Asn Val Met Leu Val Phe Trp Ile Ser Lys Val
1               5                   10                  15

Asn

<210> SEQ ID NO 97
<211> LENGTH: 16
<212> TYPE: PRT
<213> ORGANISM: Artificial Sequence
<220> FEATURE:
<223> OTHER INFORMATION: Der f 29_iso1_TI

<400> SEQUENCE: 97

Lys Arg Trp Lys Ala Met Ala His Asn Arg Val Asn His Pro Arg Lys
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Der f 18_iso1_TI

<400> SEQUENCE: 98

Lys Pro Cys Ile Ile Val Pro Ile Thr Tyr Arg His Leu Thr Lys
1               5                   10                  15
```

```
<210> SEQ ID NO 99
<211> LENGTH: 15
<212> TYPE: PRT
<213> ORGANISM: Artificial Sequence
<220> FEATURE:
<223> OTHER INFORMATION: Der f 16_iso2_TI

<400> SEQUENCE: 99

Tyr Lys Arg Ile Lys Val Ala Val Asn Phe Asp Gln Ile Arg Leu
1               5                   10                  15

<210> SEQ ID NO 100
<211> LENGTH: 17
<212> TYPE: PRT
<213> ORGANISM: Artificial Sequence
<220> FEATURE:
<223> OTHER INFORMATION: Der f 7_iso3_TI

<400> SEQUENCE: 100

Leu Pro Ile Asn Ser Asn Val Met Leu Val Phe Trp Ile Ser Lys Val
1               5                   10                  15

Asn

<210> SEQ ID NO 101
<211> LENGTH: 30
<212> TYPE: PRT
<213> ORGANISM: Artificial Sequence
<220> FEATURE:
<223> OTHER INFORMATION: Der f 20_iso1_TI

<400> SEQUENCE: 101

Cys Val Met Trp Ile Gln Ile Met Asn Leu Ser Phe Gln His Val Tyr
1               5                   10                  15

Val Val Ala Asp His Cys Lys Val Ile His Leu Ile His Ala
            20                  25                  30

<210> SEQ ID NO 102
<211> LENGTH: 52
<212> TYPE: PRT
<213> ORGANISM: Artificial Sequence
<220> FEATURE:
<223> OTHER INFORMATION: Der f 20_iso1_TI

<400> SEQUENCE: 102

Trp Lys Lys Leu Leu Ala Asn Ile Ile Tyr Lys Tyr Val Val Leu Pro
1               5                   10                  15

Val Asn Thr Pro Lys Val Leu Ala Val Phe Thr Ile Ser Val Ile Asn
            20                  25                  30

Val Val Trp Val Leu Leu Asn Ile Arg Pro Ser Lys Arg Cys Lys Met
        35                  40                  45

Val Phe Leu Asn
    50

<210> SEQ ID NO 103
<211> LENGTH: 36
<212> TYPE: PRT
<213> ORGANISM: Artificial Sequence
<220> FEATURE:
<223> OTHER INFORMATION: Der f 20_iso1_TI

<400> SEQUENCE: 103

Val Asn Thr Pro Lys Val Leu Ala Val Phe Thr Ile Ser Val Ile Asn
1               5                   10                  15
```

```
Val Val Trp Val Leu Leu Asn Ile Arg Pro Ser Lys Arg Cys Lys Met
            20                  25                  30

Val Phe Leu Asn
            35

<210> SEQ ID NO 104
<211> LENGTH: 26
<212> TYPE: PRT
<213> ORGANISM: Artificial Sequence
<220> FEATURE:
<223> OTHER INFORMATION: Der f 20_iso1_TI

<400> SEQUENCE: 104

Thr Ile Ser Val Ile Asn Val Val Trp Val Leu Leu Asn Ile Arg Pro
1               5                   10                  15

Ser Lys Arg Cys Lys Met Val Phe Leu Asn
            20                  25

<210> SEQ ID NO 105
<211> LENGTH: 18
<212> TYPE: PRT
<213> ORGANISM: Artificial Sequence
<220> FEATURE:
<223> OTHER INFORMATION: Der f 1_iso3_TI

<400> SEQUENCE: 105

Glu Gln Val Met Val Leu Leu Asn Thr Glu Pro Asp Met Val Ser Leu
1               5                   10                  15

Ala Val

<210> SEQ ID NO 106
<211> LENGTH: 42
<212> TYPE: PRT
<213> ORGANISM: Artificial Sequence
<220> FEATURE:
<223> OTHER INFORMATION: Der f 1_iso3_TI

<400> SEQUENCE: 106

Val Ala His Met Asp His His Ile Gln Tyr Asn Gln Pro Ala Thr Glu
1               5                   10                  15

Leu Val Met Val Thr Leu Pro Ile Ala Val Met Pro Thr Gln Ser Glu
            20                  25                  30

Lys Asn Lys Leu Val Leu Pro Phe Ser Phe
            35                  40

<210> SEQ ID NO 107
<211> LENGTH: 37
<212> TYPE: PRT
<213> ORGANISM: Artificial Sequence
<220> FEATURE:
<223> OTHER INFORMATION: Der f 15_iso2_TI

<400> SEQUENCE: 107

Trp Ile Gly Ser Ile Leu Asp Leu Asp Trp Val Thr Arg Lys Ser Thr
1               5                   10                  15

Asn Lys Thr Ile Trp Leu Trp Leu Glu Asn Leu Lys Thr Leu Leu Asn
            20                  25                  30

Leu Met Ala Thr Cys
            35

<210> SEQ ID NO 108
<211> LENGTH: 29
```

```
<212> TYPE: PRT
<213> ORGANISM: Artificial Sequence
<220> FEATURE:
<223> OTHER INFORMATION: Der f 20_iso2_TI

<400> SEQUENCE: 108

Val Val Ser Met Ile Leu Val Thr Asn Asp Glu Trp Val Ser Pro Asn
1               5                   10                  15

Thr Lys Leu Leu Arg Lys Cys Lys Met Ala Ser Leu Asn
            20                  25

<210> SEQ ID NO 109
<211> LENGTH: 22
<212> TYPE: PRT
<213> ORGANISM: Artificial Sequence
<220> FEATURE:
<223> OTHER INFORMATION: Der f 20_iso2_TI

<400> SEQUENCE: 109

Thr Asn Asp Glu Trp Val Ser Pro Asn Thr Lys Leu Leu Arg Lys Cys
1               5                   10                  15

Lys Met Ala Ser Leu Asn
            20

<210> SEQ ID NO 110
<211> LENGTH: 56
<212> TYPE: PRT
<213> ORGANISM: Artificial Sequence
<220> FEATURE:
<223> OTHER INFORMATION: Arah2-ref1-g11-id30

<400> SEQUENCE: 110

Arg Lys Ser Asn Val Thr Arg Ile His Met Asp Gly Thr Arg Thr Ala
1               5                   10                  15

Leu Val Arg Ile Arg Thr Ala Leu Val Arg Thr Arg Thr Asp Val Ile
            20                  25                  30

Arg Thr Ala Leu Val His Met Ile Gly Glu Ala Leu Asp Leu Leu Ser
        35                  40                  45

Thr Lys Arg Gly Val Ala Met Ser
    50                  55

<210> SEQ ID NO 111
<211> LENGTH: 40
<212> TYPE: PRT
<213> ORGANISM: Artificial Sequence
<220> FEATURE:
<223> OTHER INFORMATION: Arah2-ref1-g11-id31

<400> SEQUENCE: 111

Leu Val Arg Ile Arg Thr Ala Leu Val Arg Thr Arg Thr Asp Val Ile
1               5                   10                  15

Arg Thr Ala Leu Val His Met Ile Gly Glu Ala Leu Asp Leu Leu Ser
            20                  25                  30

Thr Lys Arg Gly Val Ala Met Ser
            35                  40

<210> SEQ ID NO 112
<211> LENGTH: 38
<212> TYPE: PRT
<213> ORGANISM: Artificial Sequence
<220> FEATURE:
<223> OTHER INFORMATION: Arah2-ref1-g11-id32

<400> SEQUENCE: 112
```

```
Arg Ile Arg Thr Ala Leu Val Arg Thr Arg Thr Asp Val Ile Arg Thr
1               5                   10                  15

Ala Leu Val His Met Ile Gly Glu Ala Leu Asp Leu Ser Thr Lys
            20                  25                  30

Arg Gly Val Ala Met Ser
            35

<210> SEQ ID NO 113
<211> LENGTH: 21
<212> TYPE: PRT
<213> ORGANISM: Artificial Sequence
<220> FEATURE:
<223> OTHER INFORMATION: Arah2-ref1-g11-id33

<400> SEQUENCE: 113

Leu Val His Met Ile Gly Glu Ala Leu Asp Leu Leu Ser Thr Lys Arg
1               5                   10                  15

Gly Val Ala Met Ser
            20

<210> SEQ ID NO 114
<211> LENGTH: 10
<212> TYPE: PRT
<213> ORGANISM: Artificial Sequence
<220> FEATURE:
<223> OTHER INFORMATION: Arah2-ref1-g11-id34

<400> SEQUENCE: 114

Leu Ser Thr Lys Arg Gly Val Ala Met Ser
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Arah2-ref1-g12-id35

<400> SEQUENCE: 115

Lys Gly Ala Cys Ala Arg His Cys Asn Arg
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Arah2-ref1-g12-id36

<400> SEQUENCE: 116

Gly Ala Cys Ala Arg His Cys Asn Arg
1               5

<210> SEQ ID NO 117
<211> LENGTH: 76
<212> TYPE: PRT
<213> ORGANISM: Artificial Sequence
<220> FEATURE:
<223> OTHER INFORMATION: Arah2-ref2-g13-id37

<400> SEQUENCE: 117

Lys Gly Ala Cys Ala Arg His Cys Asn Arg Ser Trp Arg Thr Arg Ala
1               5                   10                  15

Ile Gly Cys Arg Gly Gly Asn Arg Ser Asn Ser Ser Arg Gly Ser Ser
```

```
              20                  25                  30

Gly Thr Cys Leu Asn Ser Ala Ala Leu Gly His His Ser Val Ala Thr
            35                  40                  45

Trp Thr Ser Lys Val Ala Ala Glu Thr Asp Thr Lys His Leu Ser Gln
        50                  55                  60

Lys Lys Lys Arg Lys Glu Lys Lys Ile Ala Tyr Ile
65                  70                  75

<210> SEQ ID NO 118
<211> LENGTH: 75
<212> TYPE: PRT
<213> ORGANISM: Artificial Sequence
<220> FEATURE:
<223> OTHER INFORMATION: Arah2-ref2-g13-id38

<400> SEQUENCE: 118

Gly Ala Cys Ala Arg His Cys Asn Arg Ser Trp Arg Thr Arg Ala Ile
1               5                   10                  15

Gly Cys Arg Gly Gly Asn Arg Ser Asn Ser Ser Arg Gly Ser Ser Gly
            20                  25                  30

Thr Cys Leu Asn Ser Ala Ala Leu Gly His His Ser Val Ala Thr Trp
        35                  40                  45

Thr Ser Lys Val Ala Ala Glu Thr Asp Thr Lys His Leu Ser Gln Lys
    50                  55                  60

Lys Lys Arg Lys Glu Lys Lys Ile Ala Tyr Ile
65                  70                  75

<210> SEQ ID NO 119
<211> LENGTH: 49
<212> TYPE: PRT
<213> ORGANISM: Artificial Sequence
<220> FEATURE:
<223> OTHER INFORMATION: Arah2-ref2-g13-id39

<400> SEQUENCE: 119

Ser Arg Gly Ser Ser Gly Thr Cys Leu Asn Ser Ala Ala Leu Gly His
1               5                   10                  15

His Ser Val Ala Thr Trp Thr Ser Lys Val Ala Ala Glu Thr Asp Thr
            20                  25                  30

Lys His Leu Ser Gln Lys Lys Lys Arg Lys Glu Lys Lys Ile Ala Tyr
        35                  40                  45

Ile

<210> SEQ ID NO 120
<211> LENGTH: 33
<212> TYPE: PRT
<213> ORGANISM: Artificial Sequence
<220> FEATURE:
<223> OTHER INFORMATION: Arah2-ref2-g13-id40

<400> SEQUENCE: 120

His Ser Val Ala Thr Trp Thr Ser Lys Val Ala Ala Glu Thr Asp Thr
1               5                   10                  15

Lys His Leu Ser Gln Lys Lys Lys Arg Lys Glu Lys Lys Ile Ala Tyr
            20                  25                  30

Ile

<210> SEQ ID NO 121
<211> LENGTH: 87
<212> TYPE: PRT
```

<213> ORGANISM: Artificial Sequence
<220> FEATURE:
<223> OTHER INFORMATION: Arah2-ref1-g11-id30

<400> SEQUENCE: 121

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Arg
            20                  25                  30

Lys Ser Asn Val Thr Arg Ile His Met Asp Gly Thr Thr Ala Leu
        35                  40                  45

Val Arg Ile Arg Thr Ala Leu Val Arg Thr Thr Asp Val Ile Arg
    50                  55                  60

Thr Ala Leu Val His Met Ile Gly Glu Ala Leu Asp Leu Leu Ser Thr
65                  70                  75                  80

Lys Arg Gly Val Ala Met Ser
                85

<210> SEQ ID NO 122
<211> LENGTH: 87
<212> TYPE: PRT
<213> ORGANISM: Artificial Sequence
<220> FEATURE:
<223> OTHER INFORMATION: Arah2-ref1-g11-id31

<400> SEQUENCE: 122

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Gly Arg Asp Pro Tyr Ser Leu
        35                  40                  45

Val Arg Ile Arg Thr Ala Leu Val Arg Thr Thr Asp Val Ile Arg
    50                  55                  60

Thr Ala Leu Val His Met Ile Gly Glu Ala Leu Asp Leu Leu Ser Thr
65                  70                  75                  80

Lys Arg Gly Val Ala Met Ser
                85

<210> SEQ ID NO 123
<211> LENGTH: 87
<212> TYPE: PRT
<213> ORGANISM: Artificial Sequence
<220> FEATURE:
<223> OTHER INFORMATION: Arah2-ref1-g11-id32

<400> SEQUENCE: 123

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Gly Arg Asp Pro Tyr Ser Pro
        35                  40                  45

Ser Arg Ile Arg Thr Ala Leu Val Arg Thr Thr Asp Val Ile Arg
    50                  55                  60

Thr Ala Leu Val His Met Ile Gly Glu Ala Leu Asp Leu Leu Ser Thr
65                  70                  75                  80

Lys Arg Gly Val Ala Met Ser
                85

<210> SEQ ID NO 124
<211> LENGTH: 87
<212> TYPE: PRT
<213> ORGANISM: Artificial Sequence
<220> FEATURE:
<223> OTHER INFORMATION: Arah2-ref1-g11-id33

<400> SEQUENCE: 124

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Gly Arg Asp Pro Tyr Ser Pro
        35                  40                  45

Ser Gln Asp Pro Tyr Ser Pro Ser Gln Asp Pro Asp Arg Arg Asp Pro
    50                  55                  60

Tyr Ser Leu Val His Met Ile Gly Glu Ala Leu Asp Leu Leu Ser Thr
65                  70                  75                  80

Lys Arg Gly Val Ala Met Ser
                85

<210> SEQ ID NO 125
<211> LENGTH: 87
<212> TYPE: PRT
<213> ORGANISM: Artificial Sequence
<220> FEATURE:
<223> OTHER INFORMATION: Arah2-ref1-g11-id34

<400> SEQUENCE: 125

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Gly Arg Asp Pro Tyr Ser Pro
        35                  40                  45

Ser Gln Asp Pro Tyr Ser Pro Ser Gln Asp Pro Asp Arg Arg Asp Pro
    50                  55                  60

Tyr Ser Pro Ser Pro Tyr Asp Arg Arg Gly Ala Gly Ser Leu Ser Thr
65                  70                  75                  80

Lys Arg Gly Val Ala Met Ser
                85

<210> SEQ ID NO 126
<211> LENGTH: 104
<212> TYPE: PRT
<213> ORGANISM: Artificial Sequence
<220> FEATURE:
<223> OTHER INFORMATION: Arah2-ref1-g12-id35

<400> SEQUENCE: 126

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Gly Arg Asp Pro Tyr Ser Pro
        35                  40                  45

Ser Gln Asp Pro Tyr Ser Pro Ser Gln Asp Pro Asp Arg Arg Asp Pro
    50                  55                  60

```
Tyr Ser Pro Ser Pro Tyr Asp Arg Arg Gly Ala Gly Ser Ser Gln His
 65                  70                  75                  80

Gln Glu Arg Cys Cys Asn Glu Leu Asn Glu Phe Glu Asn Asn Lys Gly
                 85                  90                  95

Ala Cys Ala Arg His Cys Asn Arg
            100

<210> SEQ ID NO 127
<211> LENGTH: 104
<212> TYPE: PRT
<213> ORGANISM: Artificial Sequence
<220> FEATURE:
<223> OTHER INFORMATION: Arah2-ref1-g12-id36

<400> SEQUENCE: 127

Met Ala Arg Gln Gln Trp Glu Leu Gln Gly Asp Arg Arg Cys Gln Ser
  1               5                  10                  15

Gln Leu Glu Arg Ala Asn Leu Arg Pro Cys Glu Gln His Leu Met Gln
                 20                  25                  30

Lys Ile Gln Arg Asp Glu Asp Ser Tyr Gly Arg Asp Pro Tyr Ser Pro
             35                  40                  45

Ser Gln Asp Pro Tyr Ser Pro Ser Gln Asp Pro Asp Arg Arg Asp Pro
         50                  55                  60

Tyr Ser Pro Ser Pro Tyr Asp Arg Arg Gly Ala Gly Ser Ser Gln His
 65                  70                  75                  80

Gln Glu Arg Cys Cys Asn Glu Leu Asn Glu Phe Glu Asn Asn Gln Gly
                 85                  90                  95

Ala Cys Ala Arg His Cys Asn Arg
            100

<210> SEQ ID NO 128
<211> LENGTH: 158
<212> TYPE: PRT
<213> ORGANISM: Artificial Sequence
<220> FEATURE:
<223> OTHER INFORMATION: Arah2-ref2-g13-id37

<400> SEQUENCE: 128

Met Ala Arg Gln Gln Trp Glu Leu Gln Gly Asp Arg Arg Cys Gln Ser
  1               5                  10                  15

Gln Leu Glu Arg Ala Asn Leu Arg Pro Cys Glu Gln His Leu Met Gln
                 20                  25                  30

Lys Ile Gln Arg Asp Glu Asp Ser Tyr Glu Arg Asp Pro Tyr Ser Pro
             35                  40                  45

Ser Gln Asp Pro Tyr Ser Pro Ser Pro Tyr Asp Arg Arg Gly Ala Gly
         50                  55                  60

Ser Ser Gln His Gln Glu Arg Cys Cys Asn Glu Leu Asn Glu Phe Glu
 65                  70                  75                  80

Asn Asn Lys Gly Ala Cys Ala Arg His Cys Asn Arg Ser Trp Arg Thr
                 85                  90                  95

Arg Ala Ile Gly Cys Arg Gly Gly Asn Arg Ser Asn Ser Ser Arg Gly
            100                 105                 110

Ser Ser Gly Thr Cys Leu Asn Ser Ala Ala Leu Gly His His Ser Val
            115                 120                 125

Ala Thr Trp Thr Ser Lys Val Ala Ala Glu Asp Thr Lys His Leu
        130                 135                 140

Ser Gln Lys Lys Lys Arg Lys Glu Lys Lys Ile Ala Tyr Ile
145                 150                 155
```

<210> SEQ ID NO 129
<211> LENGTH: 158
<212> TYPE: PRT
<213> ORGANISM: Artificial Sequence
<220> FEATURE:
<223> OTHER INFORMATION: Arah2-ref2-g13-id38

<400> SEQUENCE: 129

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Glu Arg Asp Pro Tyr Ser Pro
        35                  40                  45

Ser Gln Asp Pro Tyr Ser Pro Ser Pro Tyr Asp Arg Arg Gly Ala Gly
    50                  55                  60

Ser Ser Gln His Gln Glu Arg Cys Cys Asn Glu Leu Asn Glu Phe Glu
65                  70                  75                  80

Asn Asn Gln Gly Ala Cys Ala Arg His Cys Asn Arg Ser Trp Arg Thr
                85                  90                  95

Arg Ala Ile Gly Cys Arg Gly Gly Asn Arg Ser Asn Ser Ser Arg Gly
            100                 105                 110

Ser Ser Gly Thr Cys Leu Asn Ser Ala Ala Leu Gly His His Ser Val
        115                 120                 125

Ala Thr Trp Thr Ser Lys Val Ala Ala Glu Thr Asp Thr Lys His Leu
    130                 135                 140

Ser Gln Lys Lys Lys Arg Lys Glu Lys Lys Ile Ala Tyr Ile
145                 150                 155

<210> SEQ ID NO 130
<211> LENGTH: 158
<212> TYPE: PRT
<213> ORGANISM: Artificial Sequence
<220> FEATURE:
<223> OTHER INFORMATION: Arah2-ref2-g13-id39

<400> SEQUENCE: 130

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Glu Arg Asp Pro Tyr Ser Pro
        35                  40                  45

Ser Gln Asp Pro Tyr Ser Pro Ser Pro Tyr Asp Arg Arg Gly Ala Gly
    50                  55                  60

Ser Ser Gln His Gln Glu Arg Cys Cys Asn Glu Leu Asn Glu Phe Glu
65                  70                  75                  80

Asn Asn Gln Arg Cys Met Cys Glu Ala Leu Gln Gln Ile Met Glu Asn
                85                  90                  95

Gln Ser Asp Arg Leu Gln Gly Arg Gln Glu Gln Gln Ser Arg Gly
            100                 105                 110

Ser Ser Gly Thr Cys Leu Asn Ser Ala Ala Leu Gly His His Ser Val
        115                 120                 125

Ala Thr Trp Thr Ser Lys Val Ala Ala Glu Thr Asp Thr Lys His Leu
    130                 135                 140

Ser Gln Lys Lys Lys Arg Lys Glu Lys Lys Ile Ala Tyr Ile

<210> SEQ ID NO 131
<211> LENGTH: 158
<212> TYPE: PRT
<213> ORGANISM: Artificial Sequence
<220> FEATURE:
<223> OTHER INFORMATION: Arah2-ref2-g13-id40

<400> SEQUENCE: 131

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Glu Arg Asp Pro Tyr Ser Pro
        35                  40                  45

Ser Gln Asp Pro Tyr Ser Pro Ser Pro Tyr Asp Arg Arg Gly Ala Gly
    50                  55                  60

Ser Ser Gln His Gln Glu Arg Cys Cys Asn Glu Leu Asn Glu Phe Glu
65                  70                  75                  80

Asn Asn Gln Arg Cys Met Cys Glu Ala Leu Gln Gln Ile Met Glu Asn
                85                  90                  95

Gln Ser Asp Arg Leu Gln Gly Arg Gln Gln Glu Gln Gln Phe Lys Arg
            100                 105                 110

Glu Leu Arg Asn Leu Pro Gln Cys Gly Leu Arg Ala His Ser Val
        115                 120                 125

Ala Thr Trp Thr Ser Lys Val Ala Ala Glu Thr Asp Thr Lys His Leu
    130                 135                 140

Ser Gln Lys Lys Lys Arg Lys Glu Lys Lys Ile Ala Tyr Ile
145                 150                 155

<210> SEQ ID NO 132
<211> LENGTH: 153
<212> TYPE: PRT
<213> ORGANISM: Artificial Sequence
<220> FEATURE:
<223> OTHER INFORMATION: Arah2-ref1

<400> SEQUENCE: 132

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
            20                  25                  30

Lys Ile Gln Arg Asp Glu Asp Ser Tyr Gly Arg Asp Pro Tyr Ser Pro
        35                  40                  45

Ser Gln Asp Pro Tyr Ser Pro Ser Gln Asp Pro Asp Arg Arg Asp Pro
    50                  55                  60

Tyr Ser Pro Ser Pro Tyr Asp Arg Arg Gly Ala Gly Ser Ser Gln His
65                  70                  75                  80

Gln Glu Arg Cys Cys Asn Glu Leu Asn Glu Phe Glu Asn Asn Gln Arg
                85                  90                  95

Cys Met Cys Glu Ala Leu Gln Gln Ile Met Glu Asn Gln Ser Asp Arg
            100                 105                 110

Leu Gln Gly Arg Gln Gln Glu Gln Gln Phe Lys Arg Glu Leu Arg Asn
        115                 120                 125

Leu Pro Gln Gln Cys Gly Leu Arg Ala Pro Gln Arg Cys Asp Leu Glu
    130                 135                 140

```
Val Glu Ser Gly Gly Arg Asp Arg Tyr
145                 150

<210> SEQ ID NO 133
<211> LENGTH: 141
<212> TYPE: PRT
<213> ORGANISM: Artificial Sequence
<220> FEATURE:
<223> OTHER INFORMATION: Arah2-ref2

<400> SEQUENCE: 133

Met Ala Arg Gln Gln Trp Glu Leu Gln Gly Asp Arg Arg Cys Gln Ser
1               5                   10                  15

Gln Leu Glu Arg Ala Asn Leu Arg Pro Cys Glu Gln His Leu Met Gln
                20                  25                  30

Lys Ile Gln Arg Asp Glu Asp Ser Tyr Glu Arg Asp Pro Tyr Ser Pro
                35                  40                  45

Ser Gln Asp Pro Tyr Ser Pro Ser Pro Tyr Asp Arg Arg Gly Ala Gly
            50                  55                  60

Ser Ser Gln His Gln Glu Arg Cys Cys Asn Glu Leu Asn Glu Phe Glu
65                  70                  75                  80

Asn Asn Gln Arg Cys Met Cys Glu Ala Leu Gln Gln Ile Met Glu Asn
                85                  90                  95

Gln Ser Asp Arg Leu Gln Gly Arg Gln Gln Glu Gln Gln Phe Lys Arg
                100                 105                 110

Glu Leu Arg Asn Leu Pro Gln Gln Cys Gly Leu Arg Ala Pro Gln Arg
            115                 120                 125

Cys Asp Leu Asp Val Glu Ser Gly Gly Arg Asp Arg Tyr
            130                 135                 140
```

UNITED STATES PATENT AND TRADEMARK OFFICE
CERTIFICATE OF CORRECTION

PATENT NO. : 11,234,445 B2
APPLICATION NO. : 16/085043
DATED : February 1, 2022
INVENTOR(S) : Bernard Bihain et al.

Page 1 of 1

It is certified that error appears in the above-identified patent and that said Letters Patent is hereby corrected as shown below:

In the Specification

Column 4,
Line 28, "(400 μs)" should read --(400μg)--.

Column 19,
Line 20, "VETE" should read --VEIE--.

Column 25,
Line 66, "ANITYK" should read --ANIIYK--.

Signed and Sealed this
First Day of November, 2022

Katherine Kelly Vidal
*Director of the United States Patent and Trademark Office*